(12) United States Patent
Katoh et al.

(10) Patent No.: US 6,630,472 B1
(45) Date of Patent: *Oct. 7, 2003

(54) COMPOUNDS, PHARMACEUTICAL COMPOSITIONS, AND METHODS FOR STIMULATING NEURONAL GROWTH AND ELONGATION

(75) Inventors: Susumu Katoh, Osaka (JP); Hiroshi Kawakami, Osaka (JP); Hiroki Tada, Osaka (JP); Maria Angelica Linton, San Diego, CA (US); Vincent Kalish, Annapolis, MD (US); John Howard Tatlock, Vista, CA (US); Jesus Ernesto Villafranca, San Diego, CA (US)

(73) Assignee: Pfizer Inc, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/356,240

(22) Filed: Jul. 16, 1999

Related U.S. Application Data

(60) Provisional application No. 60/093,299, filed on Jul. 17, 1998, and provisional application No. 60/132,884, filed on May 6, 1999.

(51) Int. Cl.$^7$ .................... C07D 471/18; C07D 471/08; C07D 498/18; A61K 31/4995; A61K 31/551
(52) U.S. Cl. ........................ 514/249; 540/520; 544/343; 544/346; 544/349
(58) Field of Search ................. 544/349, 343, 544/346; 540/520; 514/249

(56) References Cited

U.S. PATENT DOCUMENTS

| | | | |
|---|---|---|---|
| 4,894,366 A | 1/1990 | Okuhara et al. | 514/63 |
| 5,109,112 A | 4/1992 | Siekierka et al. | 530/350 |
| 5,187,166 A * | 2/1993 | Kikuchi et al. | 514/249 |
| 5,192,773 A | 3/1993 | Armistead et al. | 514/315 |
| 5,196,352 A | 3/1993 | Siekierka et al. | 436/501 |
| 5,256,656 A * | 10/1993 | Kikuchi et al. | 514/224.2 |
| 5,318,895 A | 6/1994 | Kahn et al. | 435/32 |
| 5,324,659 A | 6/1994 | Parent et al. | 435/255.2 |
| 5,330,993 A | 7/1994 | Armistead et al. | 514/315 |
| 5,344,831 A * | 9/1994 | Satoh et al. | 514/249 |
| 5,362,629 A | 11/1994 | Schreiber et al. | 435/21 |
| 5,457,182 A | 10/1995 | Wiederrecht et al. | 530/402 |
| 5,516,797 A | 5/1996 | Armistead et al. | 514/548 |
| 5,521,209 A | 5/1996 | Steiner et al. | 514/112 |
| 5,612,350 A | 3/1997 | Or et al. | 514/291 |
| 5,614,547 A | 3/1997 | Hamilton et al. | 514/423 |
| 5,616,705 A | 4/1997 | Steiner et al. | 544/105 |
| 5,622,866 A | 4/1997 | Motamedi et al. | 435/320.1 |
| 5,622,970 A | 4/1997 | Armistead et al. | 514/315 |
| 5,665,774 A | 9/1997 | Armistead et al. | 514/533 |
| 5,696,135 A | 12/1997 | Steiner et al. | 514/317 |
| 5,721,256 A | 2/1998 | Hamilton et al. | 514/330 |
| 5,780,484 A | 7/1998 | Zelle et al. | 514/316 |
| 5,786,378 A | 7/1998 | Hamilton et al. | 514/423 |
| 5,795,908 A | 8/1998 | Hamilton et al. | 514/423 |
| 5,798,355 A | 8/1998 | Steiner et al. | 514/248 |
| 5,801,187 A | 9/1998 | Li et al. | 514/365 |
| 5,801,197 A | 9/1998 | Steiner et al. | 514/548 |
| 5,811,434 A | 9/1998 | Zelle et al. | 514/307 |
| 5,861,418 A * | 1/1999 | Miyazawa et al. | 514/327 |

FOREIGN PATENT DOCUMENTS

| | | |
|---|---|---|
| WO | WO 9640140 | 12/1996 |
| WO | WO 9640633 | 12/1996 |
| WO | WO 9641609 | 12/1996 |
| WO | WO 97/16190 | 5/1997 |
| WO | WO 9813343 | 4/1998 |
| WO | WO 9813355 | 4/1998 |
| WO | WO 9820891 | 5/1998 |
| WO | WO 9820892 | 5/1998 |
| WO | WO 9820893 | 5/1998 |
| WO | WO 9825950 | 6/1998 |
| WO | WO 9829116 | 7/1998 |
| WO | WO 9829117 | 7/1998 |
| WO | WO 9835675 | 8/1998 |
| WO | WO 9837882 | 9/1998 |
| WO | WO 9837885 | 9/1998 |

OTHER PUBLICATIONS

US 5,654,332, 8/1997, Armistead (withdrawn)

Lyons et al., "Immunosuppressant FK506 promotes neurite outgrowth in cultures of PC12 cells and sensory ganglia", *Proc. Natl. Acad. Sci. USA,* 91, 3191–3195, (1994).

Fischer et al., "Nachweis einer Enzymkatalyse für die cis–trans–Isomerisierung der Peptidbindung in prolinhaltigen Peptiden", *Biomed. Biochim. Acta,* 43 (10), 1101–1111 (1984).

Fischer et al., "Conformational Specificity of Chymotrypsin Toward Proline–Containing Substrates", *Biochimica et Biophysica Acta,* 791, 87–97, (1984).

Siekierka et al., "A cytosolic binding protein for the immunosuppressant FK506 has peptidyl–prolyl isomerase activity but is distinct from cyclophilin", *Nature,* 341, 755–757 (1989).

Harding et al., "A receptor for the immunosuppressant FK506 is a cis–trans peptidyl–prolyl isomerase", *Nature,* 341, 758–760 (1989).

Snyder et al., "Immunophilins and the nervous system", *Nature Medicine,* 1 (1), 32–37 (1995).

(List continued on next page.)

*Primary Examiner*—Bruck Kifle
(74) *Attorney, Agent, or Firm*—Peter C. Richardson; Paul H. Ginsburg; Richard L. Catania

(57) ABSTRACT

Compounds that inhibit the peptidyl-prolyl isomerase (rotamase) enzyme activity of the FK-506 binding protein (FKBP) and compositions comprising these compounds are described. The FKBP-inhibiting compounds have a bicyclic [3.3.1], [4.3.1] or polycyclic azaamide nucleus. Pharmaceutical compositions containing such compounds help stimulate the outgrowth of neurites in nerve cells and augmenting nerve regeneration. Methods of treating nerve cells with such compositions are useful to promote repair of neuronal damage caused by disease and physical trauma.

26 Claims, No Drawings

OTHER PUBLICATIONS

Miyata et al., "Phosphorylation of the immunosuppressant FK506–binding protein FKBP52 by casein kinase II: Regulation of HSP90–binding activity of FKBP52", *Proc. Natl. Acad. Sci. USA*, 94, 14500–14505 (1997).

Lombardi et al., "Design of A Synthetic Receptor For The Calmodulin–Binding Domain of Calcineurin", *J. Am. Chem. Soc.*, 119, 12378–12379 (1997).

Fischer et al., "Cyclophilin and peptidyl–prolyl cis–trans isomerase are probably identical proteins", *Nature*, 337(6206), 476–478 (1989).

Timerman et al., "Selective Binding Of FKBP12.6 By The Cardiac Ryanodine Receptor", *The Journal of Biological Chemistry*, 271 (34) 20385–20391 (1996).

Wang et al., "The Immunophilin FKBP12 Functions As A Common Inhibitor Of The TGFβ Family Type I Receptors", *Cell*, 86, 435–444 (1996).

Cameron et al., "Calcineurin Associated With The Inositol 1,4,5–Trisphosphate Receptor–FKBP12 Complex Modulates $Ca^{2+}$Flux", *Cell*, 83, 463–472 (1995).

Brillantes et al., "Stabilization of Calcium Release Channel (Ryanodine Receptor) Function By FK506–Binding Protein", *Cell*, 77, 513–523 (1994).

Cameron et al., "Immunophilin FK506 binding protein associated with inositol 1,4,5–trisphosphate receptor modulates calcium flux", *Proc. Natl. Acad. Sci. USA*, 92, 1784–1788 (1995).

Flanagan et al., "Nuclear association of a T–cell transcription factor blocked by FK–506 and cyclosporin A", *Nature*, 352, 803–807 (1991).

Jayaraman et al., "FK506 Binding Protein Associated With The Calcium Release Channel (Ryanodine Receptor)", *The Journal of Biological Chemistry*, 267 (14), 9474–9477 (1992).

Standaert, "A Guide To The Rotamase Assay", Texas A&M University (Nov. 18, 1990, Revised Sep. 7, 1993, HTML version Jan. 21, 1998).

Gold BG, et al. "A nonimmunosuppressant FKBP–12 ligand increases nerve regeneration." Exp Neurol. Oct. 1, 1997; 147(2):269–278.

Amara JF, et al. "A versatile synthetic dimerizer for the regulation of protein–protein interactions." Proc Natl Acad Sci USA. Sep. 30, 1997:94(20): 10618–10623.

Ivery MT, et al. "Modeling the interaction between FK506 and FKBP12: a mechanism for formation of the calcineurin inhibitory complex." Biorg med Chem. Feb. 1, 1997; 5(2): 217–232.

Nair SC, et al. "Molecular cloning of human FKBP51 and comparisons of immunophilin interactions with Hsp90 and progesterone receptor." Mol Cell biol. Feb. 1, 1997; 17(2):594–603.

Odom A, et al. The immunosuppressant FK506 and its noimmunosuppressive analog L–684,818 are toxic to Cryptococcus neoformans by inhibition of a common target protein. Antimicrob Agents Chemother. Jan. 1, 1997; 41 (1): 156–161.

Mollison KW, et al. "Discovery of FK 506 Analogues That Are Nontoxic to Mouse Pancreatic Beta Cells in Vitro but Show Diabetogenic Potential When Administered to the Rat" Trans. Proceedings, vol. 28, No 6, pp 3185–3188, Dec., 1996.

Proc Natl Acd Science USA, 94, 2019–2024 (1997).

Toshihide Okadome et al. "Characterization of the Interaction of FKBP 12 with the Transforming Growth Factor–$\mu$ type I Receptor in Vivo*" The Journal of Bio. Chem. vol. 271, No. 38, pp. 21687–21690, Sep. 6, 1996.

Bentrice Chambraud et al. FAP48 a New Protein that Forms Specific Complexes With Both Immnophilins FKBP59 and FKBP12, vol. 271, No 51, pp. 32923–32929 Dec.

Communication from the European Patent Office in corresponding foreign Application No. 99 934 043.3, dated Jul. 5, 2002.

"Decisions of the Boards of Appeal", *Official Journal EPO*, 273–289, (Jun., 2001).

Boards of Appeal of the European Patent Office, Decision of Oct. 26, 2000, Appeal No.: T 1129/97–3.3.1, Application No.: 92911098.9, Publication No.: 0643701 (In French).

English Translation of: Boards of Appeal of the European Patent Office, Decision of Oct. 26, 2000, Appeal No.: T 1129/97–3.3.1, Application No.: 92911098.9, Publication No.: 0643701.

* cited by examiner

COMPOUNDS, PHARMACEUTICAL COMPOSITIONS, AND METHODS FOR STIMULATING NEURONAL GROWTH AND ELONGATION

CROSS-REFERENCE TO RELATED APPLICATION

This application is based on U.S. Provisional Application No. 60/093,299, filed Jul. 17, 1998. This application is also based on U.S. Provisional Application No. 60/132,884, filed May 6, 1999, the disclosure of which is incorporated by reference herein.

TECHNICAL FIELD AND INDUSTRIAL APPLICABILITY OF THE INVENTION

The present invention relates to methods and pharmaceutical compounds and compositions for stimulating neurite outgrowth in nerve cells leading to nerve regeneration. More particularly, the compositions comprise compounds that inhibit the peptidyl-prolyl isomerase (rotamase) enzyme activity associated with the FK-506 binding protein (FKBP). The methods comprise treating nerve cells with compositions comprising the rotamase-inhibiting compound. The methods of the invention can be used to promote repair of neuronal damage caused by disease or physical trauma.

BACKGROUND OF THE INVENTION

Immunophilins are a family of soluble proteins that serve as receptors for important immunosuppressant drugs such as cyclosporin A, FK-506 and rapamycin. An immunophilin of particular interest is the FK-506 binding protein (FKBP). For a review of the role of immunophilins in the nervous system, see Solomon et al., "Immunophilins and the Nervous System," *Nature Med.*, 1(1), 32–37 (1995).

The 12-kiloDalton FK-506 binding protein, FKBP12, binds FK-506 with high affinity. Such binding has been directly measured using microcalorimetry and radiolabeled FK-506, e.g., [$^3$H]dihydro-FK-506 (see Siekierka et al., *Nature*, 341, 755–57 (1989); and U.S. Pat. No. 5,696,135 to Steiner et al.) and 32-[1-$^{14}$C]-benzoyl-FK-506 (see Harding et al., *Nature*, 341, 758–60 (1989)). Binding affinity of other compounds for FKBP can be determined directly by microcalorimetry or from competitive binding assays using either tritiated or $^{14}$C-labelled FK-506, as described by Siekierka et al. or Harding et al.

FK-506-binding protein FKBP12 participates in a variety of significant cellular functions. FKBP12 catalyzes cis-trans isomerization of peptidyl-prolyl linkages. This peptidyl-prolyl isomerase enzyme activity is also referred to as rotamase activity. Such activity is readily assayed by methods known in the art (see Fischer et al., *Biochim. Biophys. Acta* 791, 87 (1984); Fischer et al., *Biomed. Biochim. Acta* 43, 1101 (1984); and Fischer et al., *Nature* 337, 476–478 (1989)). U.S. Pat. Nos. 5,192,773 and 5,330,993 to Armistead et al. report FKBP binding affinities that were correlated with rotamase-inhibiting activities for many compounds.

FK-506 and compounds that bind FKBP competitively with FKBP stimulate outgrowth of neurites (axons) in nerve cells (see U.S. Pat. No. 5,696,135 to Steiner et al.). Lyons et al. (*Proc. Natl. Acad, Sci, USA*, 91, 3191–95 (1994)) demonstrated that FK-506 acts to enhance or potentiate the effectiveness of nerve growth factor (NGF) in stimulating neurite outgrowth in a rat pheochromocytoma cell line. The mechanism of stimulation of such neurite outgrowth appears to be 10- to 100-fold potentiation of the action of nerve growth factor.

Potency for inhibition of the peptidyl-prolyl isomerase (rotamase) enzyme activity of FKBP by FK-506, and by compounds that competitively inhibit FK-506 binding to FKBP, empirically correlates with activity for stimulation of neurite outgrowth. Because of the close correlation between rotamase inhibition and neurotrophic action, it has been proposed that the rotamase may convert a protein substrate into a form that promotes neural growth (see U.S. Pat. No. 5,696,135). For example, it has been found that FKBP12 forms bound complexes with the intracellular calcium ion channels—the ryanodine receptor (RyR) and the inositol 1,4,5-triphosphate receptor (IP$_3$R) (Jayaraman et al., *J. Biol. Chem.*, 267, 9474–9477 (1992); Cameron et al., *Proc. Natl. Acad. Sci, USA*, 92, 1784–1788 (1995)), helping to stabilize calcium release. For both the RyR and the IP$_3$R, it has been demonstrated that FK-506 and rapamycin are capable of dissociating FKBP12 from these receptors. In both cases, the "stripping" off of FKBP12 leads to increased leakiness of the calcium channels and lower intracellular calcium concentrations. It has been suggested that calcium flux may be associated with stimulation of neurite outgrowth.

In addition, FK-506-FKBP bound complexes bind to and inhibit calcineurin, a cytoplasmic phosphatase. The phosphatase activity of calcineurin is necessary for dephosphorylation and subsequent translocation into the nucleus of nuclear factor of activated T-cells (NF-AT) (see Flanagan et al., *Nature*, 352, 803–807 (1991)). NF-AT is a transcription factor that initiates interleukin-2 gene activation, which in turn mediates T-cell proliferation; these steps are important to the activation of an immune response. Calcineurin-inhibiting activity is correlated with the immunosuppressant activity of FK-506 and related compounds.

Calcineurin inhibition, however, does not correlate with the stimulation of neurite outgrowth. Therefore, compounds that are potent inhibitors of rotamase but not strong inhibitors of calcineurin are desired since they should be neurotrophic but non-immunosuppressive.

Such neurotrophic agents desirably find use in augmenting neurite outgrowth, and hence in promoting neuronal growth and regeneration in various pathological situations where neuronal repair can be facilitated, including peripheral nerve damage caused by injury or diseases such as diabetes, brain damage associated with stroke, and for the treatment of neurological disorders related to neurodegeneration, including Parkinson's disease, Alzheimer's disease, and amyotrophic lateral sclerosis (ALS). Further, such use is preferably without the associated effect of immunosuppression, since long-term use of immunosuppressants is associated with side effects such as kidney toxicity, neurological deficits, and vascular hypertension.

Various inhibitors of rotamase enzyme activity, FKBP-binding compounds, or immunomodulating compounds are known. See, e.g., U.S. Pat. Nos. 5,192,773, 5,330,993, 5,516,797, 5,612,350, 5,614,547, 5,622,970, 5,654,332, 5,665,774, 5,696,135, and 5,721,256. See also International Publication Nos. WO 96/41609, WO 96/40633, and WO 96/40140.

In view of the variety of disorders that may be treated by stimulating neurite outgrowth and the relatively few potent FKBP12-binding compounds that are known to possess this property, there remains a need for additional neurotrophic, rotamase-binding compounds. Such compounds will desirably have physical and chemical properties suitable for use in pharmaceutical preparations, e.g., bioavailability, half-life, and efficient delivery to the active site. In view of the desired properties, small organic molecules are preferred over proteins. Furthermore, such compounds will desirably lack significant immunosuppressive activity.

SUMMARY OF THE INVENTION

It is therefore an object of the invention to provide small-molecule neurotrophic agents. An additional object is to achieve rotamase-binding compounds that are non-immunosuppressive agents. It is a further object of the invention to provide effective processes for synthesizing such compounds as well as useful intermediates therefor. Another object of the invention is to provide methods for treating patients having neurological trauma or disorders as a result of, or associated with, conditions that include (but are not limited to) neuralgias, muscular dystrophy, Bell's palsy, myasthenia gravis, Parkinson's disease, Alzheimer's disease, multiple sclerosis, ALS, stroke and ischemia associated with stroke, neural parapathy, other neural degenerative diseases, motor neuron diseases, and nerve injuries including spinal cord injuries.

Such objects have been achieved by the rotamase-binding agents of the present invention, which may be used to stimulate the growth and regeneration of neurons. The administration of these agents to individuals requiring therapeutic stimulation of neuronal growth and regeneration provides effective therapies in various pathological situations where neuronal repair can be facilitated, including peripheral nerve damage caused by injury or disease such as diabetes, brain damage associated with stroke, and for the treatment of neurological disorders related to neurodegeneration, including Parkinson's disease, Alzheimer's disease, and amyotrophic lateral sclerosis.

In one general embodiment, the rotamase-binding agents of the invention include compounds of the general structural formula (I-a):

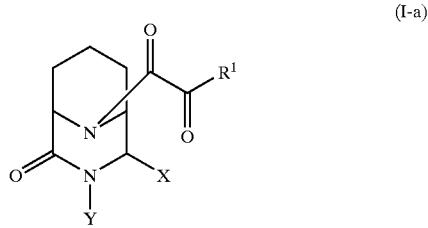

(I-a)

wherein:
R$_1$ is selected from hydrogen, substituted and unsubstituted alkyl, alkenyl, aryl, C$_3$–C$_8$ cycloalkyl, and C$_5$–C$_7$ cycloalkenyl groups, and C(R$^{11}$)(R$^{12}$)(R$^{13}$), the alkyl and alkenyl groups being optionally substituted with C$_1$–C$_4$ alkyl, C$_2$–C$_4$ alkenyl, C$_4$–C$_6$ cycloalkenyl, or hydroxy, the aryl group being optionally substituted with halogen, hydroxyl, NO$_2$, CF$_3$, C$_1$–C$_6$ alkyl, C$_2$–C$_6$ alkenyl, C$_1$–C$_4$ alkyloxy, C$_2$–C$_4$ alkenyloxy, benzyloxy, phenoxy, amino, or phenyl, and the cycloalkyl and cycloalkenyl groups being optionally substituted with C$_1$–C$_4$ alkyl, C$_2$–C$_4$ alkenyl, C$_1$–C$_4$ alkyloxy, or hydroxy, and R$^{11}$ and R$^{12}$ each independently being lower alkyl, or R$^{11}$ and R$^{12}$ together with the atom to which they are bound forming cycloalkyl, and R$^{13}$ being H, OH, lower alkyl, aryl, or (CH$_2$)$_n$—O—W$^1$, where n is 0, 1, 2, or 3, W$^1$ is R$^2$ or C(O)R$^2$, and R$^2$ is C$_1$–C$_3$ alkyl optionally substituted with one or two methoxy groups;

X is selected from hydrogen, cyano, C$_1$–C$_2$ alkyloxy, dimethoxymethyl, and oxygen, where when X is oxygen, the C—X bond (i.e., the bond connecting X to the ring carbon atom) is a double bond; and Y is selected from hydrogen, alkyl, alkenyl, and cycloalkyl, the alkyl, alkenyl, and cycloalkyl groups being optionally substituted in one or more positions with substituents selected from substituted and unsubstituted alkyl, aryl, alkoxy, hydroxyalkyl, aryloxy, alkenyloxy, hydroxy, (CH$_2$)$_p$—O—W$^2$, and (CH$_2$)$_p$—N—W$^2$, where p is 0, 1, or 2, and W$^2$ is R$^3$ or C(O)R$^3$, where R$^3$ is alkyl, alkenyl, or aryl optionally substituted with alkyl, aryl, or alkoxy; or X and Y taken together with the nitrogen heteroatom of the ring structure to which Y is connected (shown in formula (I-a)) form a 5- to 7-membered saturated or unsaturated heterocyclic ring optionally containing one additional heteroatom (i.e., one heteroatom in addition to the depicted nitrogen atom of the ring structure) selected from 0 and N, the 5- to 7-membered saturated or unsaturated heterocyclic ring being optionally substituted with one or more substituents selected from J, K, and L, which are independently oxygen, C$_3$–C$_5$ cycloalkyl, or C$_1$–C$_5$ alkyl optionally substituted with one or two substituents independently selected from C$_3$–C$_5$ cycloalkyl, methoxy, methoxyphenyl, or dimethoxyphenyl, or J and K taken together form a phenyl ring optionally substituted with one or more substituents selected from methoxy, trifluoromethyl, trifluoromethoxy, and suitable substituents linked to the phenyl ring through oxygen, nitrogen, carbon, or sulfur.

In an alternative general embodiment, the invention is directed to compounds of formula (I-b):

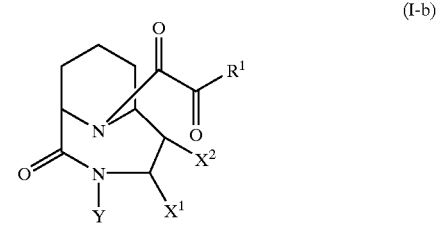

(I-b)

wherein:
R$^1$ is selected from hydrogen, substituted and unsubstituted alkyl, alkenyl, aryl, C$_3$–C$_8$ cycloalkyl, and C$_5$–C$_7$ cycloalkenyl groups, and C(R$^{11}$)(R$^{12}$)(R$^{13}$), the alkyl and alkenyl groups being optionally substituted with C$_1$–C$_4$ alkyl, C$_2$–C$_4$ alkenyl, C$_4$–C$_6$ cycloalkenyl, or hydroxy, the aryl group being optionally substituted with halogen, hydroxyl, NO$_2$, CF$_3$, C$_1$–C$_6$ alkyl, C$_2$–C$_6$ alkenyl, C$_1$–C$_4$ alkyloxy, C$_2$–C$_4$ alkenyloxy, benzyloxy, phenoxy, amino, or phenyl, and the cycloalkyl and cycloalkenyl groups being optionally substituted with C$_1$–C$_4$ alkyl, C$_2$–C$_4$ alkenyl, C$_1$–C$_4$ alkyloxy, or hydroxy, and R$^{11}$ and R$^{12}$ each independently being lower alkyl, or R$^{11}$ and R$^{12}$ together with the atom to which they are bound forming cycloalkyl, and R$^{13}$ being H, OH, lower alkyl, aryl, or (CH$_2$)$_n$—O—W$^1$, where n is 0, 1, 2, or 3, W$^1$ is R$^2$ or C(O)R$^2$, and R$^2$ is C$_1$–C$_3$ alkyl optionally substituted with one or two methoxy groups;

X$^1$ and X$^2$ are each independently selected from hydrogen, cyano, C$_1$–C$_2$ alkyloxy, dimethoxymethyl, and oxygen, where when X$^1$ or X$^2$ is oxygen, the C—X bond (i.e., the bond connecting X$^1$ or X$^2$ to the ring carbon atom) is a double bond (i.e, X$^1$ or X$^2$ is =O); or X$^1$ and X$^2$ together form a valence bond; and Y is selected from hydrogen, alkyl, alkenyl, and cycloalkyl, the alkyl, alkenyl, and cycloalkyl groups being optionally substituted in one or more positions with substituents selected from substituted and unsubstituted alkyl, aryl, alkoxy, hydroxyalkyl, aryloxy, alkenyloxy, hydroxy, $(CH_2)_p$—O—$W^2$, and $(CH_2)_p$—N—$W^2$, where p is 0, 1, or 2, and $W^2$ is $R^3$ or $C(O)R^3$, where $R^3$ is alkyl, alkenyl, or aryl optionally substituted with alkyl, aryl, or alkoxy; or one of $X^1$ and $X^2$ in combination with Y taken together with the nitrogen heteroatom of the ring structure to which Y is connected (shown in formula (I-b)) form a 5- to 7-membered saturated or unsaturated heterocyclic ring optionally containing one additional heteroatom (i.e., one heteroatom in addition to the depicted nitrogen atom of the ring structure) selected from O and N, the 5- to 7-membered saturated or unsaturated heterocyclic ring being optionally substituted with one or more substituents selected from J, K, and L, which are independently oxygen, $C_3$–$C_5$ cycloalkyl, or $C_1$–$C_5$ alkyl optionally substituted with one or two substituents independently selected from $C_3$–$C_5$ cycloalkyl, methoxy, methoxyphenyl, or dimethoxyphenyl, or J and K taken together form a phenyl ring optionally substituted with one or more substituents selected from methoxy, trifluoromethyl, trifluoromethoxy, and suitable substituents linked to the phenyl ring through oxygen, nitrogen, carbon, or sulfur.

The rotamase-inhibiting agents of the invention also include pharmaceutically acceptable derivatives of such compounds of the formula (I-a) or (I-b).

The invention further relates to methods of treating neurological trauma or disorders as a result of, or associated with, conditions including neuralgias, muscular dystrophy, Bell's palsy, myasthenia gravis, Parkinson's disease, Alzheimer's disease, multiple sclerosis, amyotrophic lateral sclerosis (ALS), stroke and ischemia associated with stroke, neural parapathy, other neural degenerative diseases, motor neuron diseases, and nerve injuries including spinal cord injuries. The inventive methods comprise administering a therapeutically effective amount of a compound of formula (I-a) or (I-b), or a prodrug, pharmaceutically active metabolite, or pharmaceutically acceptable (nontoxic) salt thereof, to a patient in need of such treatment. Such methods further comprise administering a composition comprising an effective amount of a compound of formula (I-a) or (I-b), or a prodrug, pharmaceutically active metabolite, or pharmaceutically acceptable salt thereof, in combination with a pharmaceutically acceptable carrier or diluent and/or a therapeutically effective amount of a neurotrophic factor selected from nerve growth factor, insulin growth factor and its active truncated derivatives, acidic and basic fibroblast growth factor, platelet-derived growth factors, brain-derived neurotrophic factor, ciliary neurotrophic factors, glial cell line-derived neurotrophic factor, neurotrophin-3, and neurotrophin 4/5, to a patient in need of such treatment.

The invention also relates to intermediates of formulae (II), (III), and (V), which are described below and are useful for preparing the FKBP-modulating compounds of formula (I-a) and (I-b). The invention further relates to processes of making the compounds using such intermediates.

Other features, objects, and advantages of the invention will become apparent from the following detailed description of the invention.

DETAILED DESCRIPTION AND PREFERRED EMBODIMENTS

FKBP-Inhibiting Agents of the Invention

As used herein, the following terms have the defined meanings, unless indicated otherwise.

The term "alkyl" means a branched or straight-chained (linear) paraffinic hydrocarbon group (saturated aliphatic group) having from 1 to 10 carbon atoms, which may be generally represented by the formula $C_kH_{2k+1}$, where k is an integer of from 1 to 10. Examples of alkyls include methyl, ethyl, n-propyl, isopropyl, n-butyl, isobutyl, t-butyl, pentyl, n-pentyl, isopentyl, neopentyl, and hexyl and the simple aliphatic isomers thereof. The term "lower alkyl" designates an alkyl having from 1 to 8 carbon atoms (i.e., a $C_1$–$C_8$ alkyl).

The term "alkenyl" means a branched or straight-chained olefinic hydrocarbon group (unsaturated aliphatic group having one or more double bonds) containing 2 to 10 carbons. Exemplary alkenyls include ethenyl, 1-propenyl, 2-propenyl, 1-butenyl, 2-butenyl, isobutenyl, and the various isomeric pentenyls and hexenyls (including both cis and trans isomers).

The term "alkoxy" means —O-alkyl, where "alkyl" is as defined above. "Lower alkoxy" refers to alkoxy groups containing an alkyl moiety of 1 to 4 carbon atoms.

The term "alkenyloxy" means —O-alkenyl, where "alkenyl" is as defined above.

The term "aryl" means a monocyclic or polycyclic aromatic ring moiety, for example, phenyl, naphthyl, furyl, thienyl, pyrrolyl, pyridyl, pyridinyl, pyrazolyl, imidazolyl, pyrazinyl, triazinyl, oxadiazolyl, H-tetrazol-5-yl, indolyl, quinolinyl, benzofuranyl, benzothiophenyl (thianaphthenyl) and the like. Where indicated, such aryl moieties may be optionally substituted with one or more substituents, for example, a halogen (F, Cl, I, Br), lower alkyl, —OH, —$NO_2$, —CN, —$CO_2H$, —O-lower alkyl, aryl, —O-aryl, aryl-lower alkyl, —$CO_2CH_3$, —$CONH_2$, —$OCH_2CONH_2$, —$NH_2$, —$SO_2NH_2$, —$OCHF_2$, —$CF_3$, —$OCF_3$, and the like. Aryl moieties may also be substituted by two substituents forming a bridge, for example —O—$(CH_2)_z$—O—, where z is an integer of from 1 to 3.

The term "aryl-lower alkyl" means a lower alkyl (as defined above) substituted with an aryl.

The term "aryloxy" means —O-aryl, where "aryl" is as defined above.

The term "cycloalkyl" means a monocyclic or polycyclic carbocyclic ring structure, where each ring has from five to seven carbon atoms and is saturated. Examples of cycloalkyls include cyclopropyl, cyclobutyl, cyclopentyl, cyclohexyl, cycloheptyl, and adamantyl. Where indicated, a cycloalkyl may be substituted with one or more suitable substituents, for example, halogen, alkyl, —OR, or —SR, where R is alkyl or aryl.

The term "cycloalkenyl" means a monocyclic or polycyclic carbocyclic ring structure, where each ring has from five to seven carbon atoms and at least one ring is partially unsaturated or has at least one double bond.

The term "heterocycle" (or the root "hetero" in reference to a ring structure) means a ring structure containing one or more heteroatoms (non-carbon ring atoms) selected from O, N, and S. Thus, the term "heterocycloalkyl" means a cycloalkyl in which at least one ring carbon atom is replaced by a heteroatom selected from O, N and S.

Rotamase-inhibiting compounds of the invention are represented by the formula (I-a) and (I-b) defined above. Preferably, the rotamase-inhibiting compounds inhibit the rotamase (peptidyl-prolyl isomerase) enzyme activity of FKBP, in particular, FKBP12. In addition to compounds of the formula (I-a) and (I-b), rotamase-inhibiting agents of the invention include pharmaceutically acceptable derivatives of such compounds, such as prodrugs, pharmaceutically active metabolites, and pharmaceutically acceptable salts or solvates thereof.

In preferred embodiments of compounds represented by the above formulae (I-a) and (I-b), X, $X^1$ and $X^2$ are hydrogen or oxygen, or $X^1$ and $X^2$ form a valence bond.

In preferred compounds represented by the above formulae (I-a) and (I-b), Y is alkyl having one or more substituents selected from substituted and unsubstituted alkyl, aryl, alkoxy, hydroxyalkyl, aryl-alkyl, aryloxy, alkenyloxy, hydroxy, $(CH_2)_p$—O—$W^2$, and $(CH_2)_p$—N—$W^2$, wherein p is 0, 1, or 2, and $W^2$ is $R^3$ or $C(O)R^3$, where $R^3$ is alkyl, alkenyl, or aryl optionally substituted with alkyl, aryl, or alkoxy. In more preferred embodiments, Y is:

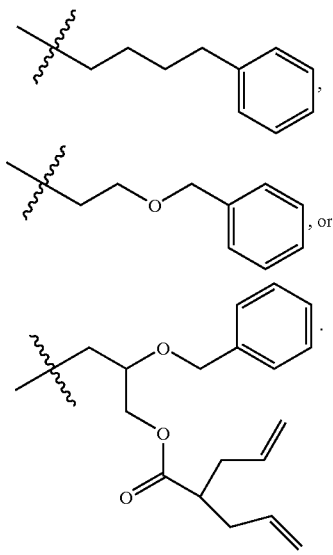

In other preferred embodiments, X, or one of $X^1$ and $X^2$, and Y together with any intervening ring atoms form a substituted or unsubstituted piperidine or piperazine ring.

For compounds represented by the above formula (I-a), $R^1$ is preferably selected from: 3,4,5-trimethoxyphenyl;

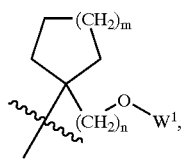

where m is 1 or 2, and n is 0, 1, or 2; and $C(R^{11})(R^{12})(R^{13})$, where $R^{11}$ and $R^{12}$ are independently selected from methyl and ethyl, and $R^{13}$ is selected from H, OH, lower alkyl, aryl, and $(CH_2)_n$—O—$W^1$, where n is 0, 1, 2, or 3. In the above formulae, $W^1$ is $R^2$ or $C(O)R^2$, where $R^2$ is preferably $C_1$–$C_3$ alkyl optionally substituted with one or two methoxy groups.

Especially preferred species of compounds represented by the above formula (I-a) are the following:

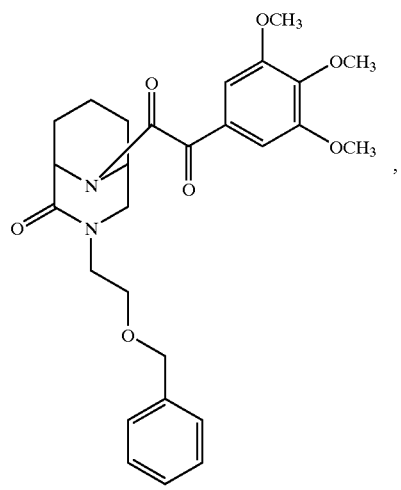

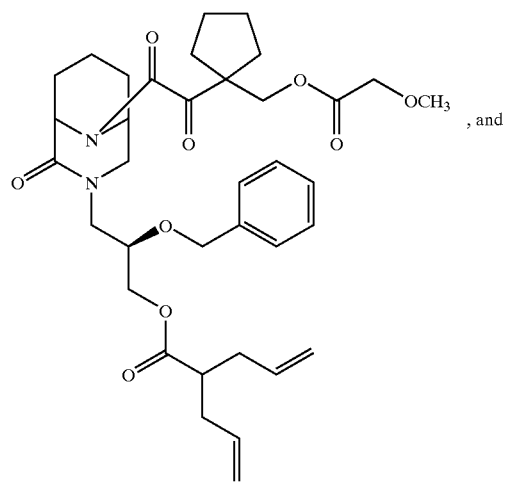

, and

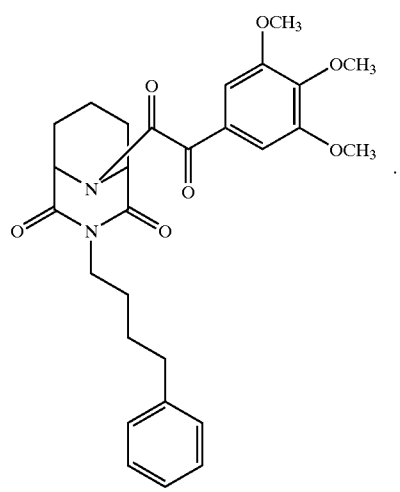

Especially preferred species of compounds represented by the above formula (I-b) are the following:

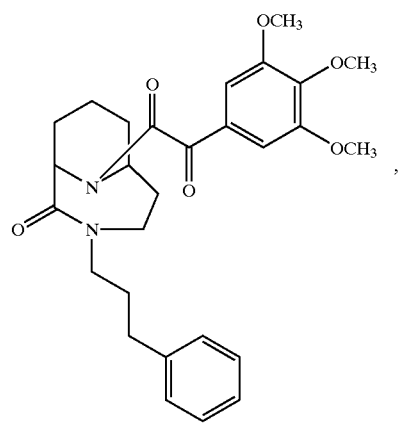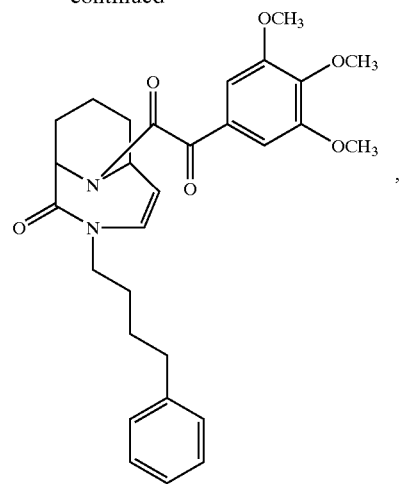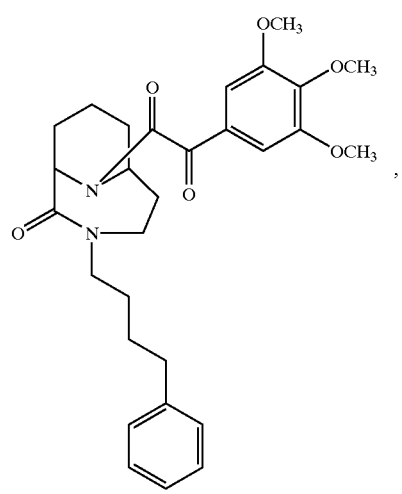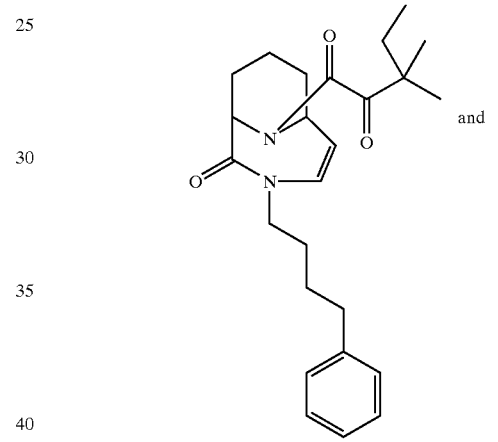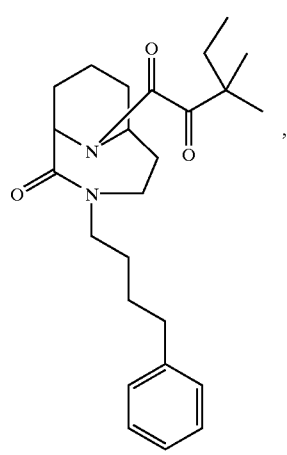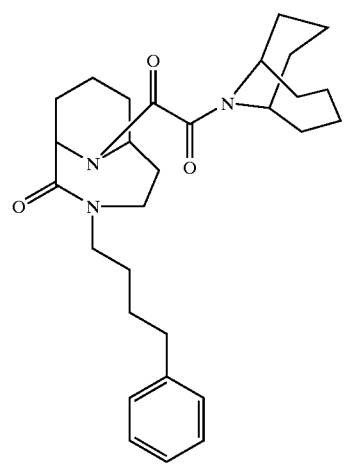

The compounds of the invention also include pharmaceutically acceptable derivatives of compounds of the formula (I-a) and (I-b). A "pharmaceutically acceptable derivative" denotes a prodrug, pharmaceutically active metabolite, or pharmaceutically acceptable salt, ester, salt of such ester, or hydrate of a compound of this invention. Such compounds, when administered to a patient, are capable of directly or indirectly yielding a compound of this invention, or a metabolic residue or product thereof, and thereby inhibit FKBP rotamase activity or promote or augment neurite outgrowth.

The compounds of formula (I-a) and (I-b) may be used in pharmaceutical compositions in the form of pharmaceutically acceptable salts. Such salts are preferably derived from inorganic or organic acids and bases. Exemplary acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Exemplary base salts include ammonium salts, alkali metal salts, such as sodium and potassium salts, alkaline earth metal salts, such as calcium and magnesium salts, salts with organic bases, such as dicyclohexylamine salts, N-methyl-D-glucosamine salt, and salts with amino acids such as arginine and lysine. Also, the basic nitrogen-containing groups can be quaternized with such agents as: lower alkyl halides, such as methyl, ethyl, propyl, and butyl chlorides, bromides or iodides; dialkyl sulfates, such as dimethyl, diethyl, dibutyl, and diamyl sulfates; long-chain halides such as decyl, lauryl, myristyl and stearyl chlorides, bromides, and iodides; and aralkyl halides, such as benzyl and phenethyl bromides. Water- or oil-soluble or dispersible products may be prepared from such salts.

In addition, the compounds of the invention may be modified by appending appropriate functionalities to enhance selective biological properties. Such modifications, which are within the purview of the ordinarily skilled artisan, include those increasing biological penetration into a given biological system (e.g., blood, lymphatic system, central nervous system), increasing oral availability, increasing solubility to allow administration by injection, altering metabolism, and altering rate of excretion.

Some of the compounds described herein contain one or more centers of asymmetry and may thus give rise to enantiomers, diastereoisomers, rotamers, and other stereoisomeric forms. The present invention is meant to include all such possible stereoisomers as well as their racemic and optically pure forms. Optically active (R) and (S) isomers may be prepared using chiral synthons or chiral reagents, or resolved using conventional techniques. When the compounds described herein contain olefinic double bonds, they are intended to include both E and Z geometric isomers. Furthermore, the present invention is meant to include all such possible rotamners, particularly those having different orientations around the bond as follows:

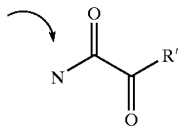

Moreover, the chemical formulae referred to herein may exhibit the phenomenon of tautomerism. As the formulae drawings within this specification can only represent one of the possible tautomeric forms, it should be understood that the invention encompasses any tautomeric form that can be generated by employing the tools disclosed or in a known manner, and is not limited to any one tautomeric form depicted by the formulae.

Synthetic Methods

Compounds of the formula (I-a) may be prepared from compounds from the formula (III):

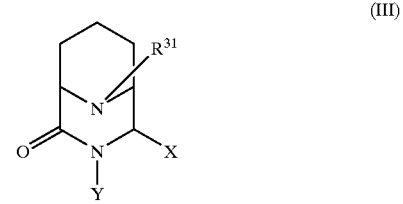

(III)

In formula (III), $R^{31}$ is selected from hydrogen and optionally substituted alkyl, alkenyl, aryl, cycloalkyl, cycloalkenyl,

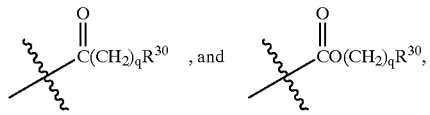

where q is 0 or 1, and $R^{30}$ is an alkyl or aryl group unsubstituted or substituted with one or more substituents independently selected from hydroxyl, $C_1$–$C_6$ alkyl, $C_2$–$C_6$ alkenyl, $C_1$–$C_4$ alkyloxy, $C_2$–$C_4$ alkenyloxy, benzyloxy, phenoxy, and phenyl. X is hydrogen, cyano, $C_1$–$C_2$ alkyloxy, dimethoxymethyl, or oxygen, where when X is oxygen, the bond connecting X to the ring carbon atom is a double bond; and Y is hydrogen, an alkyl, alkenyl, or cycloalkyl group unsubstituted or substituted with one or more substituents independently selected from alkyl, aryl, alkoxy, hydroxyalkyl, aryloxy, alkenyloxy, and hydroxy groups unsubstituted or substituted with one or more substituents independently selected from hydroxyl, $C_1$–$C_6$ alkyl, $C_2$–$C_6$ alkenyl, $C_1$–$C_4$ alkyloxy, $C_2$–$C_4$ alkenyloxy, benzyloxy, phenoxy, and phenyl, $(CH_2)_p$—O—$W^2$, or $(CH_2)_p$—N—$W^2$, where p is 0, 1, or 2, and $W^2$ is $R^3$ or $C(O)R^3$, with $R^3$ being an alkyl, alkenyl, or aryl group unsubstituted or substituted with one or more substituents independently selected from alkyl, aryl, and alkoxy. Alternatively, X and Y, together with the carbon ring atom and nitrogen heteroatom to which they are respectively bonded, form a 5- to 7-membered saturated or unsaturated heterocyclic ring unsubstituted or substituted with one or more substituents J, K, and L; where J, K, and L represent substituents indepen dently selected from oxygen, and C₃–C₅ cycloalkyl and C₁–C₅ alkyl groups unsubstituted or substituted with one or more substituents independently selected from C₃–C₅ cycloalkyl, methoxy, methoxyphenyl, and dimethoxyphenyl; or where J and K together form a phenyl ring unsubstituted or substituted with one or more substituents independently selected from methoxy, trifluoromethyl, trifluoromethoxy, and substituents linked to the phenyl ring through oxygen, nitrogen, carbon or sulfur and independently selected from halogen, hydroxyl, NO₂, CF₃, C₁–C₆ alkyl, C₂–C₆ alkenyl, C₁–C₄ alkyloxy, C₂–C₄ alkenyloxy, benzyloxy, phenoxy, amino, and phenyl.

In a preferred embodiment, R³¹ is

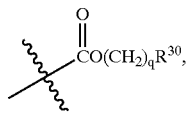

more preferably benzyloxycarbonyl.

Especially preferred examples of compounds of the formula (III) is:

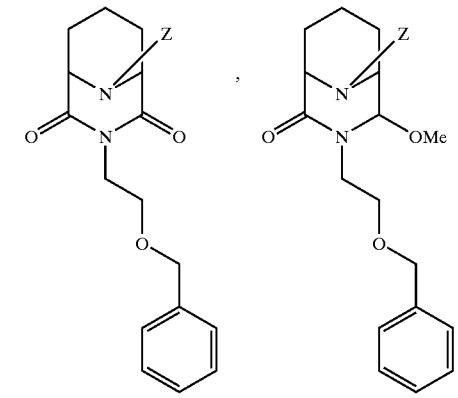

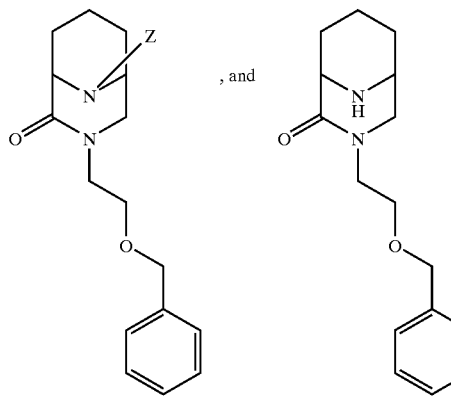

where Z is benzyloxycarbonyl. Other preferred examples of compounds of the formula (III) are:

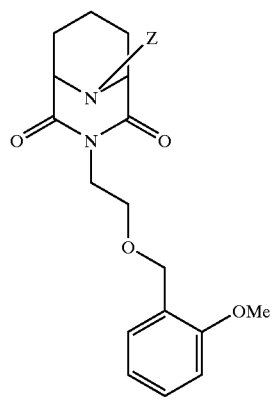

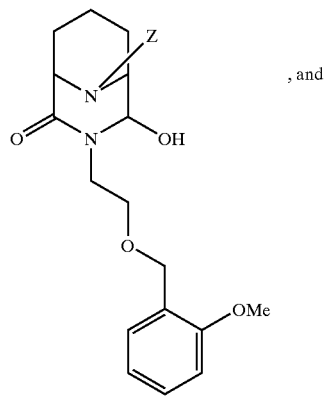

, and

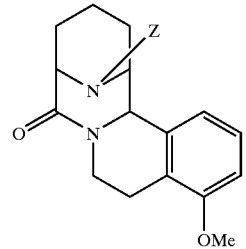

where Z is benzyloxycarbonyl. Another group of preferred compounds of the formula (III) are:

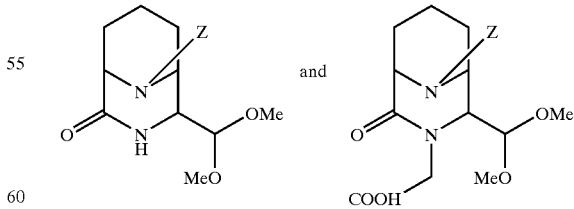

where Z is benzyloxycarbonyl.

Further preferred formula (III) compounds are selected from:

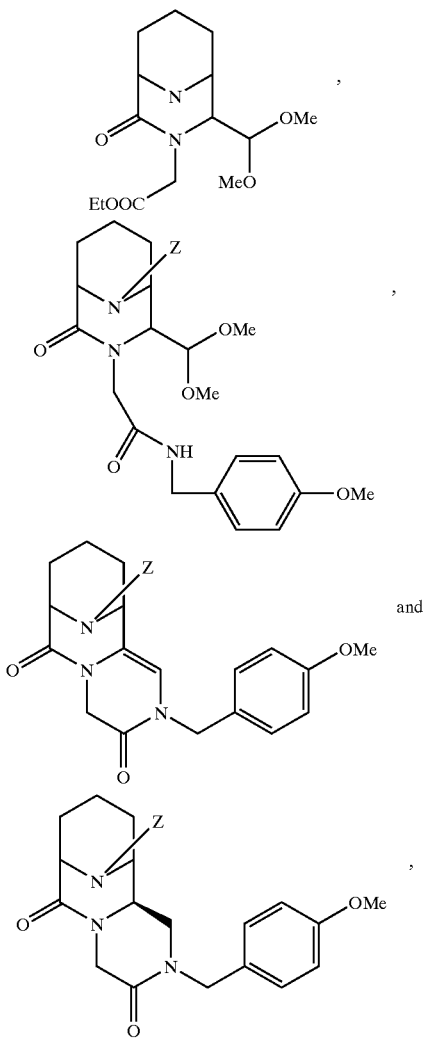

where Z is benzyloxycarbonyl.

Compounds of the formula (III) include those of the formula (III-a), which may be converted under reducing conditions into compounds of the formula (III-b).

(III-a)

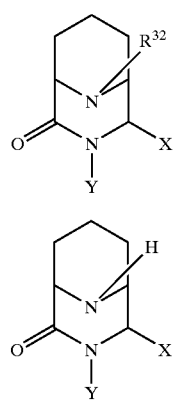

(III-b)

In formulae (III-a), $R^{32}$ is selected from optionally substituted alkyl, alkenyl, aryl, cycloalkyl, cycloalkenyl,

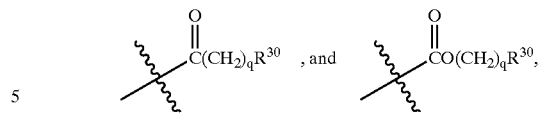

where q is 0 or 1, and $R^{30}$ is an aryl group unsubstituted or substituted with one or more substituents independently selected from hydroxyl, $C_1$–$C_6$ alkyl, $C_2$–$C_6$ alkenyl, $C_1$–$C_4$ alkyloxy, $C_2$–$C_4$ alkenyloxy, benzyloxy, phenoxy, and phenyl. In formulae (III-a) and (III-b), X and Y are as defined in formula (I-a). To yield a compound of the formula (I-a), a compound of the formula (III-b) is coupled with a compound of the formula (IV):

(IV)

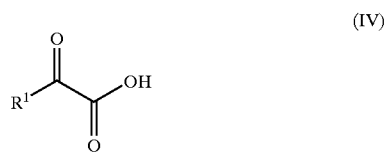

In formula (IV), $R^1$ is as defined in formula (I-a).

Compounds of the formula (III-a) may be prepared using compounds of the formula (II):

(II)

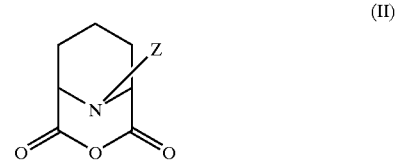

In formula (II), Z is

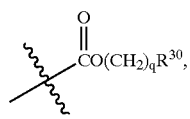

wherein q is 0 or 1, and $R^{30}$ is an alkyl or aryl group unsubstituted or substituted with one or more substituents independently selected from hydroxyl, $C_1$–$C_6$ alkyl, $C_2$–$C_6$ alkenyl, $C_1$–$C_4$ alkyloxy, $C_2$–$C_4$ alkenyloxy, benzyloxy, phenoxy, and phenyl. Preferably, Z is benzyloxycarbonyl.

Compounds of formula (I-b) may be prepared from compounds of formula (V) by methods analogous to those described above.

(V)

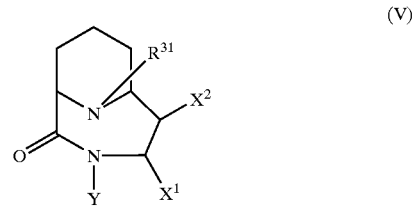

Compounds of the formula (V) include those of the formula (V-a), which may be converted under reducing conditions into compounds of the formula (V-b):

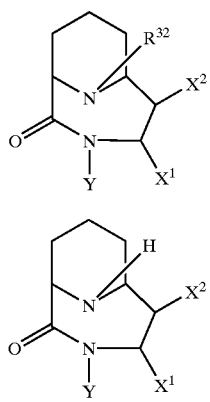

(V-a)

(V-b)

In formulae (V), (V-a) and (V-b):

$R^{31}$ and $R^{32}$ are as defined for formulae (III), (III-a) and (III-b);

$X^1$ and $X^2$ are each independently hydrogen, cyano, $C_1$–$C_2$ alkyloxy, dimethoxymethyl, or =O, or $X^1$ and $X^2$ together form a valence bond; and Y is as defined for formulae (III), (III-a) and (III-b); or one of $X^1$ and $X^2$ in combination with Y and the carbon ring atom and nitrogen heteroatom to which they are respectively bonded and any intervening ring atoms form a 5- to 7-membered saturated or unsaturated heterocyclic ring unsubstituted or substituted with one or more substituents J, K, and L, where J, K, and L are each independently selected from oxygen and $C_3$–$C_5$ cycloalkyl and $C_1$–$C_5$ alkyl groups unsubstituted or substituted with one or more substituents independently selected from $C_3$–$C_5$ cycloalkyl, methoxy, methoxyphenyl, and dimethoxyphenyl, or J and K together form a phenyl ring unsubstituted or substituted with one or more substituents independently selected from methoxy, trifluoromethyl, trifluoromethoxy, and substituents linked to the phenyl ring through oxygen, nitrogen, carbon or sulfur that are independently selected from halogen, hydroxyl, $NO_2$, $CF_3$, $C_1$–$C_6$ alkyl, $C_2$–$C_6$ alkenyl, $C_1$–$C_4$ alkyloxy, $C_2$–$C_4$ alkenyloxy, benzyloxy, phenoxy, amino, and phenyl.

Exemplary syntheses are described below to illustrate preferred embodiments and features of the invention.

The following synthesis protocols refer to intermediate compounds and final products identified in the specification and in the synthesis schemes. The preparation of various compounds of the present invention is described in detail using the following examples, but the artisan will readily recognize that the chemical reactions described are generally applicable to prepare other FKBP-inhibiting compounds of the invention. When, as an artisan will recognize, a reaction for making one compound may not be applicable precisely as described for making certain compounds of the invention, the artisan may readily determine that either the desired synthesis can be successfully performed by making appropriate modifications in light of knowledge in the art (e.g., by appropriate blocking of interfering or protecting groups, by substituting other conventional reagents, or by routine modifications of reaction conditions), or that another reaction disclosed (or analogous to that disclosed) herein or a conventional method will be appropriate to prepare such compound. Although certain protecting groups (groups that block reaction(s) with one or more inherent functional groups) are exemplified in the syntheses described below, other suitable protecting groups will be apparent to artisans depending on the functionality and particular chemistry employed. See, e.g., Greene and Wutz, *Protecting Groups in Chemical Synthesis* ($2^{nd}$ ed.), John Wiley & Sons, NY (1991).

In all synthetic processes described herein (unless otherwise indicated) the starting materials are known, available, or may be readily prepared from known starting materials, all temperatures are set forth in degrees Celsius, and all parts and percentages are by weight. Reagents were purchased from commercial suppliers, such as Aldrich Chemical Company or Lancaster Synthesis Ltd. Reagents and solvents were commercial grades and were used as supplied with the following exceptions: dichloromethane ($CH_2Cl_2$) was distilled from calcium hydride prior to use; tetrahydrofuran (THF) was distilled from sodium benzophenone ketyl prior to use; and methanol was dried over 4-Ångstrom molecular sieves.

Flash column chromatography was performed using silica gel 60 (Merck Art 9385). $^1$H-NMR (300 MHz) spectra were measured in $CDCl_3$ solutions and were determined on a Varian-300 instrument using Varian UNITYplus300 operating software. Chemical shifts are reported in parts per million (ppm) downfield from tetramethylsilane as the internal standard, and coupling constants are given in Hertz. The following abbreviations are used for spin multiplicity: br=broad, s=singlet, d=doublet, t=triplet, q=quartet, m=multiplet, and cm=complex multiplet. Infrared (IR) spectra were recorded on a Perkin-Elmer 1600 series FTIR spectrometer and are reported in wavenumbers ($cm^{-1}$). Elemental analyses were performed by Atlantic Microlab, Inc., Norcross, Ga. High-resolution mass spectra (HRMS) were performed by Scripps Mass Spectra Laboratory, La Jolla, Calif. Melting points (mp) were determined on a Mel-Temp II apparatus and are uncorrected.

Unless otherwise indicated, the reactions set forth below were carried out under a positive pressure with a balloon of nitrogen ($N_2$) or argon (Ar) at ambient temperature in anhydrous solvents, and the reaction flasks were fitted with rubber septa for the introduction of substrates and reagents via syringe. Glassware was heat-dried. Analytical thin-layer chromatography (TLC) was performed on glass-backed silica gel 60 F 254 plates (Analtech, 0.25 mm) and eluted with the appropriate solvent ratios (v/v), which are denoted where appropriate. The reactions were assayed by TLC and terminated as judged by the consumption of starting material. The tip plates were visualized using an ultraviolet (UV) lamp. Visualization can also be accomplished using stains such as ninhydrin, ammonium molybdate, iodine (12) chamber, or p-anisaldehyde spray reagent or phosphomolybdic acid reagent (Aldrich Chemical, 20 wt % in ethanol) activated with heat.

Work-ups were typically done by doubling the reaction volume with the reaction solvent or extraction solvent and then washing with the indicated aqueous solutions using 25% by volume of the extraction volume (unless otherwise indicated). Product solutions were dried over anhydrous $Na_2SO_4$ prior to filtration and evaporation of the solvents under reduced pressure on a rotary evaporator, and are noted as solvents removed in vacuo. Flash column chromatography (Still et al., *J. Org. Chem.* 43:2923 (1978)) was done using silica gel 60 (Merck Art 9385):crude material ratio of about 20:1 to 50:1 (unless otherwise indicated). Hydrogenolyses were performed at the pressures indicated in the examples or at ambient pressure.

The reaction schemes outlined below may be used to prepare the compounds of the invention. These schemes include the steps of (in various order) protection (with a protecting group $R^{32}$) of the bridgehead nitrogen which will bear the $R^1$ substituent in the final compound of formula (I-a) or (I-b), formation of the [3.3.1] or [4.3.1] azaamide nucleus, and functionalization of the piperazine or 1,4-diazaheptane ring with substituents X, or $X^1$ and $X^2$, and Y to form intermediate compounds of formula (III-a) or (V-a), respectively:

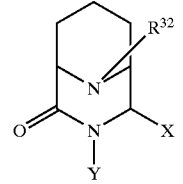
(III-a)

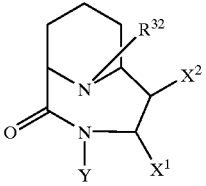
(V-a)

Such compounds of formula (III-a) and (V-a) are converted to compounds of formula (I-a) and (I-b) respectively by:
(1) removing the protecting group $R^{32}$ under suitable reducing conditions (such conditions generally being readily discernable to those skilled in the art, e.g., in light of those detailed in the examples given below) to produce a compound of formula (III-b) or (V-b); and
(2) coupling the deprotected compound of formula (III-b) or (V-b) with a reagent of formula (IV):

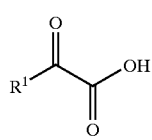
(IV)

where $R^1$ is as defined above, under suitable coupling conditions (such conditions generally being readily discernable to those skilled in the art, e.g., in light of those detailed in the examples given below);
to yield a compound of formula (I-a) or (I-b). Suitable $R^{32}$ protecting groups for nitrogen include those described below as well as others generally known to the skilled practitioner (see, e.g., Greene and Wutz, *Protecting Groups in Chemical Synthesis* (2 $^{nd}$ ed.), John Wiley & Sons, NY (1991)). In the following syntheses, $R^{32}$ is preferably the protecting group benzyloxycarbonyl, but other suitable nitrogen protecting groups may be used instead.

Scheme 1:

Scheme 1, which is depicted below, is useful for preparing Compound 7 (and other compounds by analogous methods as noted in Table 1). In Scheme 1 and in the examples below, Z is benzyloxycarbonyl. In addition to benzyloxycarbonyl, other moieties suitable for use as protecting groups for the bridgehead nitrogen may be employed (see Greene and Wutz).

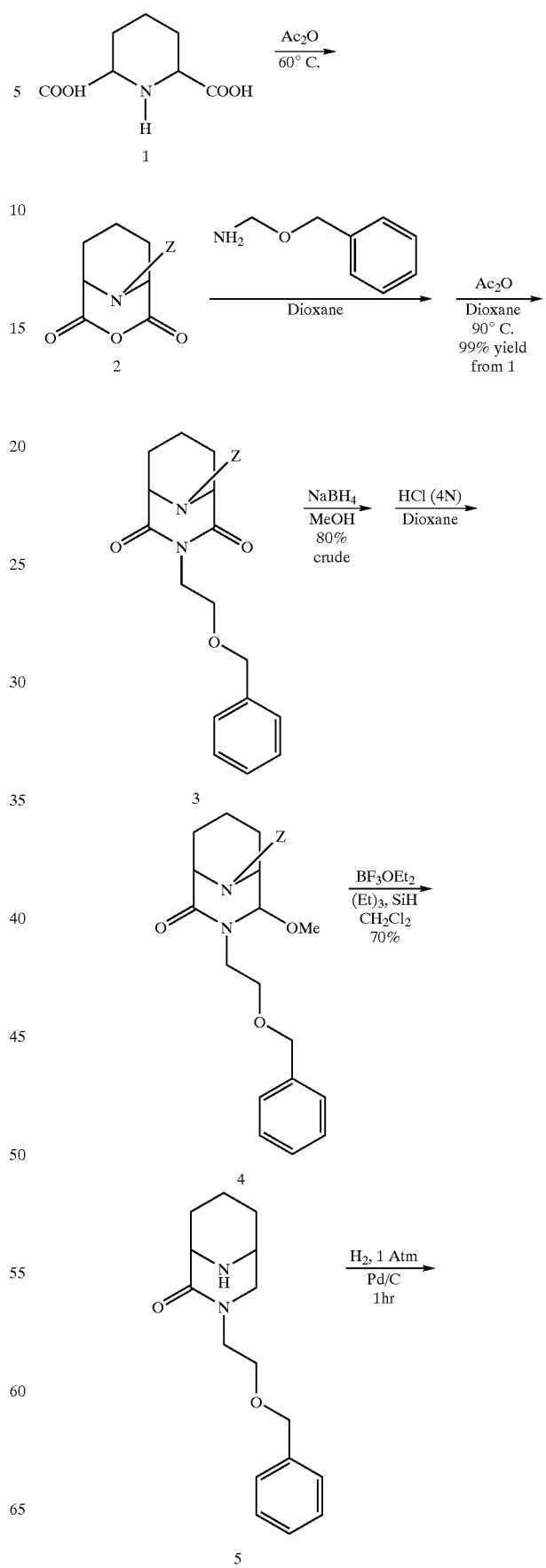

-continued

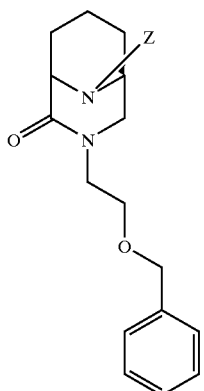

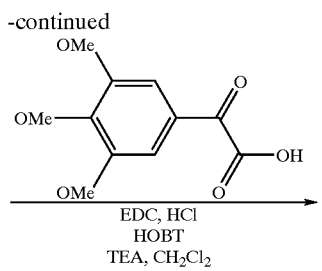

6

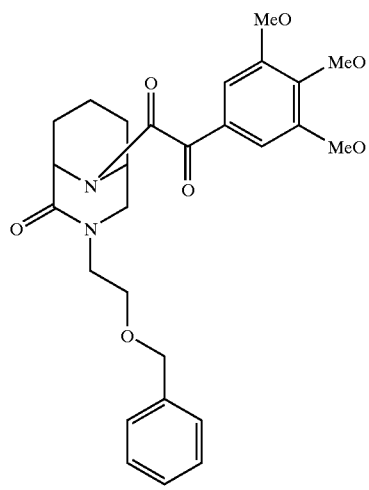

7

Piperidine-1,2,6-tricarboxylic Acid 1-Benzyl Ester (Compound 1)

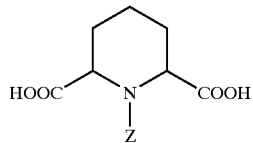

1

2,6-Pyridine dicarboxylic acid (25 g, 0.15 mol) was dissolved in 2.0M NaOH (154 mL) and H$_2$O (30 mL) at room temperature, and placed in a 500-mL Parr bottle. Rhodium on alumina powder (5%, 1.87 g) was added and the mixture was purged with argon for 15 minutes. The reaction mixture was shaken under 55 psi of hydrogen for 48 hours. The suspension was filtered through compacted Celite, and the clear filtrate was cooled to 0° C. Benzyl chloroformate (30.62 g, 0.18 mol) was added from the top to the cooled filtrate in three portions during a period of 30 minutes, and the solution was allowed to reach room temperature and stirred for additional 5 hours. The remaining benzyl chloroformate was extracted from the mixture with diethyl ether. The aqueous layer was acidified with 2N HCl and extracted with ethyl acetate (EtOAc). The EtOAc was passed over a short plug of Na$_2$SO$_4$ and evaporated. The residue was triturated with EtOAc (20 mL), and the resulting white solid was collected by vacuum filtration, washed with EtOAc (3×20 mL), and air-dried to give Compound 1 (38.3 g, 83% yield). Rf=0.06 (10% MeOH/CHCl$_3$); $^1$H NMR: δ 1.49–1.73 (m, 4H), 1.96–2.03 (m, 2H), 4.48–4.65 (m, 2H), 5.10 (s, 2H), 7.26–7.35 (m, 5H).

2,4-Dioxo-3-oxa-9-aza-bicyclo[3.3.1]nonane-9-carboxylic Acid Benzyl Ester (Compound 2)

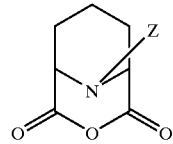

2

Piperidine-1,2,6-tricarboxylic acid 1-benzyl ester (Compound 1, 19.7 g, 64.11 mmol) was suspended in acetic anhydride (80 mL, 848 mmol) in a dry 250-mL round-bottom flask. The mixture was stirred at 70° C. for 30 minutes until a clear solution formed. The remaining acetic anhydride was removed in vacuo, to afford Compound 2 (18.5 g, 100%) as a clear oil. The material was of sufficiently good quality to be used in the next reaction without purification. The product was sensitive to water, so it was prepared for immediate use in the next step. $^1$H NMR: δ 1.57–2.01 (cm, 6H), 5.14 (s, 2H), 5.17 (s, 2H), 7.32–7.37 (m, 5H).

3-(2-Benzyloxyethyl)-2,4-dioxo-3,9-diaza-bicyclo[3.3.1]nonane-9-carboxylic Acid Benzyl Ester (Compound 3)

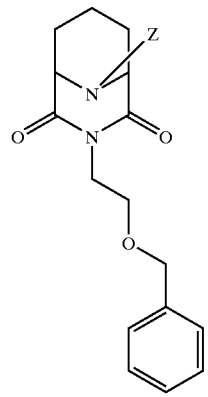

3

2,4-Dioxo-3-oxa-9-aza-bicyclo[3.3.1]nonane-9-carboxylic acid benzyl ester (Compound 2, 1.02 g, 3.52 mmol) was dissolved in dioxane (5 mL), and 2-benzyloxyethylamine (0.50 g, 3.32 mmol) was added from the top. The mixture was stirred at room temperature for 1hour (hr). Then, acetic anhydride (0.62 mL, 6.64 mmol) was added, and the reaction was refluxed for 5 hours. Dioxane was evaporated, and flash chromatographic purification of the residue (20% EtOAc/hexanes) gave Compound 3 (1.26 g, 90%) as a pale yellow oil: Rf (50% EtOAc/hexanes): 0.80.

3-(2-Benzyloxyethyl)-2-methoxy-4-oxo-3,9-diaza-bicyclo[3.3.1]nonane-9-carboxylic Acid Benzyl Ester (Compound 4)

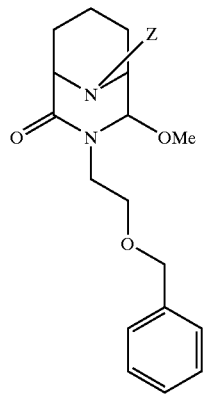

3-(2-Benzyloxyethyl)-2,4-dioxo-3,9-diaza-bicyclo[3.3.1]nonane-9-carboxylic acid benzyl ester (Compound 3, 0.46 g, 1.11 mmol) was dissolved in methanol (15 mL). The mixture was cooled to 0° C., and NaBH$_4$ (0.06 g, 1.66 mmol) was added in portions from the top. The reaction was stirred for 10 minutes at 0° C., and then 4N HCl in dioxane was added to obtain a pH in the range of 1 to 2, and the reaction was stirred overnight at room temperature. The methanol was evaporated, and the residue was dissolved in EtOAc and poured into NaHCO$_3$ saturated aqueous solution, then extracted with EtOAc (3×10 mL). The combined extracts were washed with brine (10 mL), passed over a short plug of Na$_2$SO$_4$, and the solvents were evaporated to give Compound 4 (0.40 g, 85%, mixture of isomers) as a thick pale-yellow oil, which was of sufficiently good quality to be advanced to the next step without further purification. Rf (40% EtOAc/hexanes): 0.45.

3-(2-Benzyloxyethyl)-2-oxo-3,9-diaza-bicyclo[3.3.1]nonane-9-carboxylic Acid Benzyl Ester (Compound 5)

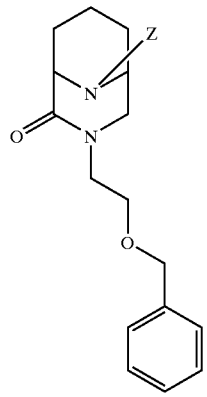

3-(2-Benzyloxyethyl)-2-methoxy-4-oxo-3,9-diaza-bicyclo[3.3.1]nonane-9-carboxylic acid benzyl ester (Compound 4, 0.34 g, 0.76 mmol) was dissolved in CH$_2$Cl$_2$ (5 mL) in a 25-ml flask under argon. BF$_3$OEt$_2$ (0.18 ml, 1.52 mmol) was added dropwise to the reaction flask (fumes were released) followed by triethylsilane (0.24 g, 1.52 mmol), and the solution was stirred overnight. The CH$_2$Cl$_2$ was evaporated and the residue was dissolved in EtOAc and washed with saturated NaHCO$_3$ (2×10 mL). The mixture was extracted with EtOAc (3×10 mL). The organic layer was dried over Na$_2$SO$_4$ and concentrated. Purification of the residue by flash column chromatography with 20% EtOAc/hexanes gave Compound 5 (0.27 g, 89%, 1:1 mixture of enantiomers) as a clear oil. Rf=0.42 (50% EtOAc/hexanes); $^1$H NMR (major rotamer): δ 1.62–1.72 (m, 6H), 3.25–3.50 (m, 2H), 3.68–3.90 (m, 5H), 4.49 (s, 2H), 4.75 (s, 1H), 5.14 (s, 2H), 7.26–7.34 (m, 10 H).

3-(2-Benzyloxy-ethyl)-3,9-diaza-bicyclo[3.3.1]nonan-2-one (Compound 6)

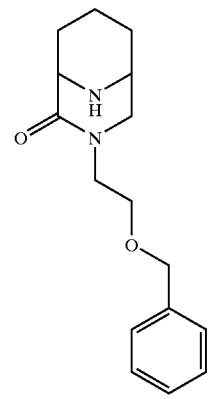

3-(2-Benzyloxyethyl)-2-oxo-3,9-diaza-bicyclo[3.3.1]nonane-9-carboxylic acid benzyl ester (Compound 5, 0.15 g, 0.36 mmol) was dissolved in MeOH (5 mL), and palladium (10%) on activated carbon (0.03 g) was added. Hydrogen was applied via balloon for 1 hour. The black suspension was then filtered through compacted Celite, and the methanol was removed by high-vacuum rotary evaporator to give Compound 6 (0.09 g, 90%) as a thick oil, which was of sufficiently good quality to be advanced to the coupling reaction without further purification.

1-[3-(2-Benzyloxyethyl)-2-oxo-3,9-diaza-bicyclo[3.3.1]non-9-yl]-2-(3,4,5-trimethoxy-ethane-1,2-dione (Compound 7)

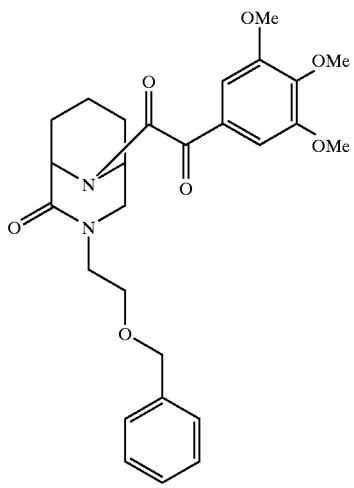

7

3-(2-Benzyloxyethyl)-3,9-diaza-bicyclo[3.3.1]nonan-2-one (Compound 6, 0.1 g, 0.36 mmol) and 2-oxo-3,4,5-trimethoxyphenylacetic acid (34.3 mg, 1.43 mmol) were dissolved in CH$_2$Cl$_2$ (5 mL), and the solution was cooled to 0° C. Hydroxybenzotriazole hydrate (HOBt, 0.06 g, 0.43 mmol) was added, followed by 1-(3-dimethylaminopropyl)-3-ethylcarbodiimide hydrochloride (EDC.HCl, 0.08, g 0.43 mmol), and triethylamine (TEA, 0.06 g, 0.43 mmol). The reaction was allowed to reach room temperature and the solution was stirred for 6 hours. The volatiles were removed with a high-vacuum rotary evaporator. The residue was dissolved in EtOAc and washed with 10% citric acid solution (10 mL), followed by water (10 mL), saturated NaHCO$_3$ (10 mL), and brine (10 mL). The combined organic layers were dried over Na$_2$SO$_4$, and were concentrated. Flash chromatographic purification of the residue (30% EtOAc/hexanes) gave Compound 7 (0.14 g, 78%) as a pale yellow oil. Rf (50% EtOAc/hexanes)=0.13; IR: 2941, 2870, 1646, 1583, 1499, 1451, 1416, 1323, 1239, 1166, 1127, 1007, 733 cm$^{-1}$; 1H NMR (major rotamer): δ 1.60–2.18 (m, 6H), 3.21–3.29 (m, 1H), 3.50 (dd, 1H, J=37, 12.5), 3.67–4.01 (m, 13H), 4.15 (s, 1H), 4.49 (s, 2H), 5.19 (s, 1H), 7.19 (d, 2H, J=8.7), 7.26–7.37 (m, 5H); HRMS (M$^+$H$^+$): expected 497.2288, observed 497.2274.

Scheme 2:

Compound 12 and the analogs shown in Table 1 may be prepared generally according to the method of Scheme 2. In this synthesis scheme, Z is benzyloxycarbonyl (e.g., in Compounds 8, 9, and 10). In addition to benzyloxycarbonyl, other moieties suitable for use as protecting groups for the bridgehead nitrogen may be employed.

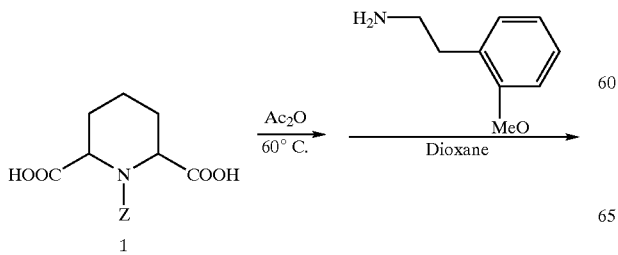

1

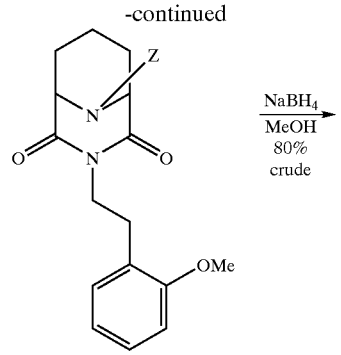

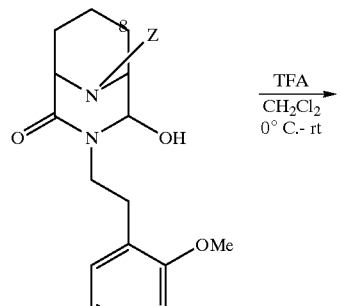

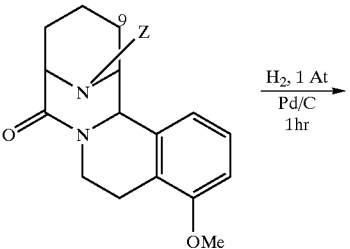

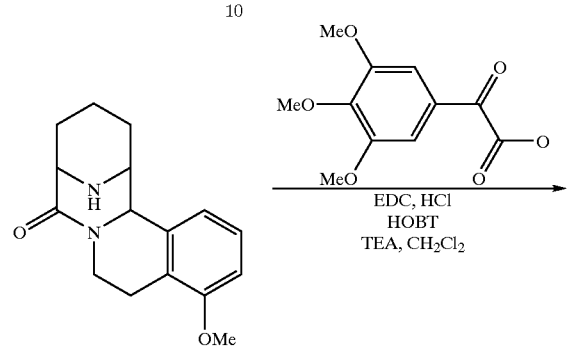

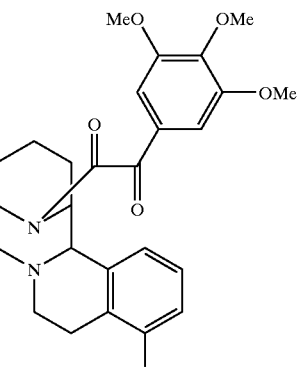

12

3-[2-(2-Methoxyphenyl)-ethyl]-2,4-dioxo-3,9-diaza-bicyclo[3.3.1]nonane-9-carboxylic Acid Benzyl Ester (Compound 8)

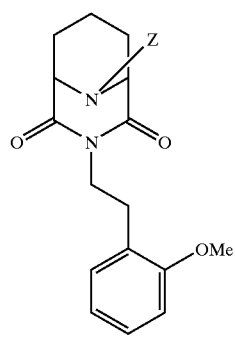

2,4-Dioxo-3-oxa-9-aza-bicyclo[3.3.1]nonane-9-carboxylic acid benzyl ester (Compound 2, 1.00 g, 3.45 mmol), which was prepared from Compound 1, was dissolved in dioxane (1 mL), and 2-methoxyphenethylamine (0.50 mL, 3.45 mmol) was added from the top. The mixture was stirred at room temperature for 1 hour. After this time, acetic anhydride (0.65 mL, 6.9 mmol) was added, and the reaction was refluxed for 5 hours. Flash chromatographic purification of the residue (20% EtOAc/hexanes) gave Compound 8 (1.23 g, 90% yield) as a clear oil. Rf=0.75 (50% EtOAc/hexanes), 0.66; $^1$H NMR: δ 1.75–2.05 (m, 6H), 2.84–2.89 (m, 2H), 3.83 (s, 3H), 4.04–4.10 (m, 2H), 4.90 (brs, 2H), 5.16 (s, 2H), 6.78–6.83 (m, 2H), 7.05 (dd, 1H, J=7.5, 1.6), 7.13–7.20 (m, 1H), 7.33–7.41 (m, 5H).

2-Hydroxy-3-[2-(2-methoxy-phenyl)-ethyl]-4-oxo-3,9-diaza-bicyclo[3.3.1]nonane-9-carboxylic Acid Benzyl Ester (Compound 9)

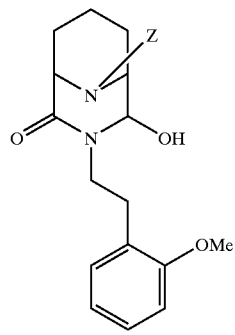

3-[2-(2-Methoxy-phenyl)-ethyl]-2,4-dioxo-3,9-diaza-bicyclo[3.3.1]nonane-9-carboxylic acid benzyl ester (Compound 8, 0.77g, 1.82 mmol) was dissolved in methanol (18 mL). The mixture was cooled to 0° C., and NaBH$_4$ (0.14 g, 3.64 mmol) was added in portions from the top. The reaction was stirred for 10 minutes and then carefully quenched with water. MeOH was removed under reduced pressure, and the residue was extracted with EtOAc. The combined organic layers were washed with 10% citric acid (5 mL), water (5 mL), saturated NaHCO$_3$ (5 mL), and brine (5 mL), and finally passed over a short plug of Na$_2$SO$_4$. The solvents were evaporated to give Compound 9 (0.65 g, 83%, mixture of isomers) as a clear oil, which was of sufficiently good quality to be advanced to the next step without further purification. Rf=0.5 (50% EtOAc/hexanes).

Compound 10

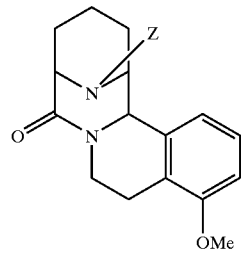

2-Hydroxy-3-[2-(2-methoxy-phenyl)-ethyl]-4-oxo-3,9-diaza-bicyclo[3.3.1]nonane-9-carboxylic acid benzyl ester (Compound 9, 0.65 g, 1.52 mmol) was dissolved in CH$_2$Cl$_2$ (1 mL) and cooled to 0° C. Trifluoroacetic acid (TFA, 0.59 mL, 7.64 mmol) was added, and the reaction was stirred at 23° C. overnight. The solvent was removed under reduced pressure, and the residue was dissolved in EtOAc (10 mL) and washed with NaHCO$_3$ (10 mL) and brine (10 mL). The organic layer was dried over Na$_2$SO$_4$ and concentrated. The residue was purified by flash column chromatography (40% EtOAc in hexanes) to afford Compound 10 (0.54 g, 87%, single diastereomer) as a clear oil. Rf=0.30 (50% EtOAc/hexanes); $^1$H NMR: δ 1.69–2.06 (m, 6H), 2.72–3.10 (m, 3H), 3.83 (s, 3H), 4.55–5.27 (m, 6H), 6.73–6.85 (m, 2H), 7.03–7.34 (m, 6H).

Compound 11

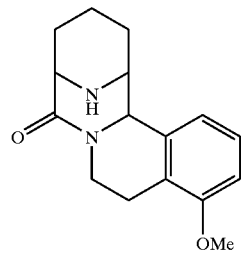

Adduct 10 (0.26 g, 0.64 mmol) was dissolved in MeOH (5 mL), and palladium (10%) on activated carbon (0.05 g) was added. Hydrogen was applied via balloon for 1 hour. The black suspension was then filtered through compacted Celite, and the methanol was removed by high-vacuum rotary evaporator to give Compound 11 (0.13 g, 76%) as a thick oil, which was of sufficiently good quality to be advanced to the next step without further purification.

Compound 12

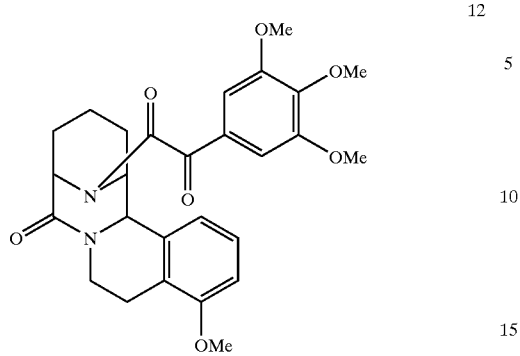

Adduct 11 (0.13 g, 0.48 mmol) and 2-oxo-3,4,5-trimethoxyphenyl acetic acid (0.14 g, 0.57 mmol) were dissolved in $CH_2Cl_2$ (5 mL), and the solution was cooled to 0° C. HOBt (0.08 g, 0.57 mmol) was added, followed by EDC.HCl (0.11 g, 0.57 mmol) and TEA (0.08 mL, 0.57 mmol). The reaction was allowed to reach room temperature and the solution was stirred for 6 hours. The volatiles were removed under reduced pressure, the residue was dissolved in EtOAc and washed with 10% citric acid solution (10 mL), followed by water (10 mL), saturated aqueous $NaHCO_3$ (10 mL), and brine (10 mL). The combined organic layers were dried over $Na_2SO_4$, and were then concentrated. Flash chromatographic purification of the residue (30% EtOAc/hexanes) gave Compound 12 as a yellow oil (0.19 g, 83%). Rf=0.42 (50% EtOAc/hexanes); IR: 2941, 2838, 1645, 1584, 1502, 1453, 1329, 1265, 1164, 1128, 1074, 1003, 734 $cm^{-1}$; $^1H$ NMR (major rotamer): δ 1.89–2.19 (m, 6H), 2.70–3.20 (m, 2H), 3.52 (s, 3H), 3.68–3.90 (m, 9H), 4.56–4.67 (m, 2H), 4.94–5.01 (m, 1H), 5.21 (s, 1H), 5.75 (s, 1H), 6.23 (d, 1H, J=7.5), 6.36–6.46 (m, 1H), 6.66 (s, 1H), 6.80 (s, 1H), 7.26–7.31 (m, 1H); HRMS ($M^+Na^+$): expected 517.1951, observed 517.1951.

Scheme 3:

Compounds such as Compound 15 below and other related compounds as shown in Table 1 may be prepared by the general method of Scheme 3, where Z is a suitable protecting group for nitrogen, such as benzyloxycarbonyl.

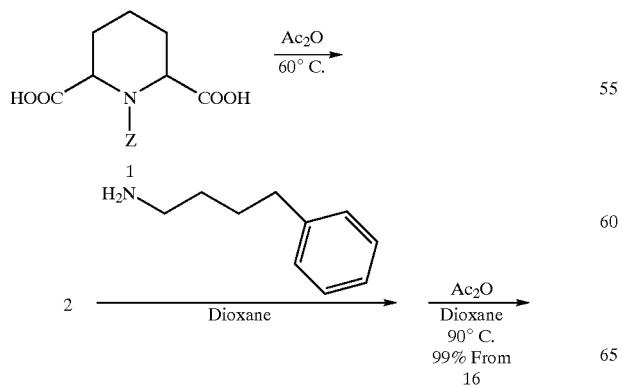

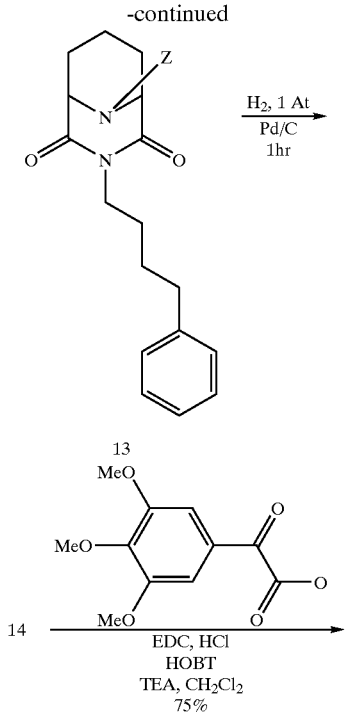

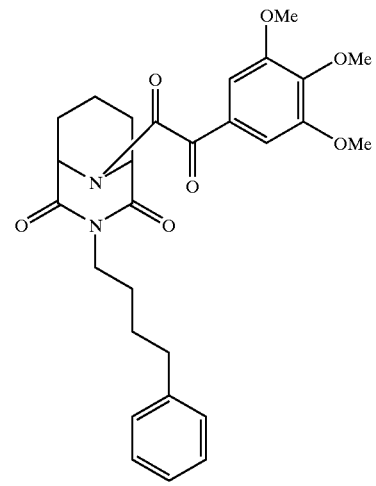

2,4-Dioxo-3-(4-phenylbutyl)-3,9-diaza-bicyclo[3.3.1]nonane-9-carboxylic Acid Benzyl Ester (Compound 13)

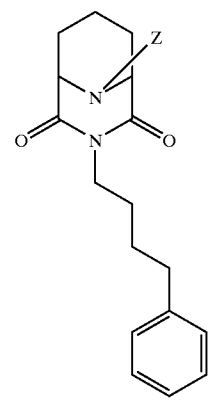

[3.3.1]Anhydride 2 (0.54 g, 1.89 mmol, prepared from Compound 1) was dissolved in 1 mL of dioxane. 4-Phenylbutylamine (0.28 g, 1.89 mmol) was added from the top. The mixture was stirred at room temperature for 1 hour. After this time, acetic anhydride (0.62 mL, 3.78 mmol) was added, and the reaction was refluxed for 5 hours. The dioxane was evaporated, and flash chromatographic purification of the residue (40% EtOAc/hexanes) gave Compound 13 (0.75 g, 95% yield) as a colorless thick oil. Rf=0.66 (40% EtOAc/hexanes); IR: 2935, 2863, 1710, 1688, 1430, 1341, 1311, 1256, 1126, 1096, 1069, 749, 699 cm$^{-1}$; $^1$H NMR: δ 1.41–2.04 (m, 8H), 2.61 (t, 2H, J=6.9), 3.79 (t, 2H, J=6.9), 4.96 (s, 2H), 5.14 (s, 2H), 7.14–7.37 (m, 10H).

3-(4-Phenylbutyl)-3,9-diaza-bicyclo[3.3.1]nonane-2,4-dione (Compound 14)

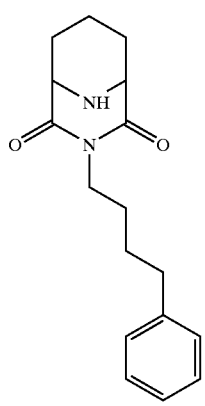

2,4-Dioxo-3-(4-phenylbutyl)-3,9-diaza-bicyclo[3.3.1]nonane-9-carboxylic acid benzyl ester (Compound 13, 0.57 g, 1.36 mmol) was dissolved in THF (3 mL), and 10% palladium on activated carbon (0.12 g) was added. Hydrogen was applied via balloon for 1 hour. The black suspension was then filtered through compacted Celite, and the THF was removed by high-vacuum rotary evaporator to give Compound 14 (0.36 g, 92%) as a thick oil, which was of sufficiently good quality to be advanced to the next step without further purification.

9-[Oxo-(3,4,5-trimethoxyphenyl)-acetyl]-3-(4-phenyl-butyl)-3,9-diaza-bicyclo[3.3.1]nonane-2,4-dione (Compound 15)

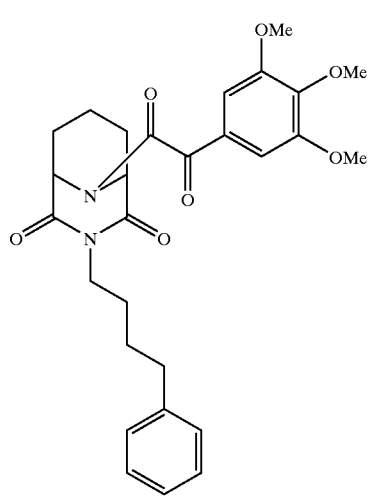

3-(4-Phenylbutyl)-3,9-diaza-bicyclo[3.3.1]nonane-2,4-dione (Compound 14, 0.42 g, 1.47 mmol) and 2-oxo-3,4,5-trimethoxyphenylacetic acid (0.35 g, 1.47 mmol) were dissolved in CH$_2$Cl$_2$ (5 mL), and the solution was cooled to 0° C. HOBt (0.21 g, 1.54 mmol) was added, followed by EDC.HCl (0.30 g, 1.54 mmol) and TEA (0.15 g, 1.47 mmol). The reaction was allowed to reach room temperature and stirred for 5 hours. The volatiles were removed using a high-vacuum rotary evaporator. The residue was dissolved in EtOAc and washed with 10% citric acid solution (10 mL), followed by water (10 mL), saturated NaHCO$_3$ (10 mL), and brine (10 mL). The combined organic layers were dried over Na$_2$SO$_4$ and were concentrated. Flash chromatographic purification of the residue (30% EtOAc/hexanes) gave Compound 15 as a pale-yellow solid (0.25 g, 34%, one isomer). mp=101–103° C.; Rf=0.32 (50% EtOAc/hexanes); IR: 2939, 2866, 1739, 1682, 1651, 1582, 1503, 1454, 1416, 1361, 1337, 1243, 1167, 1126, 1067, 991, 914, 862 cm$^{-1}$; 1H NMR (major rotamer): δ 1.56–1.64 (m, 5H), 1.93–2.01 (m, 5H), 2.61–2.66 (m, 2H), 3.80–3.85 (m, 2H), 3.95 (s, 9H), 4.51 (brs, 1H), 5.46 (brs, 1H),7.14–7.29 (m, 7H); HRMS (M$^+$H$^+$): expected 509.2288, observed 509.2275; EA: calculated, C (66.13), H (6.34), N (5.51); found, C (66.00, H (6.37), N (5.50).

Scheme 4:

Scheme 4 is useful for preparing compounds of the formula 18 and similar compounds as listed in Table 1 (e.g., by varying the arylmethylbromide reagent used in the first step).

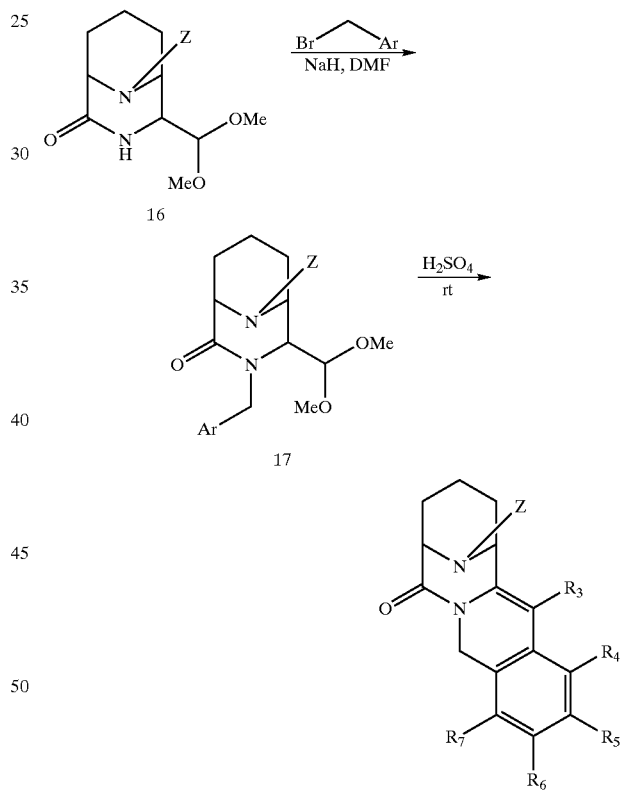

In formula 18, R$_3$, R$_4$, R$_5$, R$_6$, and R$_7$ are each independently H or any suitable substituent linked to the ring nuclei through O, N, C, or S. Z in the formulae above is a protecting group, such as benzyloxycarbonyl.

Compound 16 is reacted with an aryl-substituted bromomethane in the presence of sodium hydride and DMF to give Compound 17. Compound 17 is then reacted with sulfuric acid to produce a compound of the formula 18. Compounds of formula 18 are converted to compounds of formula (I-a) by removing protecting group Z and coupling the resulting product with a compound of formula (IV).

Scheme 5
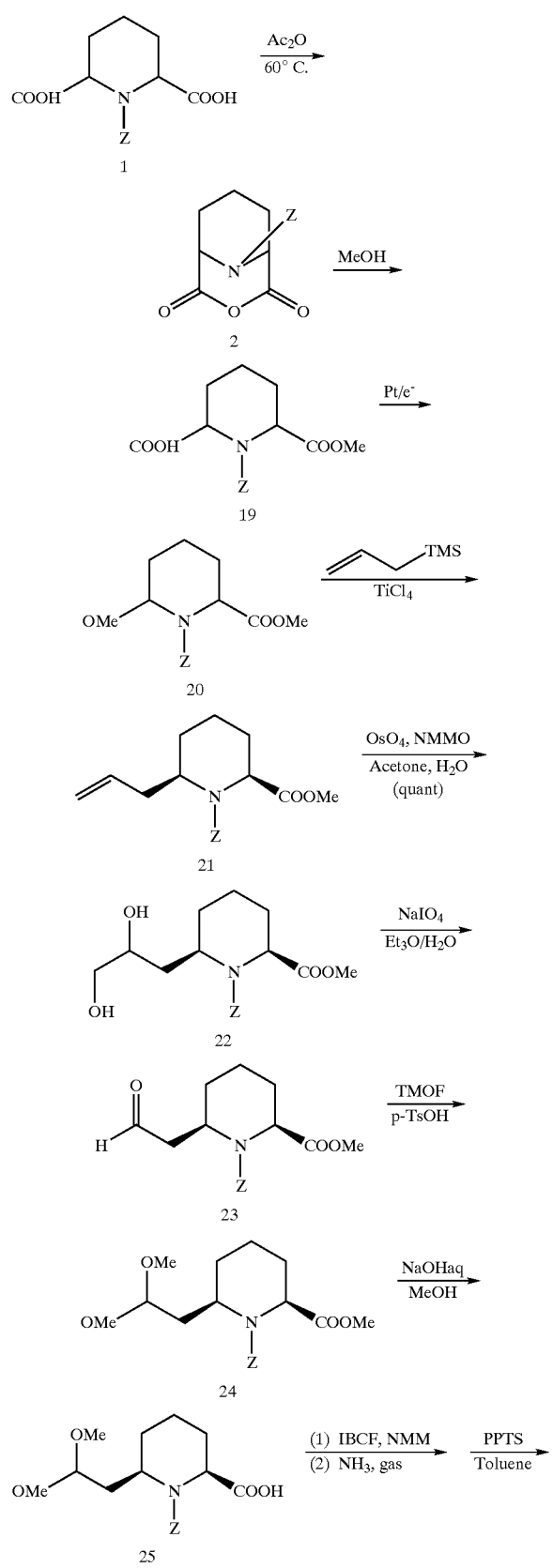
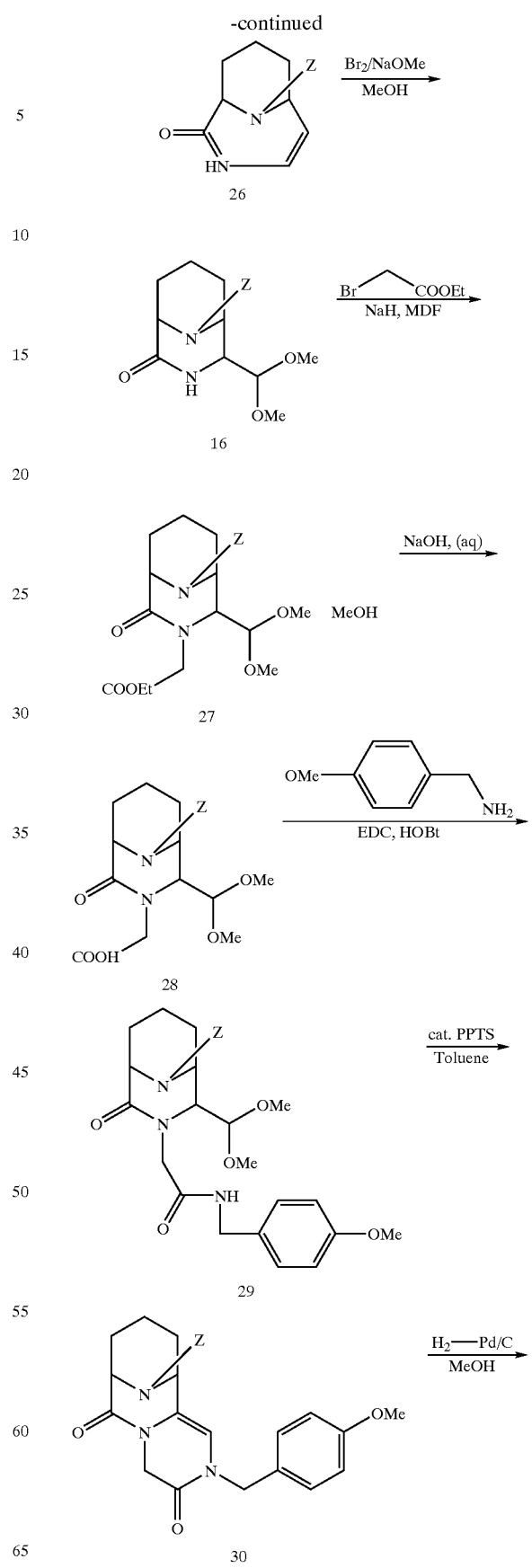

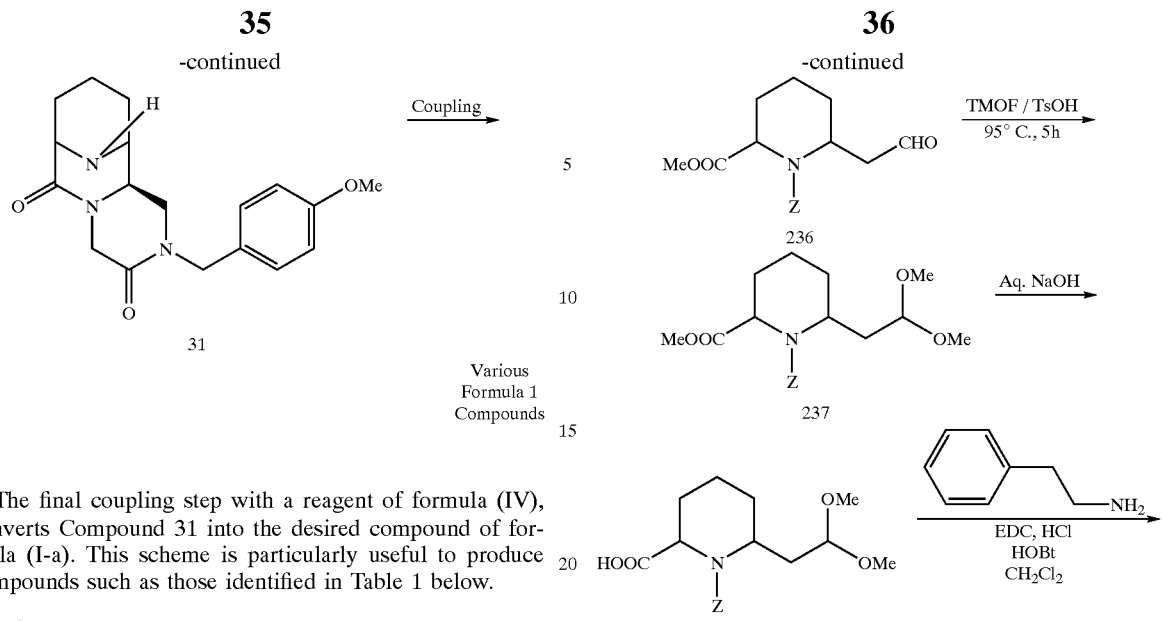

Various Formula 1 Compounds

The final coupling step with a reagent of formula (IV), converts Compound 31 into the desired compound of formula (I-a). This scheme is particularly useful to produce compounds such as those identified in Table 1 below.

Scheme 6:

Scheme 6 is useful for preparing Compound 159 and other related compounds as shown in Table 1.

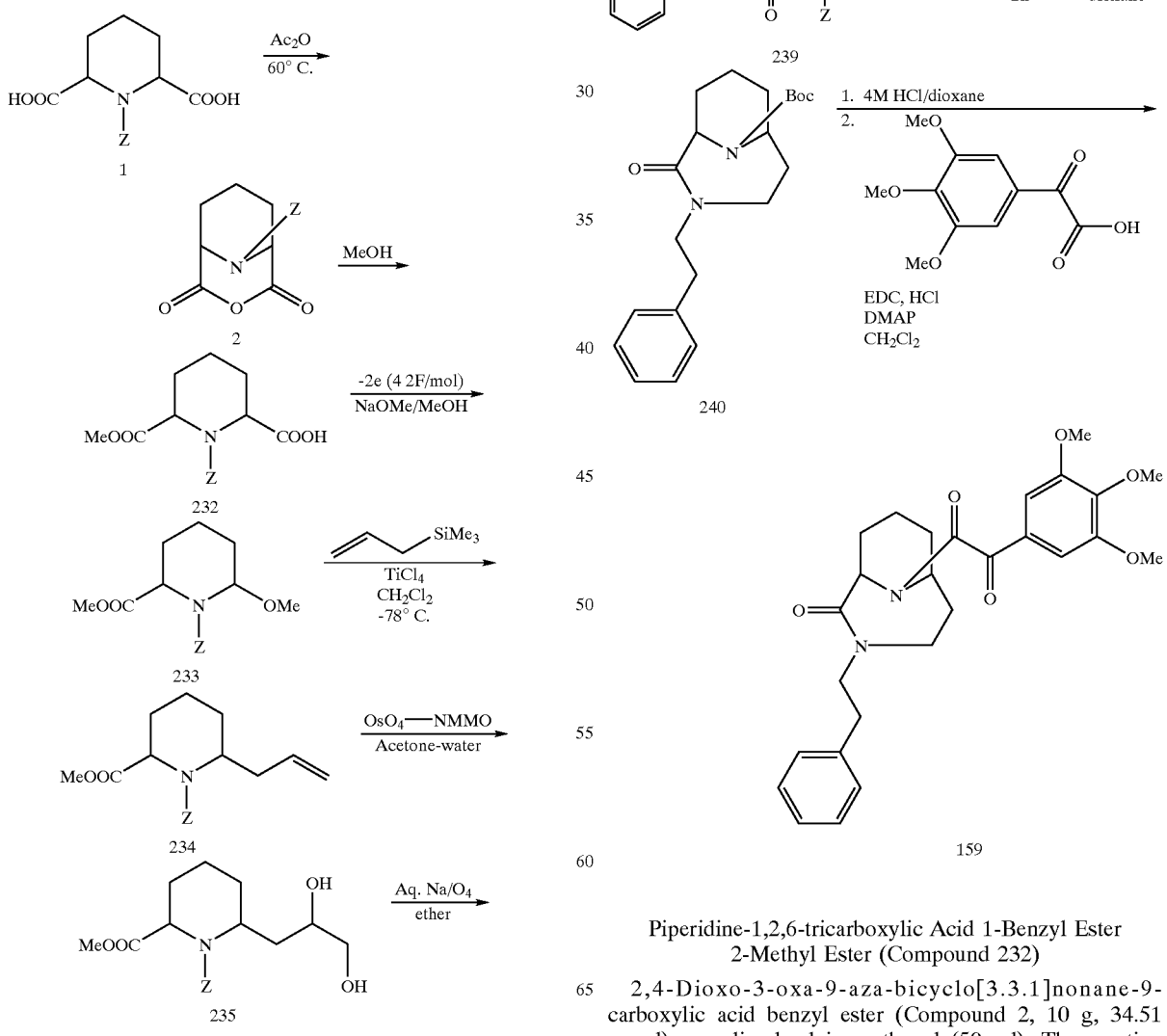

Piperidine-1,2,6-tricarboxylic Acid 1-Benzyl Ester 2-Methyl Ester (Compound 232)

2,4-Dioxo-3-oxa-9-aza-bicyclo[3.3.1]nonane-9-carboxylic acid benzyl ester (Compound 2, 10 g, 34.51 mmol) was dissolved in methanol (50 ml). The reaction mixture was stirred at room temperature for 2 hours. The MeOH was evaporated to afford Compound 232 (10 g, 96%). Rf=0.47 (10% MeOH/CH$_2$Cl$_2$). The material was of sufficiently good quality to be used in the next reaction without purification.

6-Methoxy-piperidine-1,2-dicarboxylic Acid 1-Benzyl Ester 2-Methyl Ester (Compound 233)

6-Methoxy-piperidine-1,2-dicarboxylic acid 1-benzyl ester 2-methyl ester (Compound 232, 10g, 31.15 mmol) was dissolved in methanol (80 ml). 1M Sodium methoxide solution in methanol (20 ml) was added. A constant current (using platinum electrodes) of 0.3 A was applied for 1.96 hours, using a total of 4.17 F/mol. The methanol was evaporated. Flash chromatographic purification of the residue (1:2 EtOAc/hexanes) gave Compound 233 (9.14 g, 95%). Rf=0.9 (10% MeOH/CH$_2$Cl$_2$).

6-Allyl-piperidine-1,2-dicarboxylic Acid 1-Benzyl Ester 2-Methyl Ester (Compound 234)

6-Methoxy-piperidine-1,2-dicarboxylic acid 1-benzyl ester 2-methyl ester (Compound 233, 1.04 g, 3.39 mmol) was dissolved in CH$_2$Cl$_2$ (10 mL), and the solution was cooled to −78° C. using dry ice-acetone bath. 1M TiCl$_4$ solution in CH$_2$Cl$_2$ (3.7 mL) was added dropwise over a 1-minute period, followed by allyltrimethylsilane (1.61 mL, 10.14 mmol). The bath was changed to water, and the reaction mixture was stirred for 2 hours. The reaction mixture was poured into brine (50 ml) and extracted with CHCl$_3$ (2×50 mL). The combined organic layers were washed with saturated NaHCO$_3$ solution (50 mL) and finally dried over Na$_2$SO$_4$. The solvent was evaporated and the residue was purified by flash chromatography (1:5 EtOAc/hexanes) to give Compound 234 (0.91 g, 84%). Rf=0.78 (1:2 EtOAc/hexanes).

6-(2,3-Dihydroxy-propyl)-piperidine-1,2-dicarboxylic Acid 1-Benzyl Ester 2-Methyl Ester (Compound 235)

6-Allyl-piperidine-1,2-dicarboxylic acid 1-benzyl ester 2-methyl ester (Compound 234, 0.087 g, 0.2 mmol) was dissolved in acetone (2 mL) and water (0.25 mL). N-Methylmorpholine oxide (0.068 g, 0.58 mmol) was added, followed by a 2.5% OsO4 solution in t-BuOH (0.14 mL). The mixture reaction was stirred at room temperature for 14 hours. Sodium pyrosulfate (0.3 g) in water (1 mL) was added with stirring, and the resultant solution was filtered through Celite and washed with ethanol (10 mL). The solvents were removed and the residue was purified by flash column chromatography (100% EtOAc) to afford Compound 235 (0.086 g, 89%, as a mixture of isomers). Rf=0.12 and 0.06 (2:1 EtOAc/hexanes).

6-(2-Oxo-ethyl)-piperidine-1,2-Dicarboxylic Acid 1-Benzyl Ester 2-Methyl Ester (Compound 236)

6-(2,3-Dihydroxy-propyl)-piperidine-1,2-dicarboxylic acid 1-benzyl ester 2-methyl ester (Compound 235, 0.614 g, 1.75 mmol) was dissolved in Et$_2$O (20 mL) and cooled to 0° C. Ten percent NaIO$_4$ aqueous solution (4 mL) was added, and the reaction was stirred for 1 hour. The reaction mixture was poured into brine (15 mL) and extracted with Et$_2$O (3×20 mL). The combined organic layer was further washed with aqueous NaS2O$_3$ (10 mL), NaHCO$_3$ saturated solution (10 mL), brine (10 mL) and finally dried over MgSO$_4$. The solvents were removed to afford Compound 236 (0.53 g, 95%). Rf=0.67 (1:1 EtOAc/hexanes). The material was of sufficiently good quality to be used in the next reaction without purification.

6-(2,2-Dimethoxy-ethyl)-piperidine-1,2-dicarboxylic Acid 1-Benzyl Ester 2-Methyl Ester (Compound 237)

6-(2-Oxo-ethyl)-piperidine-1,2-dicarboxylic acid 1-benzyl ester 2-methyl ester (Compound 236, 0.4 g, 1.25 mmol), trimethyl orthoformate (5 mL) and p-toluenesulfonic acid monohydrate (0.03 g) were combined, and the reaction mixture was stirred at room temperature for 12 hours. Aqueous NaHCO$_3$ (25 mL) was added and the reaction was extracted with CHCl$_3$ (3×100 mL). The combined organic layer was dried over MgSO$_4$ and concentrated. The residue was purified by flash chromatography (1:2 EtOAc/hexanes) to afford Compound 237 (0.441 g, 96%). Rf=0.75 (1:1 EtOAc/hexanes).

2-(2,2-Dimethoxy-ethyl)-6-phenethylcarbamoyl-piperidine-1-carboxylic Acid Benzyl Ester (Compound 239)

6-(2,2-Dimethoxy-ethyl)-piperidine-1,2-dicarboxylic acid 1-benzyl ester 2-methyl ester (Compound 237, 0.350 g, 0.96 mmol) was dissolved in methanol (5 ml) and 2N NaOH (4 mL). The reaction was stirred at room temperature for 8 hours. The methanol was evaporated, and the residue was dissolved in Et$_2$O and washed with 5% KHSO$_4$ (10 mL), brine (10 mL), dried over Na$_2$SO$_4$ and concentrated, to afford Compound 238 (0.335 g, 0.96 mmol), which was used in the next reaction without further purification.

6-(2,2-Dimethoxy-ethyl)-piperidine-1,2-dicarboxylic acid 1-benzyl ester (Compound 238, 0.335 g, 0.96 mmol) and phenethyl amine (0.14 g, 1.15 mmol) were dissolved CH$_2$Cl$_2$ (20 mL). HOBt (0.156 g, 1.15 mmol) was added followed by EDC.HCl (0.221 g, 1.15 mmol). The reaction was stirred at room temperature for 18 hours. Saturated NaHCO$_3$ solution (25 mL) was added and then extracted with CHCl$_3$ (2×50 mL). The combined organic layers were dried over Na$_2$SO$_4$, and then concentrated. Flash chromatographic purification of the residue (1:1 EtOAc/hexanes) gave Compound 239 (0.374 g, 86%). Rf=0.47 (1:1 EtOAC/hexanes).

2-Oxo-3-phenethyl-3,10-diaza-bicyclo[4.3.1]decane-10-carboxylic Acid tert-Butyl Ester (Compound 240)

2-(2,2-Dimethoxy-ethyl)-6-phenethylcarbamoyl-piperidine-1-carboxylic acid benzyl ester (Compound 239, 0.297g, 0.65mmol) was dissolved in toluene (15 ml), and the flask was immersed in a 80° C. oil bath. Pyridinium p-toluene sulfonate (0.0120 g, 0.05 mmol) was added and the reaction was stirred at 80° C. for 2 hours. After this time, the reaction was cooled down and the precipitate formed was removed by filtration. The toluene was evaporated and the residue was dissolved in dioxane (10 mL). N-(tert-Butoxycarbonyl anhydride (0.285 g, 1.31 mmol) and palladium 10% on activated carbon (0.1 g) were added. Hydrogen was applied via Parr apparatus and reaction was shaken at 50 psi for 12 hours. The black suspension was then filtered through compacted Celite, and dioxane was removed. Flash chromatographic purification of the residue (1:2 EtOAc/hexanes) gave Compound 240 (0.211 g, 90%). Rf=0.31 (1:2 EtOAc/hexanes).

1-(2-Oxo-3-phenethyl-3,10-diaza-bicyclo[4.3.1]dec-10-yl)-2-(3,4,5-trimethoxy-phenyl)-ethane-1,2-dione (Compound 159)

2-Oxo-3-phenethyl-3,10-diaza-bicyclo[4.3.1]decane-10-carboxylic acid tert-butyl ester (Compound 240, 0.204 g, 0.56 mmol) was dissolved in 4M HCl in dioxane (3 mL), and the solution was stirred at room temperature for 1 hour. The solvent was removed and the residue was dissolved in CHCl₃ (50 mL), washed with saturated NaHCO₃ solution, dried over NaSO₄ and concentrated to afford a white solid (0.142 g, 0.55 mmol), which was dissolved in CH₂CL₂ (10 mL). 3,3-Dimethyl-2-oxo-pentanoic acid (0.131 g, 0.54 mmol), EDC.HCl (0.126 g, 0.66 mmol) and 4-DMAP (0.081 g, 0.66 mmol) were added, and the reaction was stirred at room temperature for 18 hours. The volatiles were removed at a high-vacuum evaporator, and the residue was dissolved in EtOAC and washed with water (10 mL), 1N HCl solution (20 mL), saturated NaHCO₃ (20 mL) and brine (20 mL). The combined organic layers were dried over Na₂SO₄, and were concentrated. Flash chromatographic purification of the residue (2:1 EtOAc/hexanes) gave final Compound 159 (0.120 g, 45% yield). Rf=0.4 (2:1 EtOAC/hexanes).

Scheme 7:

Compound 162 and like compounds may be prepared as described below.

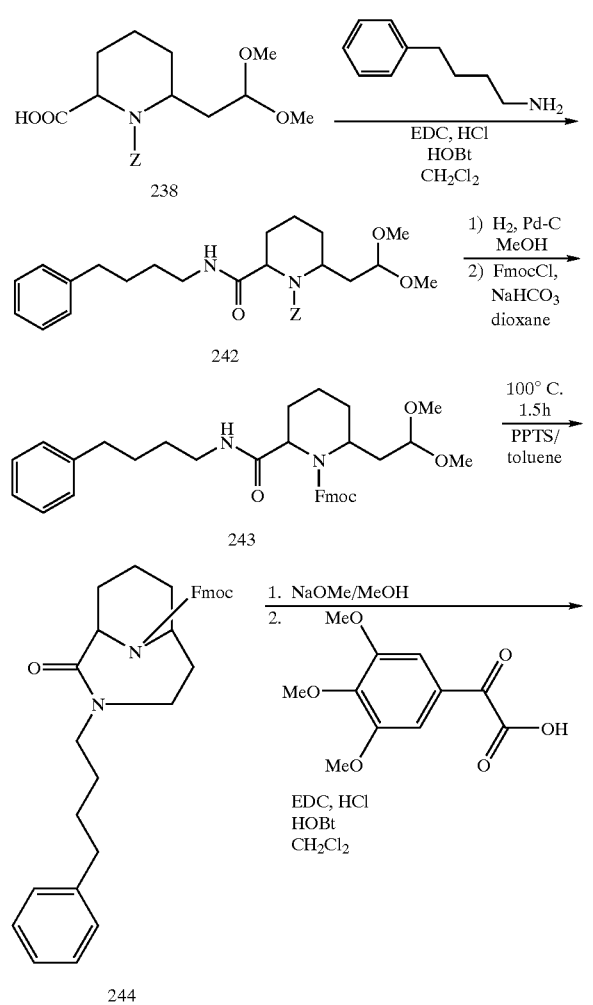

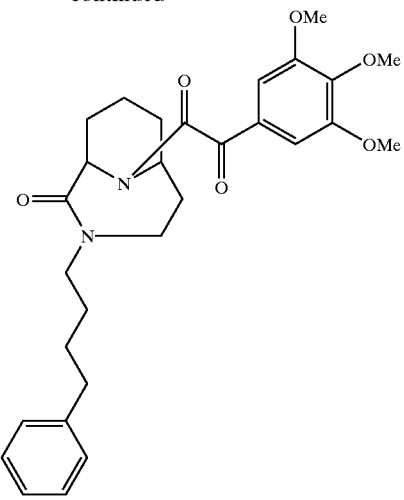

162

2-(2,2-Dimethoxy-ethyl)-6-(4-phenyl-butylcarbamoyl)-piperidine-1-carboxylic Acid Benzyl Ester (Compound 242)

6-(2,2-Dimethoxy-ethyl)-piperidine-1,2-dicarboxylic acid 1-benzyl ester (Compound 238, 1 g, 2.85 mmol) and 4-phenylbutyl amine (0.51 g, 3.42 mmol) were dissolved in CH₂Cl₂ (60 mL). HOBt (0.462 g, 3.42 mmol) was added followed by EDC.HCl (0.655 g, 3.42 mmol). The reaction was stirred at room temperature for 12 hours. Saturated NaHCO₃ (25 mL) was added and the reaction was extracted with CHCl₃ (2×50 mL). The combined organic layers were dried over Na₂SO₄, and then concentrated. Flash chromatographic purification of the residue (1:1 EtOAc/hexanes) gave Compound 242 (1.294 g, 94%). Rf=0.62 (1:1 EtOAC/hexanes).

2-(2,2-Dimethoxy-ethyl)-6-(4-phenyl-butylcarbamoyl)-piperidine-1-carboxylic Acid 9H-fluoren-9-ylmethyl Ester (Compound 243)

2-(2,2-Dimethoxy-ethyl)-6-(4-phenyl-butylcarbamoyl)-piperidine-1-carboxylic acid benzyl ester (Compound 242, 0.887 g, 1.83 mmol) was dissolved in methanol (50 mL). Palladium (10%) on activated carbon (0.09 g) was added. Hydrogen was applied via Parr apparatus, and the reaction was shaken at 50 psi for 15 hours. The black suspension was then filtered through compacted Celite, and methanol was removed. The residue was dissolved in dioxane (25 mL). 9-Fluorenylmethyl chloroformate (0.473 g, 1.83 mmol) was added, followed by NaHCO₃ (0.307 g, 3.66 mmol) dissolved in water (7 mL). The reaction was stirred at room temperature for 10 hours, poured into ice and 5% KHSO₄ solution, and then extracted with CHCl₃ (2×100 mL). Flash chromatographic purification of the residue (1:2 EtOAc/hexanes) gave Compound 243 (1.050 g, 100%). Rf=0.59 (1:1 EtOAc/hexanes).

2-Oxo-3-(4-phenyl-butyl)-3,10-diaza-bicyclo[4.3.1] dec-4-ene-10-carboxylic Acid 9H-Fluoren-9-ylmethyl Ester (Compound 244)

2-(2,2-Dimethoxy-ethyl)-6-(4-phenyl-butylcarbamoyl)-piperidine-1-carboxylic acid 9H-fluoren-9-ylmethyl ester (Compound 243, 1 g, 1.75 mmol) was dissolved in toluene (25 ml). Pyridinium p-toluene sulfonate (0.02 g, 0.08 mmol) was added and the reaction was stirred at 100° C. for 2 hours. After this time the reaction was cooled down, the toluene was evaporated and the residue was dissolved in EtOAc (75 mL), washed with saturated NaHCO$_3$ solution (25 mL) and dried over Na$_2$SO$_4$. Flash chromatographic purification of the residue (1:2 EtOAc/hexanes) gave Compound 244 (0.770 g, 87%). Rf=0.5 (1:2 EtOAc/hexanes).

1-[2-Oxo-3-(4-phenyl-butyl)-3,10-diaza-bicyclo [4.3.1]dec-4-en-10-yl]-2-(3,4,5-trimethoxy-phenyl)-ethane-1,2-dione (Compound 162)

2-Oxo-3-(4-phenyl-butyl)-3,10-diaza-bicyclo[4.3.1]dec-4-ene-10-arboxylic acid 9H-fluoren-9-ylmethyl ester (Compound 244, 0.740 g, 1.46 mmol) was dissolved in methanol (15 mL), and 1N NaOMe solution in methanol (2.5 mL) was added. The reaction was stirred at room temperature for 2 hours. The volatiles were removed and the product was extracted with CHCl$_3$, dried over Na$_2$SO$_4$ and concentrated to a white precipitate, which was dissolved in CHCl$_3$ (10 mL). 3,3-Dimethyl-2-oxo-pentanoic acid (0.141 g, 0.58 mmol), HOBt (0.080g, 0.58 mmol), EDC.HCl (0.113 g, 0.58 mmol), and TEA (0.082 mL, 0.58 mmol) were added, and the reaction was stirred at room temperature for 18 hours. The volatiles were removed using a high-vacuum evaporator, and the residue was dissolved in EtOAC and washed with 10% citric acid solution (10 mL), followed by water (10 mL), saturated NaHCO$_3$ (10 mL) and brine (10 mL). The combined organic layers were dried over Na$_2$SO$_4$, and were concentrated. Flash chromatographic purification of the residue (1:1 EtOAc/hexanes) gave Compound 162 (0.122 g, 50%). Rf (1:1 EtOAC/hexanes): 0.122.

Biochemical and Biological Assays

A variety of assays and techniques may be employed to determine the activities of the compounds of the present invention. The activity of a compound of the invention for stimulation of neurite outgrowth is directly related to its binding affinity for FKBP12 and its ability to inhibit FKBP12 rotamase activity. In order to quantify these latter properties, assays known in the art for measuring ligand binding and enzyme activity may be employed. Assays for stimulation of neurite outgrowth are described below.

For example, compounds may be tested to determine their neurotrophic activity using the method described by Lyons et al., *Proc. Natl. Acad. Sci.*, 91:3191–3195 (1994). In this rat pheochromocytoma assay for neurite outgrowth, PC12 rat pheochromocytoma cells are maintained at 37° C. and 5% CO$_2$ in Dulbecco's modified Eagle's medium (DMEM) supplemented with 10% heat-inactivated horse serum and 5% heat-inactivated fetal bovine serum. Cells are then plated, coated at $10^5$ per 35 mm culture well with rat tail collagen at 5 mg/cm$^2$, and allowed to attach. Medium is then replaced with DMEM supplemented with 2% horse serum, 1% fetal bovine serum, nerve growth factor (NGF), and/or varying concentrations of test compounds. The control cultures are administered NGF without any of the test compounds.

Another exemplary method that may be used for measuring potency for stimulation of neurite outgrowth is the rat dorsal root ganglia assay. In this assay, dorsal root ganglia are dissected from 16-day-old Sprague-Dawley rat embryos. The sensory ganglia are then cultured in collagen-coated 35 mm Falcon dishes with N-2 medium (DMEM/Ham's F$_{12}$, 1:1) at 37° C. in a 15% CO$_2$ environment. The medium is supplemented with selenium, progesterone, insulin, putrescine, glucose, penicillin and streptomycin. The ganglia are then treated with various concentrations of NGF (0–100 ng/ml) and test compound. The sensory ganglia are observed every two to three days under a phase contrast microscope, and the axon lengths are measured. See Lyons et al., *PNAS*, 91:3191–3195 (1994).

Other suitable assays may be used to measure the activity of the compounds of the present invention. For example, immunosuppressant activity can be estimated through measurements of the inhibition of calcineurin phosphatase activity by complexes of compounds of the invention bound to FKBP (Babine et al., *Bioorg. Med. Chem. Lett.*, 6, 385–390, 1996). The phosphopeptide phosphatase activity of calcineurin is assayed at 30° C. using a continuous coupled spectrophotometric assay (Etzkorn et al., *Biochemistry*, 32, 2380, 1994) and the phosphorylated 19-mer peptide substrate derived from the regulatory subunit ($R_{II}$) of cAMP-dependent protein kinase. The assay mixture contains 50 mM MOPS (pH 7.5), 0.1 M NaCl, 6 mM MgCl$_2$, 0.5 mg/ml bovine serum albumin, 0.5 mM dithiothreitol, 1 mM CaCl$_2$, 1 mM MnCl$_2$, 20 $\mu$M phosphorylated $R_{II}$ peptide, 20 nM human recombinant calcineurin, 40 nM calmodulin, 10 $\mu$g/mL purine ribonucleoside phosphorylase, and 200 $\mu$M methylthioguanosine as described by Etzkorn et al., plus 1% dimethylsulfoxide (DMSO) as cosolvent and 100 $\mu$M FKBP. Compounds are tested for FKBP-dependent inhibition of calcineurin at their maximum solubility. Under these conditions, the apparent inhibition constant for inhibition of human recombinant calcineurin by FKBP-FK506 is measured to be 43 nM.

Binding of compounds to FKBP may be measured directly using microcalorimetry. Calorimetric titrations are carried out using the MCS-ITC instrument (MicroCal Inc., Northhampton, Mass.). The titrations may be conducted as follows. Protein dialysate is degassed for 15 minutes using MicroCal equipment. Stock inhibitor solution is added to cosolvent (typically DMSO) and degassed dialysate, followed by brief sonication, to produce the final inhibitor solutions to be used in the titrations. Final inhibitor solutions are in the concentration range 10 to 80 $\mu$M. Dialyzed protein is added to cosolvent and degassed dialysate to produce FKBP12 solutions in the concentration range 200 to 1600 $\mu$M. As both solutions are prepared using degassed dialysate, no additional degassing of the solutions is performed. Cosolvent is added to the protein solutions to maintain a fixed cosolvent concentration throughout the course of the titration. Protein is titrated into inhibitor using a 125-$\mu$L injection syringe. The titrations are conducted with the ligand in the cell due to low solubility of inhibitors. Typically, a preliminary 2-$\mu$L injection is followed by fifteen 8-$\mu$L injections made at varying injection intervals. A full set of dilution controls is conducted for each titration. An appropriate volume of cosolvent is added to degassed dialysate to produce the buffered cosolvent solution used to obtain heats of dilution of the reactants. After correcting for the heats of dilution and deletion of the preliminary injection, the titration results are fitted using the "One Set of Sites Model" in the ORIGIN software package supplied with the instrument.

Binding to FKBP as directly measured by microcalorimetry has been found to correlate well with potency for inhibition of the rotamase reaction, which is readily assayed by methods known in the art (see, e.g., Fischer et al., *Biochim. Biophys.* Acta 791, 87 (1984); Fischer et al., *Biomed. Biochim.* Acta 43, 1101 (1984); Fischer et al., *Nature* 337, 476–478 (1989); Siekierka et al., *Nature*, 341, 755–57 (1989); U.S. Pat. No. 5,696,135; and Harding et al., *Nature*, 341, 758–60 (1989)).

In the rotamase inhibition assay, isomerization of an artificial substrate N-succinyl-Ala-Ala-Pro-Phe-p-nitroanilide is followed spectrophotometrically. The assay includes the cis form of the substrate, FKBP12, the compound being tested, and chymotrypsin. Chymotrypsin is able to cleave p-nitroaniline from the trans form of the substrate, but not from the cis form. Release of p-nitroaniline is measured spectrophotometrically. Using this assay, various amounts of the FKBP rotamase-inhibiting compounds of formula (I-a) or (I-b) were added to cis-N-succinyl-alanine-alanine-proline-phenylalanine-para-nitroaniline (Bachem, 3132 Kashiwa Street, Torrance, Calif. 90505) in the presence of FKBP12 and chymotrypsin. Spectrophotometric measurements of p-nitroaniline concentrations allowed estimation of the apparent $K_i$ values, which are provided in Table 1 below.

TABLE 1

| Compound Number | Molecular Structure | Prepn by Scheme No. | Number of Rotamase Isomers | $K_{i(app)}$ ($\mu$M) |
|---|---|---|---|---|
| 7 | 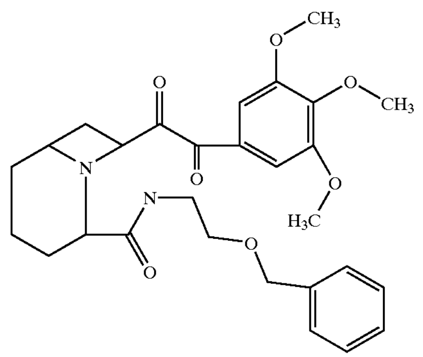 | 1 | 2 | 0.160 |
| 12 | 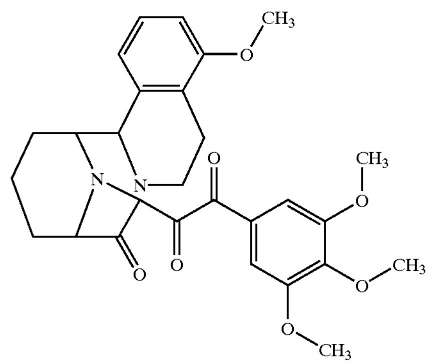 | | 2 | 0.027 |
| 32 | 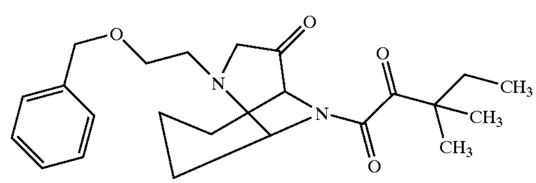 | 1 | 2 | 2.3 |
| 33 | 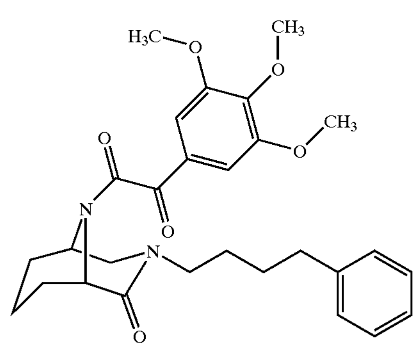 | 1 | 2 | 0.227 |

TABLE 1-continued
| Compound Number | Molecular Structure | Prepn by Scheme No. | Number of Isomers | Rotamase $K_{i(app)}$ ($\mu M$) |
|---|---|---|---|---|
| 34 | 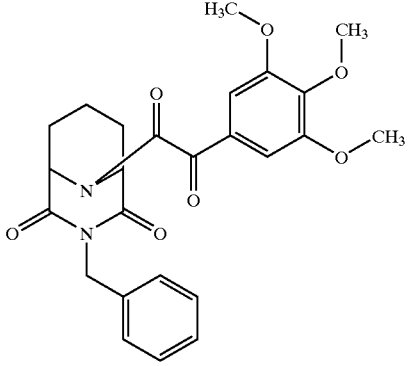 | 3 | 1 | 0.206 |
| 35 | 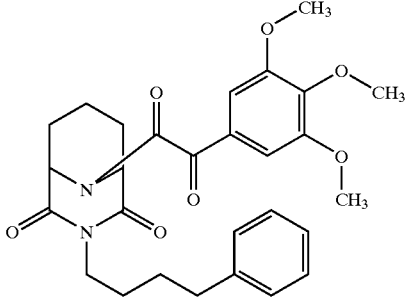 | 3 | 1 | 0.073 |
| 36 | 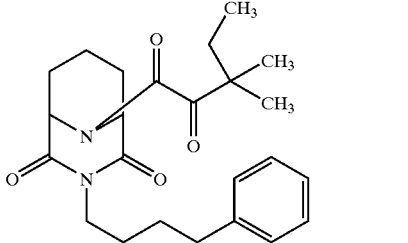 | 3 | 1 | 0.445 |
| 37 | 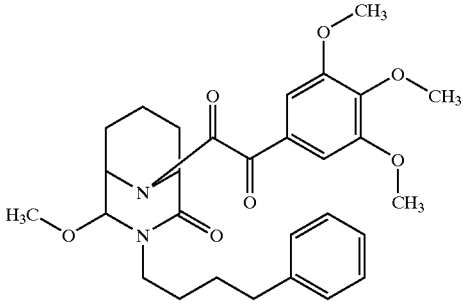 | 3 | 4 | 0.222 |

TABLE 1-continued
| Compound Number | Molecular Structure | Prepn by Scheme No. | Number of Isomers | $K_{i(app)}$ ($\mu$M) |
|---|---|---|---|---|
| 38 | 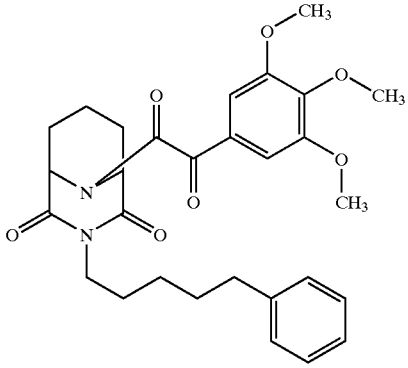 | 3 | 1 | 0.298 |
| 39 | 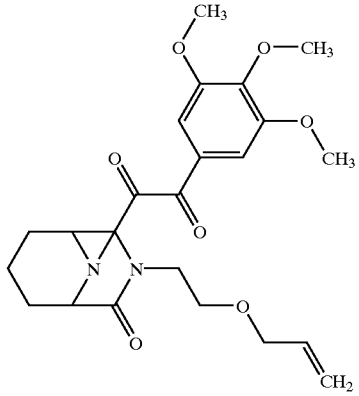 | 1 | 2 | 0.398 |
| 40 | 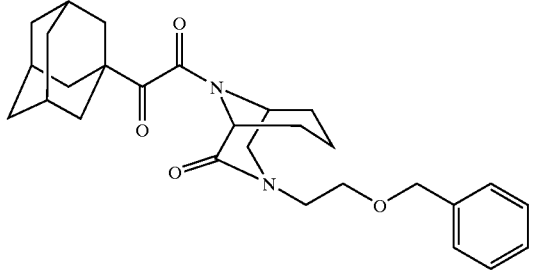 | 1 | 2 | 0.690 |
| 41 | 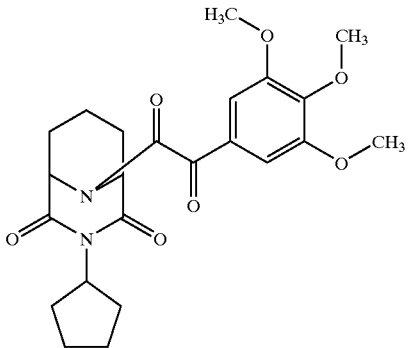 | 1 | 2 | 5.8 |

TABLE 1-continued

| Compound Number | Molecular Structure | Prepn by Scheme No. | Number of Isomers | Rotamase $K_{i(app)}$ ($\mu M$) |
|---|---|---|---|---|
| 42 | 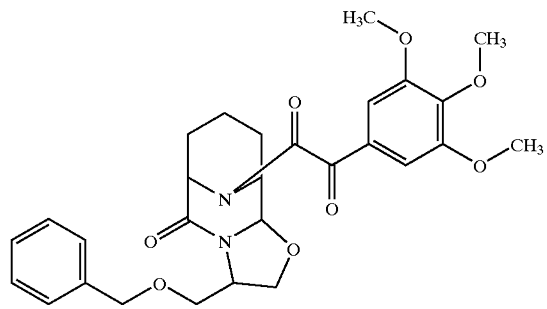 | 1 | 2 | 2.2 |
| 43 | 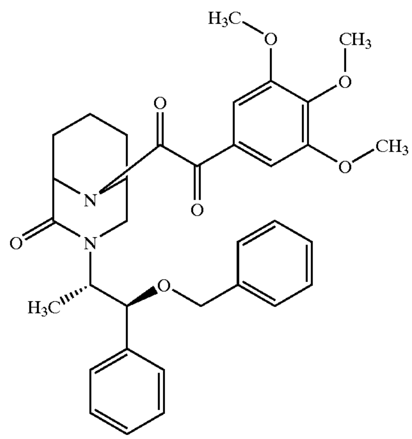 | 1 | 2 | NI |
| 44 | 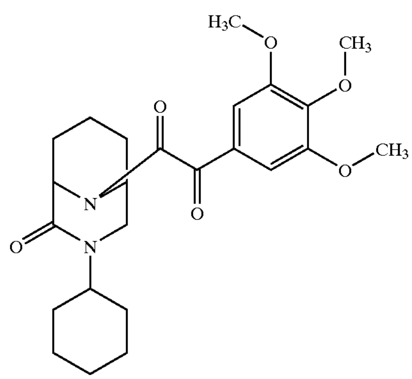 | 1 | 2 | 3.0 |
| 45 | 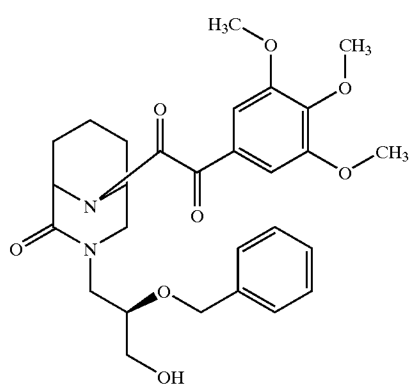 | 1 | 2 | 0.58 |

TABLE 1-continued

| Compound Number | Molecular Structure | Prepn by Scheme No. | Number of Isomers | K$_{i(app)}$ (μM) |
|---|---|---|---|---|
| 46 | 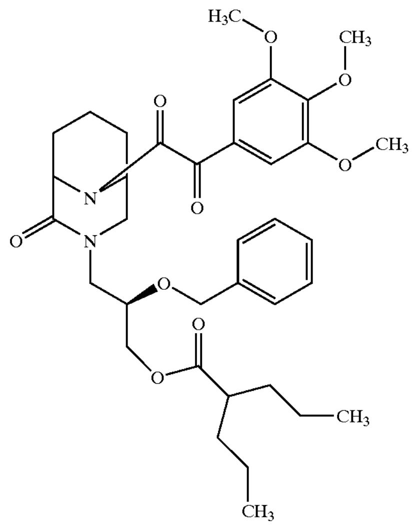 | 1 | 2 | 0.448 |
| 47 | 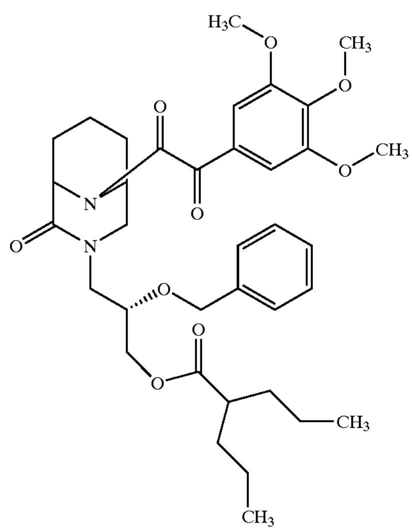 | 1 | 2 | 0.2 |
| 48 | 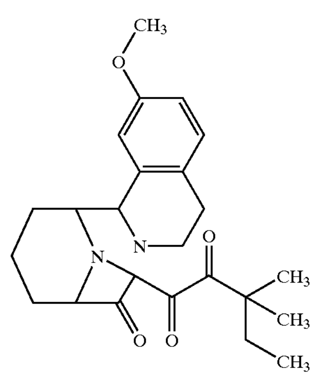 | 2 | 2 | 1.6 |

TABLE 1-continued

| Compound Number | Molecular Structure | Prepn by Scheme No. | Number of Isomers | Rotamase $K_{i(app)}$ ($\mu M$) |
|---|---|---|---|---|
| 49 | 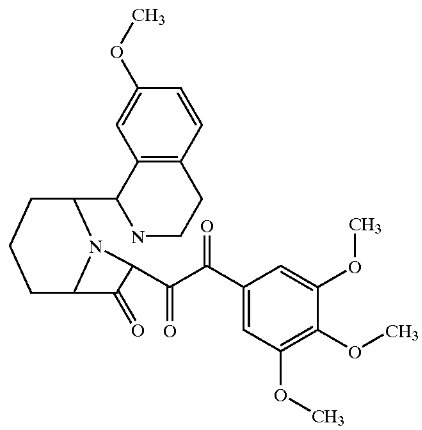 | 2 | 2 | 0.08 |
| 50 | 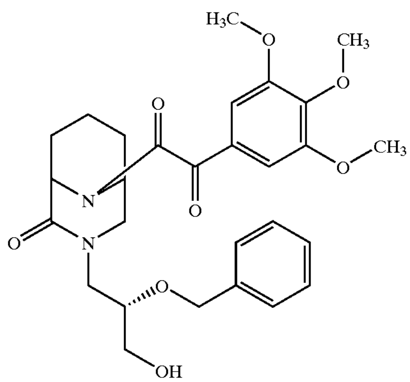 | 1 | 2 | 0.56 |
| 51 | 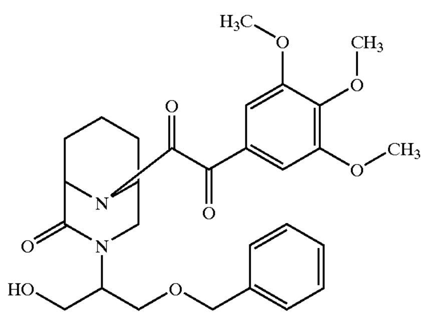 | 1 | 4 | 4 |
| 53 | 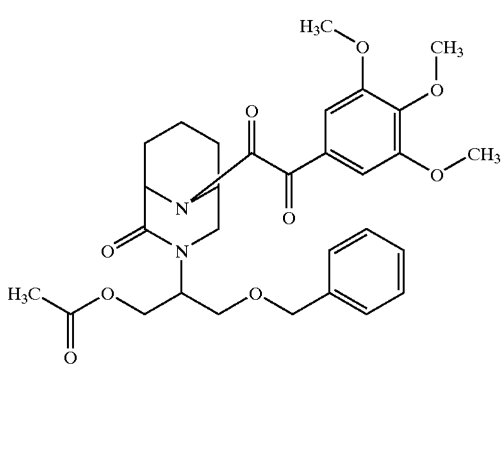 | 1 | 4 | 5 |

TABLE 1-continued

| Compound Number | Molecular Structure | Prepn by Scheme No. | Number of Isomers | Rotamase $K_{i(app)}$ ($\mu M$) |
|---|---|---|---|---|
| 54 | 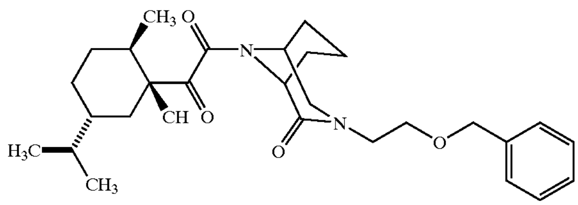 | 1 | 2 | 6* |
| 55 | 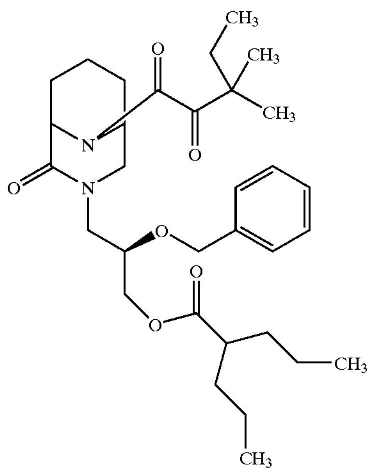 | 1 | 2 | 40% inhibition @ 2.5 $\mu M$ |
| 56 | 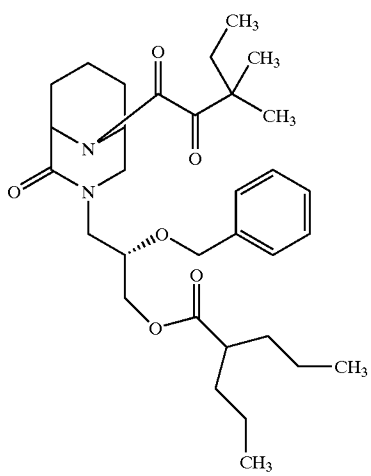 | 1 | 2 | 40% inhibition @ 2.5 $\mu M$ |
| 57 | 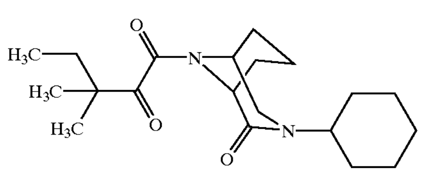 | 1 | 2 | 74 |

TABLE 1-continued

| Compound Number | Molecular Structure | Prepn by Scheme No. | Number of Isomers | Rotamase $K_{i(app)}$ ($\mu$M) |
|---|---|---|---|---|
| 58 | 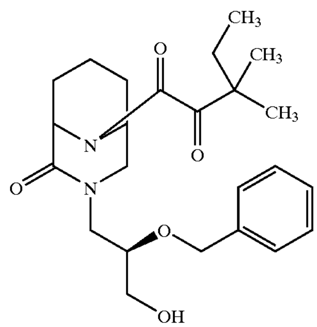 | 1 | 2 | 3.0 |
| 59 | 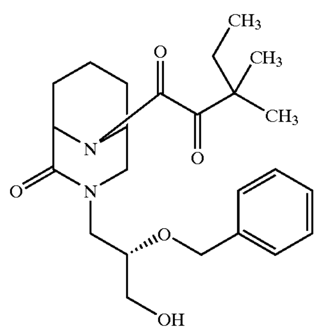 | 1 | 2 | 3.8 |
| 60 | 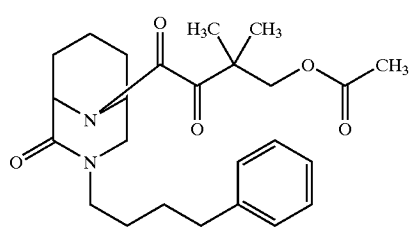 | 1 | 2 | 3.0 |
| 61 | 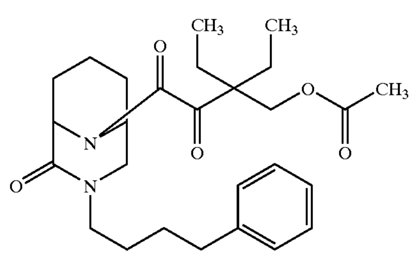 | 1 | 2 | 0.79 |
| 62 | 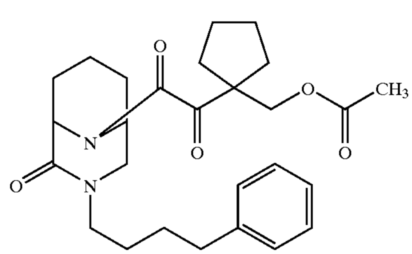 | 1 | 2 | 0.16 |

TABLE 1-continued

| Compound Number | Molecular Structure | Prepn by Scheme No. | Number of Isomers | Rotamase $K_{i(app)}$ ($\mu M$) |
|---|---|---|---|---|
| 63 | 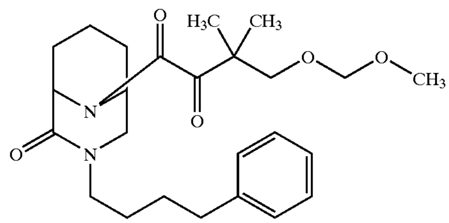 | 1 | 2 | 3.1 |
| 64 | 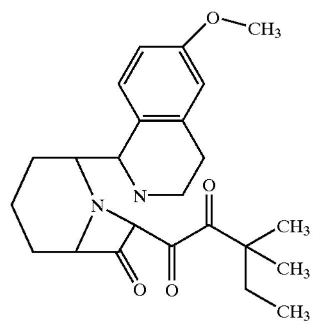 | 2 | 2 | 0.62 |
| 65 | 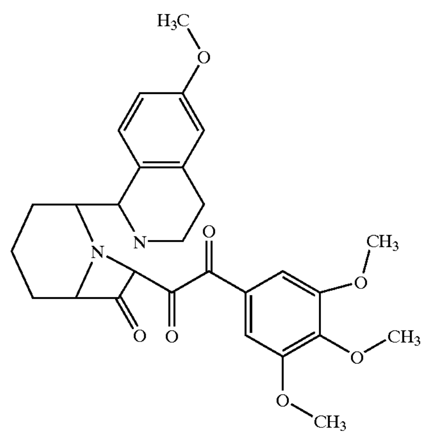 | 2 | 2 | 0.175 |
| 66 | 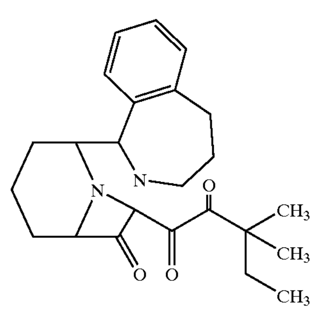 | 2 | 2 | 16 |

TABLE 1-continued

| Compound Number | Molecular Structure | Prepn by Scheme No. | Number of Isomers | K$_{i(app)}$ (µM) |
|---|---|---|---|---|
| 67 | 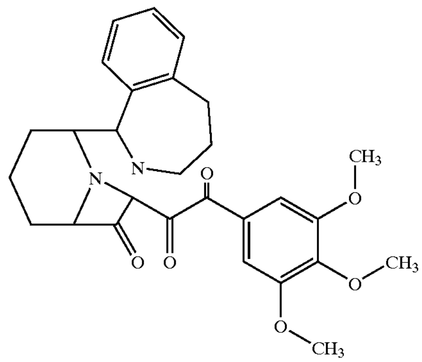 | 2 | | 0.88 |
| 68 | 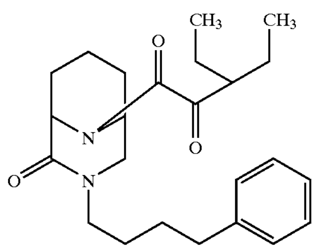 | 1 | 2 | 2.5 |
| 69 | 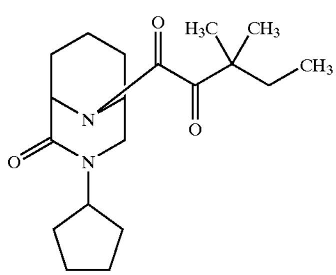 | 1 | 2 | 33 |
| 70 | 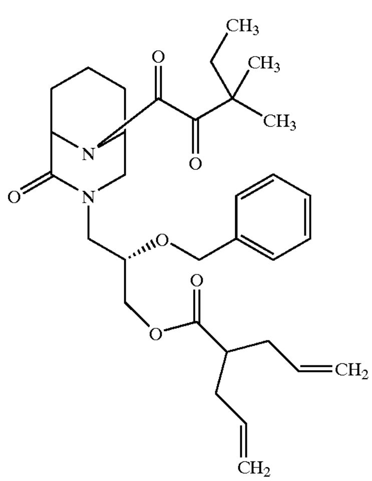 | 1 | 2 | 0.89 |

TABLE 1-continued

| Compound Number | Molecular Structure | Prepn by Scheme No. | Number of Isomers | Rotamase $K_{i(app)}$ ($\mu$M) |
|---|---|---|---|---|
| 71 | 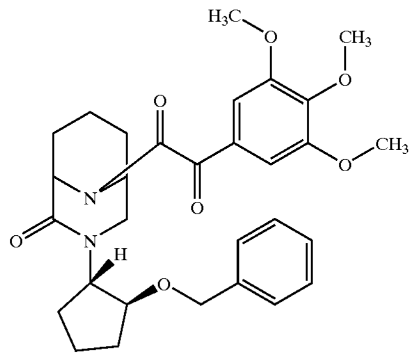 | 1 | 2 | 4.7 |
| 72 | 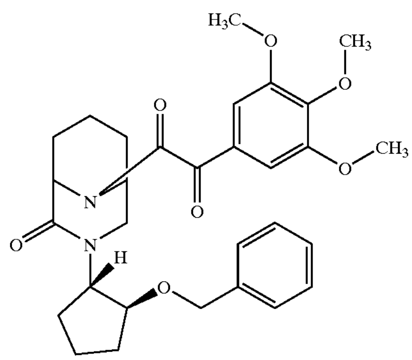 | 1 | 2 | 0.24 |
| 73 | 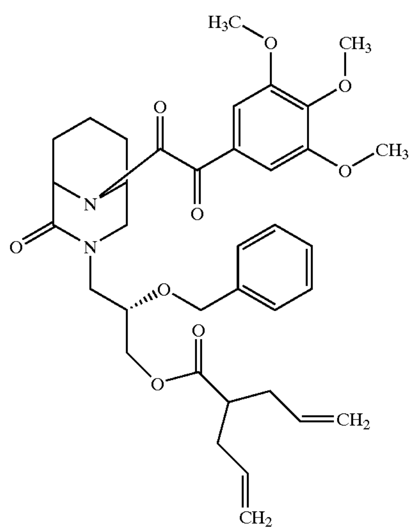 | 1 or 2 | 2 | 0.063 |
| 74 | 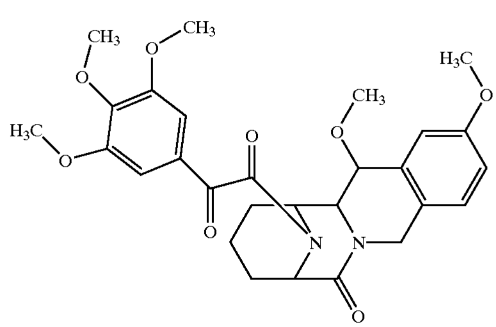 | 4 | up to 8 | 0.111 |

TABLE 1-continued
| Compound Number | Molecular Structure | Prepn by Scheme No. | Number of Isomers | $K_{i(app)}$ ($\mu$M) |
|---|---|---|---|---|
| 75 | 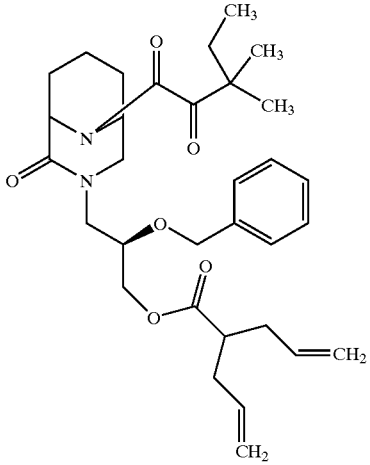 | 1 | 2 | 0.79 |
| 76 | 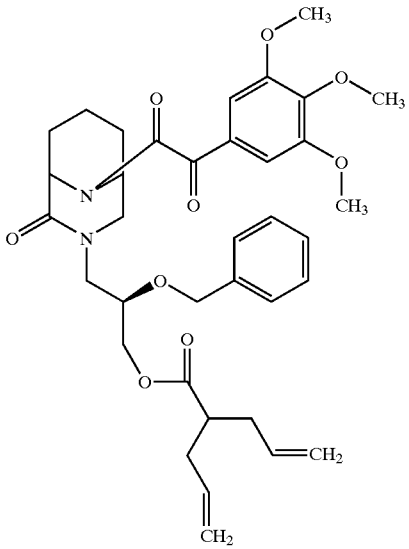 | 1 | 2 | 0.112 |
| 77 | 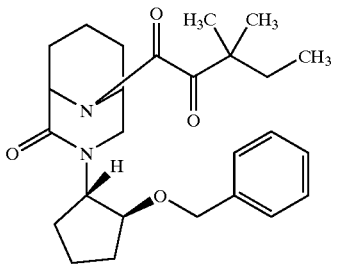 | 1 | 2 | 20.5 |

TABLE 1-continued

| Compound Number | Molecular Structure | Prepn by Scheme No. | Number of Isomers | $K_{i(app)}$ ($\mu$M) |
|---|---|---|---|---|
| 78 | 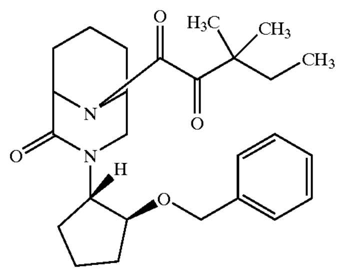 | 1 | 2 | 4.1 |
| 79 | 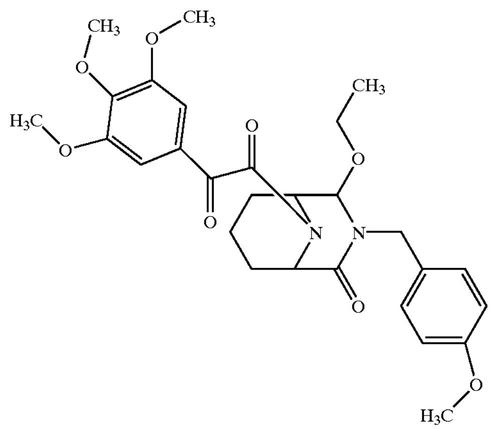 | 1 or 2 | 4 | 0.7 |
| 80 | 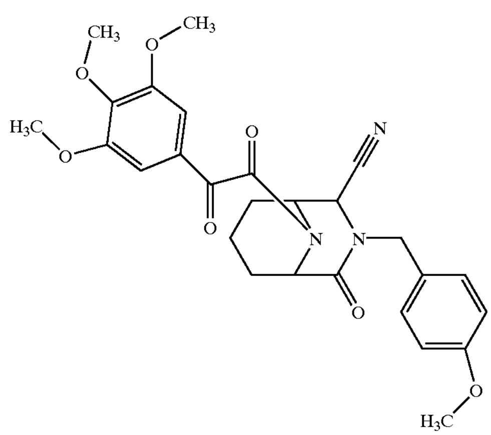 | 1 | 4 | 1.8 |
| 81 | 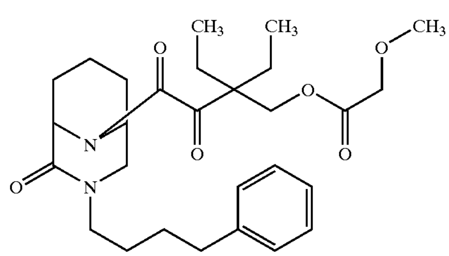 | 1 | 2 | 1.1 |

TABLE 1-continued

| Compound Number | Molecular Structure | Prepn by Scheme No. | Number of Isomers | Rotamase $K_{i(app)}$ ($\mu$M) |
|---|---|---|---|---|
| 82 | 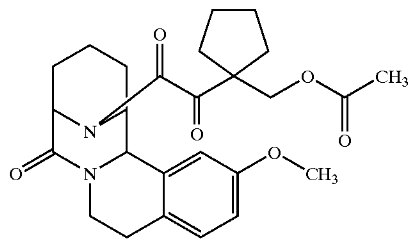 | 2 | 2 | 3 |
| 83 | 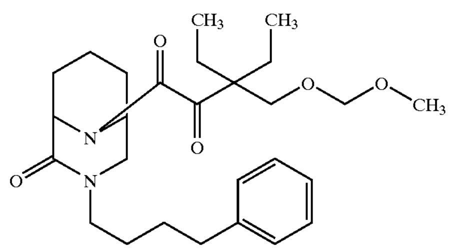 | 1 | 2 | 0.86 |
| 84 | 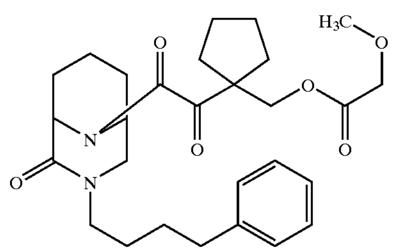 | 1 | 2 | 0.134 |
| 85 | 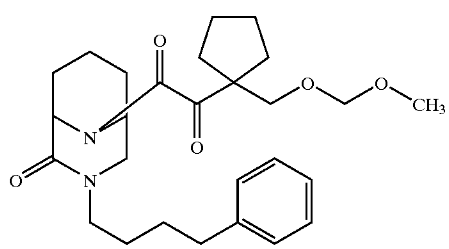 | 1 | 2 | 0.324 |
| 86 | 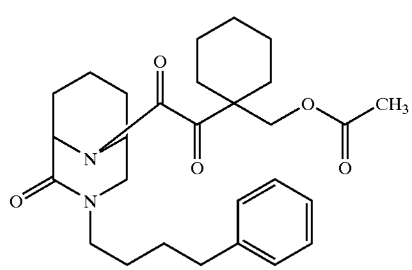 | 1 | | 1.3 |
| 87 | 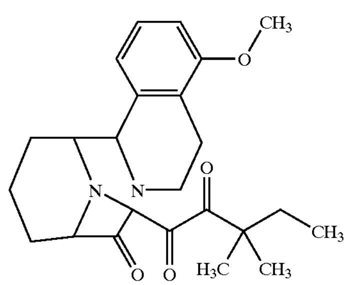 | 2 | 2 | 5 |

TABLE 1-continued

| Compound Number | Molecular Structure | Prepn by Scheme No. | Number of Isomers | Rotamase $K_{i(app)}$ ($\mu$M) |
|---|---|---|---|---|
| 88 | 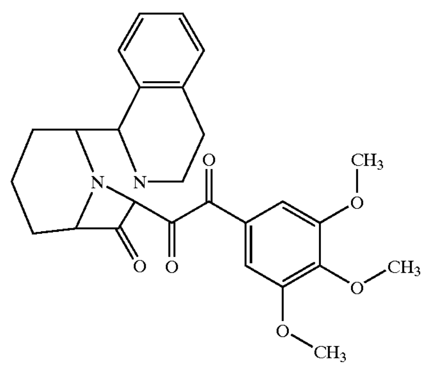 | 2 | 2 | 0.217 |
| 89 | 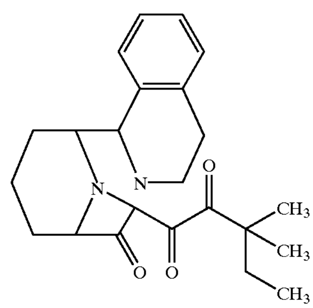 | 2 | 2 | 3.2 |
| 90 | 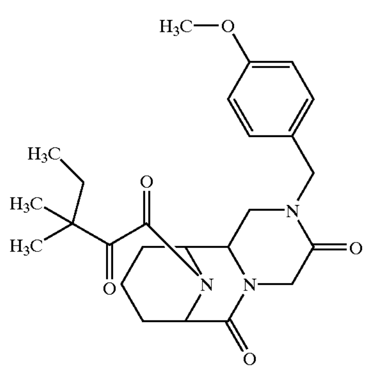 | 5 | 2 | >50 |
| 91 | 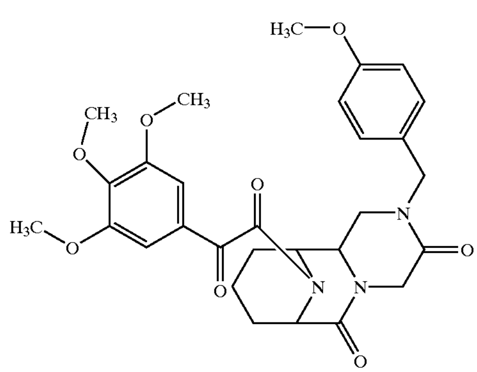 | 5 | 2 | 0.22 |

TABLE 1-continued

| Compound Number | Molecular Structure | Prepn by Scheme No. | Number of Isomers | Rotamase $K_{i(app)}$ ($\mu$M) |
|---|---|---|---|---|
| 92 | 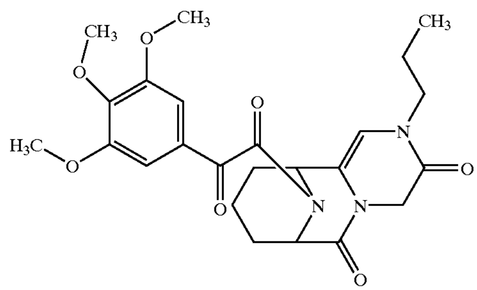 | 5 | 2 | 0.13 |
| 93 | 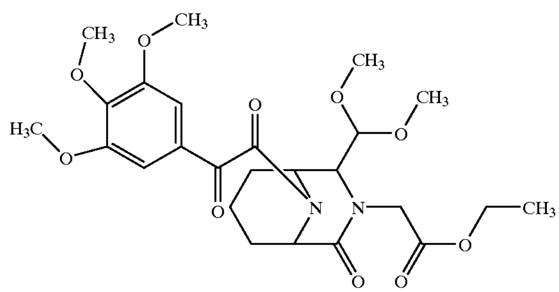 | 4 | 4 | 0.17 |
| 94 | 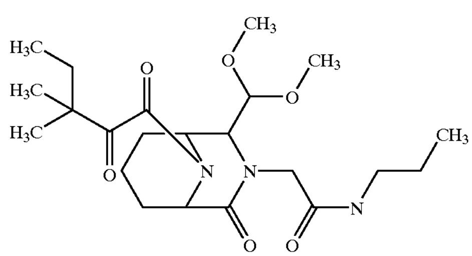 | 4 | 4 | 31.4 |
| 95 | 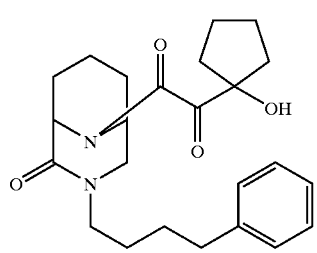 | 1 | 2 | 1.2 |
| 96 | 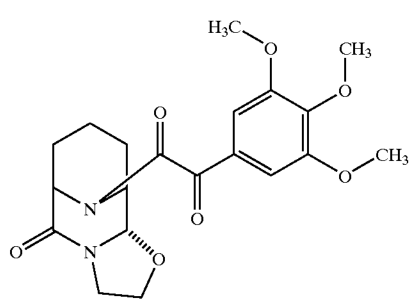 | 1 or 2 | 2 | 1.4 |

TABLE 1-continued

| Compound Number | Molecular Structure | Prepn by Scheme No. | Number of Isomers | Rotamase $K_{i(app)}$ ($\mu$M) |
|---|---|---|---|---|
| 97 | 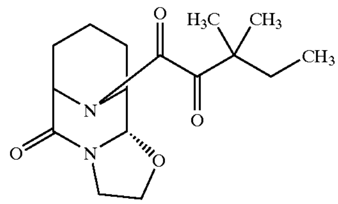 | 1 or 2 | | 9* |
| 98 | 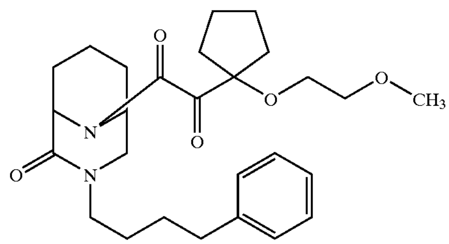 | 1 | 2 | 0.772 |
| 99 | 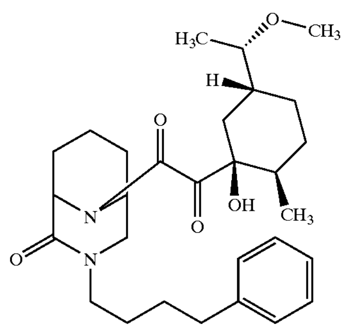 | 1 | 2 | 3.7 |
| 100 | 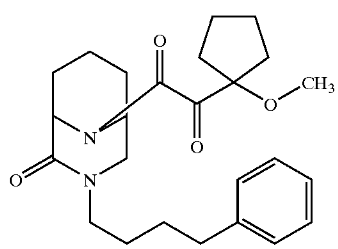 | 1 | 2 | 0.627 |
| 101 | 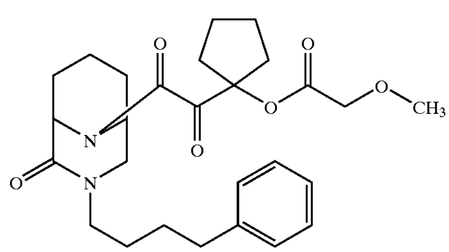 | 1 | 2 | 1.4 |
| 102 | 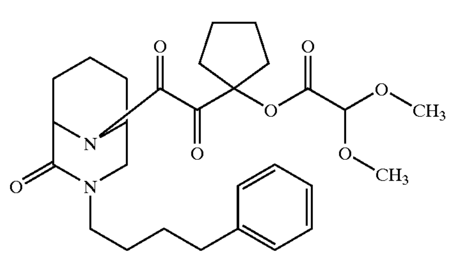 | 1 | 2 | 0.69 |

TABLE 1-continued
| Compound Number | Molecular Structure | Prepn by Scheme No. | Number of Isomers | Rotamase $K_{i(app)}$ ($\mu$M) |
|---|---|---|---|---|
| 103 | 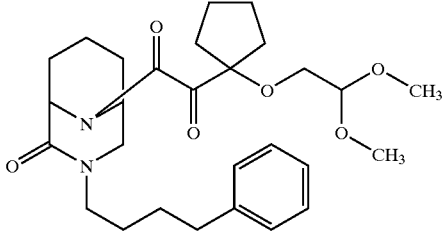 | 1 | 2 | 1.2 |
| 104 | 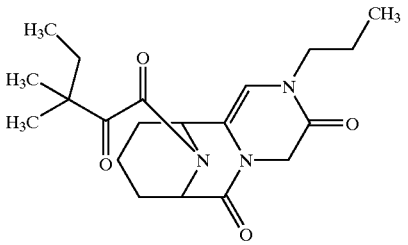 | 5 | 2 | 1.4 |
| 105 | 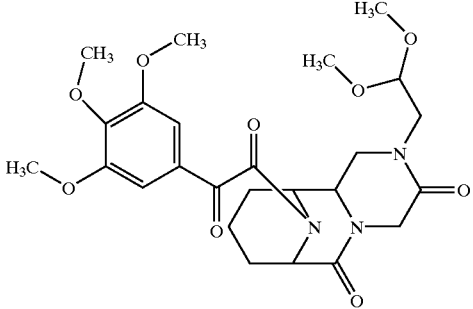 | 5 | 2 | 0.35 |
| 106 | 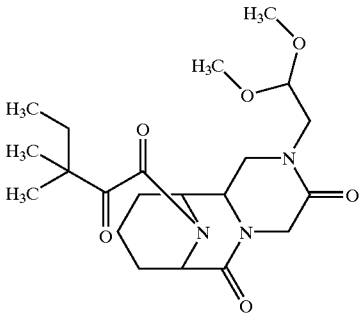 | 5 | 2 | >50 |
| 107 | 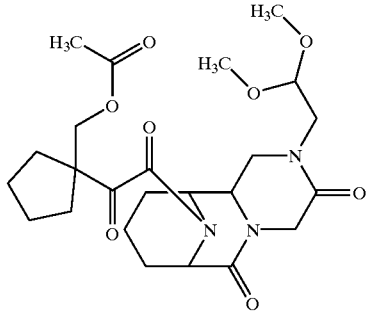 | 5 | 2 | NI |

TABLE 1-continued

| Compound Number | Molecular Structure | Prepn by Scheme No. | Number of Isomers | $K_{i(app)}$ ($\mu M$) |
|---|---|---|---|---|
| 108 | 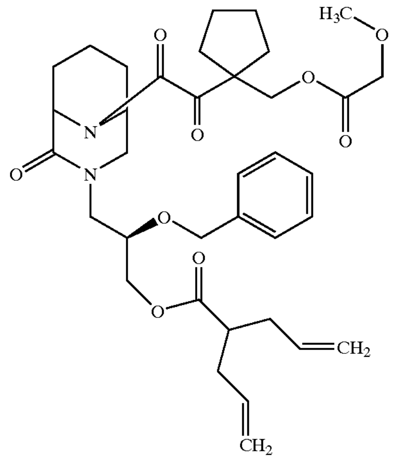 | 1 | 2 | 0.061 |
| 109 | 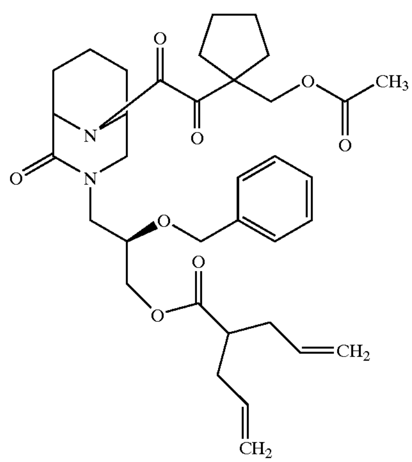 | 1 | 2 | 0.049 |
| 110 | 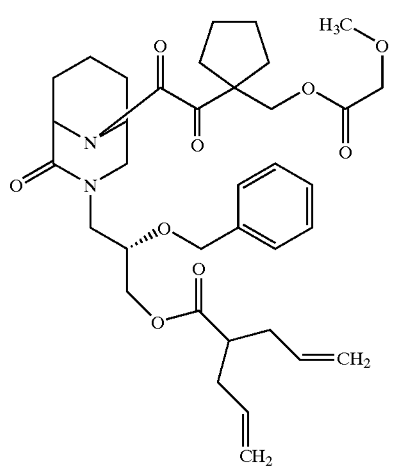 | 1 | 2 | 0.086 |

TABLE 1-continued

| Compound Number | Molecular Structure | Prepn by Scheme No. | Number of Isomers | K$_{i(app)}$ ($\mu$M) |
|---|---|---|---|---|
| 111 | 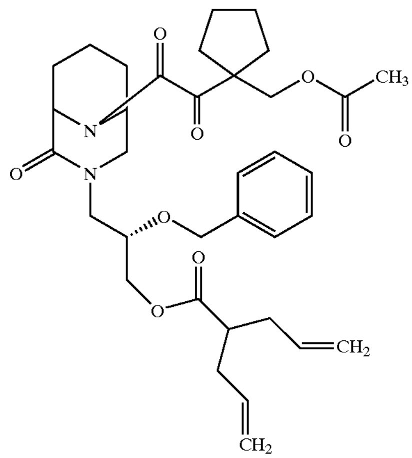 | 1 | 2 | 0.663 |
| 112 | 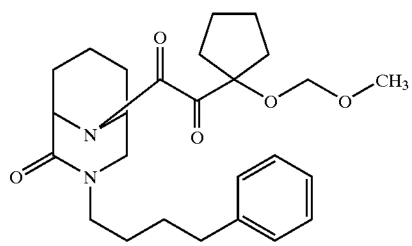 | 1 | 2 | 1 |
| 113 | 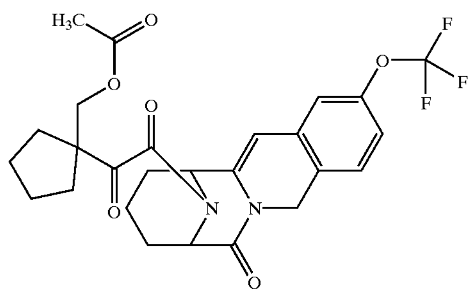 | 4 | 2 | ND |
| 114 | 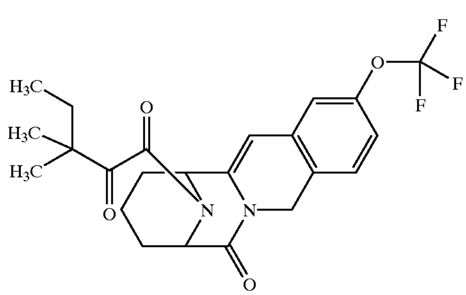 | 4 | 2 | ND |

TABLE 1-continued
| Compound Number | Molecular Structure | Prepn by Scheme No. | Number of Isomers | Rotamase $K_{i(app)}$ ($\mu M$) |
|---|---|---|---|---|
| 115 | 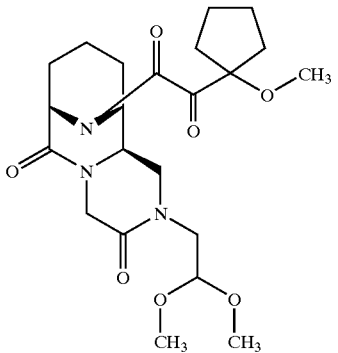 | 5 | | >20 |
| 116 | 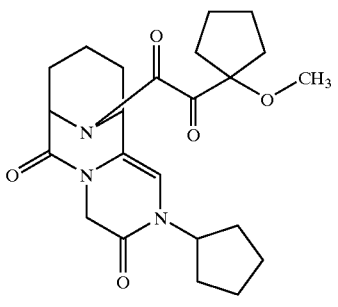 | 5 | 2 | 0.96 |
| 117 | 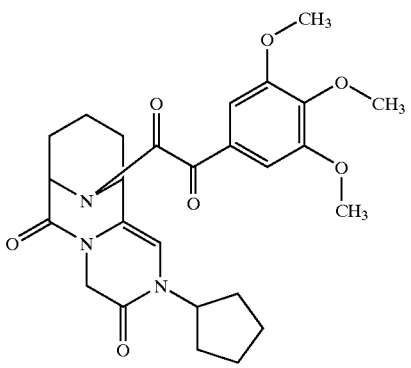 | 5 | 2 | 0.084 |
| 118 | 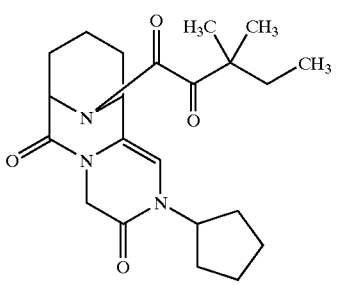 | 5 | 2 | 1 |

TABLE 1-continued
| Compound Number | Molecular Structure | Prepn by Scheme No. | Number of Isomers | Rotamase $K_{i(app)}$ ($\mu M$) |
|---|---|---|---|---|
| 119 | 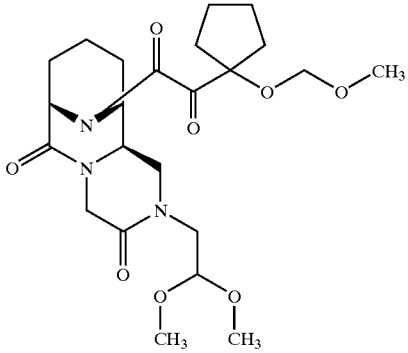 | 5 | | >40 |
| 120 | 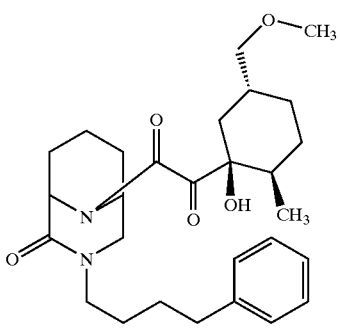 | 1 | 2 | 2.5 |
| 121 | 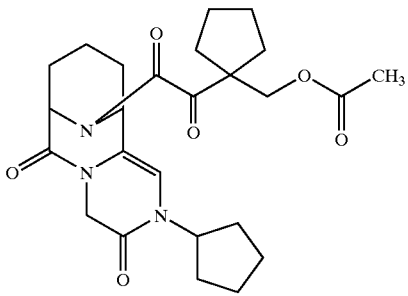 | 5 | 2 | 0.78 |
| 122 | 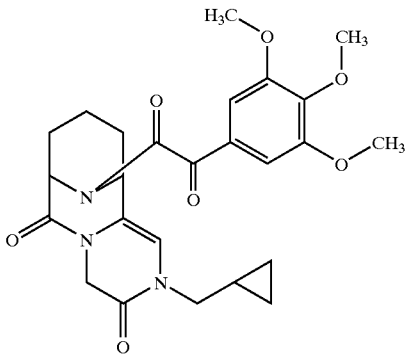 | 5 | 2 | 0.15 |

TABLE 1-continued

| Compound Number | Molecular Structure | Prepn by Scheme No. | Number of Isomers | Rotamase $K_{i(app)}$ ($\mu M$) |
|---|---|---|---|---|
| 123 | 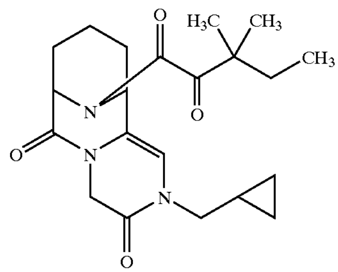 | 5 | 2 | 1.2 |
| 124 | 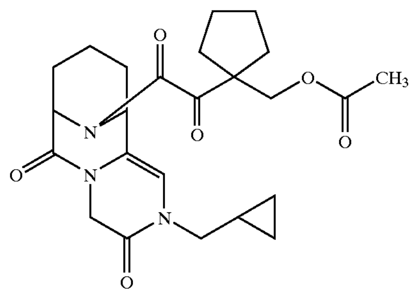 | 5 | 2 | 0.38 |
| 125 | 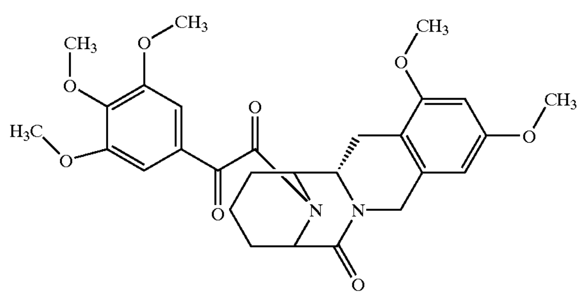 | 4 | 2 | 0.85 |
| 126 | 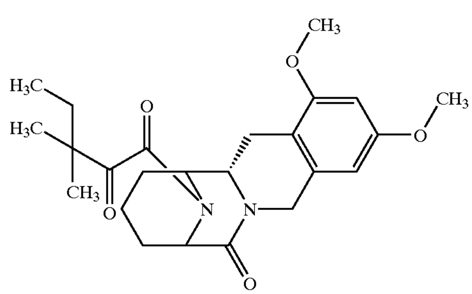 | 4 | 2 | 5 |
| 127 | 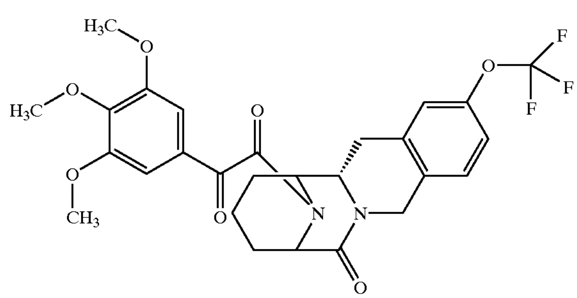 | 4 | 2 | 2.6 |

TABLE 1-continued

| Compound Number | Molecular Structure | Prepn by Scheme No. | Number of Isomers | Rotamase $K_{i(app)}$ (µM) |
|---|---|---|---|---|
| 128 | 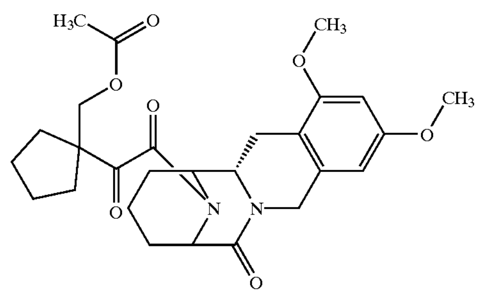 | 4 | 2 | 2 |
| 129 | 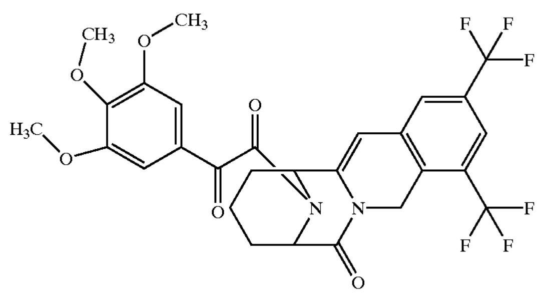 | 4 | 2 | 0.37 |
| 130 | 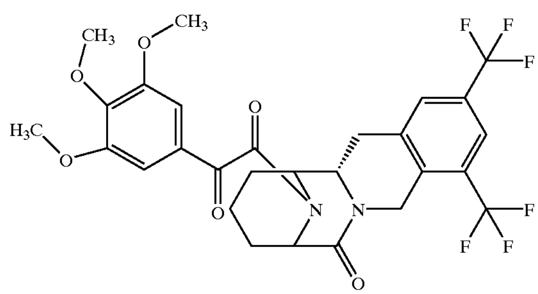 | 4 | 2 | 10 |
| 131 | 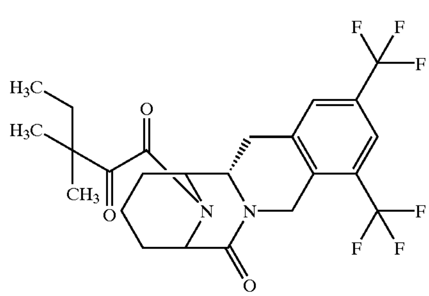 | 4 | 2 | NI |
| 132 | 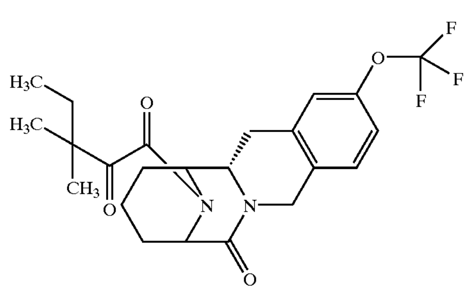 | 4 | 2 | >20 |

TABLE 1-continued

| Compound Number | Molecular Structure | Prepn by Scheme No. | Number of Rotamase Isomers | $K_{i(app)}$ ($\mu M$) |
|---|---|---|---|---|
| 133 | 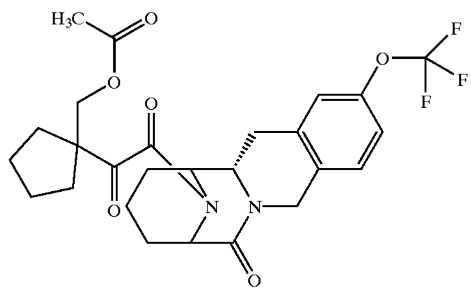 | 4 | 2 | 3.9 |
| 134 | 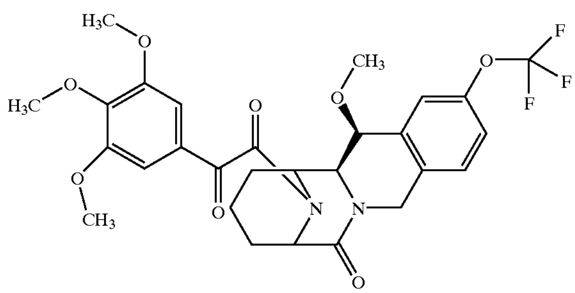 | 4 | 2 | 10 |
| 135 | 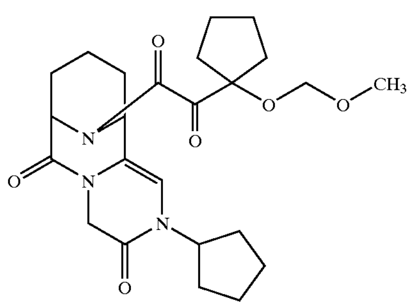 | 5 | | 1.4 |
| 136 | 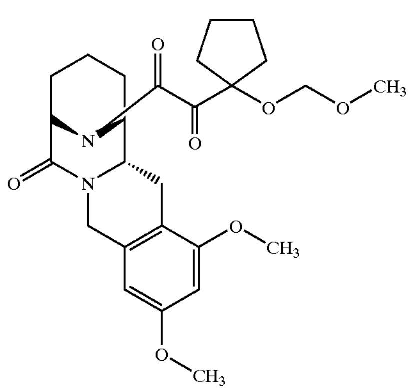 | 4 | | 2.4 |

TABLE 1-continued

| Compound Number | Molecular Structure | Prepn by Scheme No. | Number of Isomers | Rotamase $K_{i(app)}$ ($\mu$M) |
|---|---|---|---|---|
| 137 | 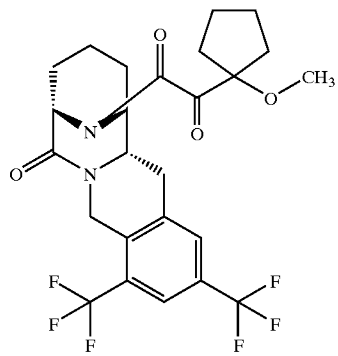 | 4 | | 9.7 |
| 138 | 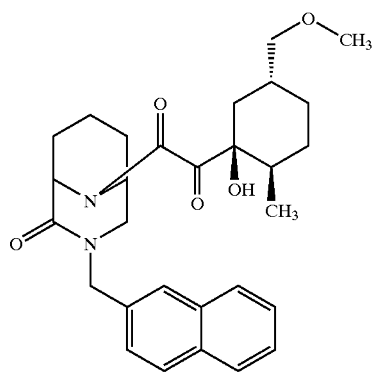 | 1 | 2 | 1.3 |
| 139 | 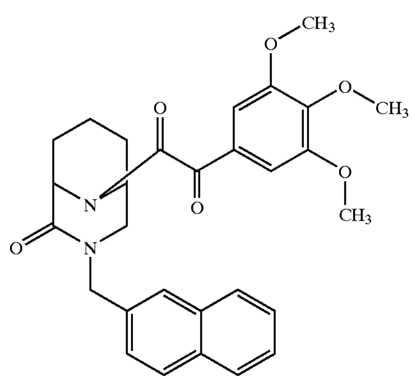 | 1 | 2 | 0.355 |
| 140 | 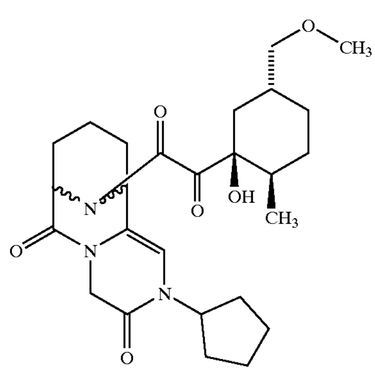 | 5 | 2 | 10 |

TABLE 1-continued

| Compound Number | Molecular Structure | Prepn by Scheme No. | Number of Isomers | Rotamase $K_{i(app)}$ ($\mu$M) |
|---|---|---|---|---|
| 141 | 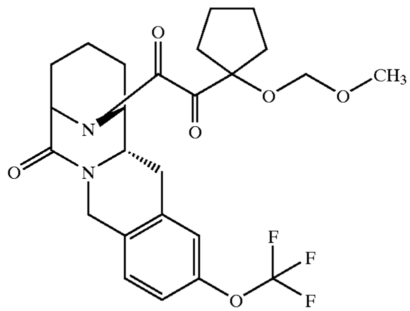 | 5 | | 4 |
| 142 | 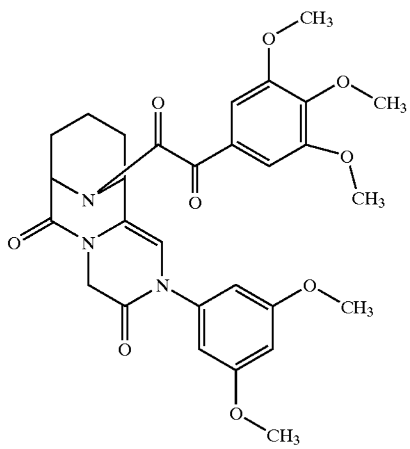 | 5 | 2 | 0.054 |
| 143 | 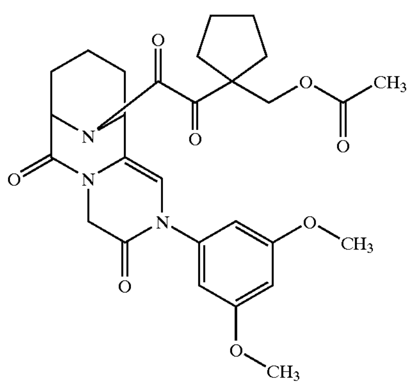 | 5 | 2 | 0.19 |
| 144 | 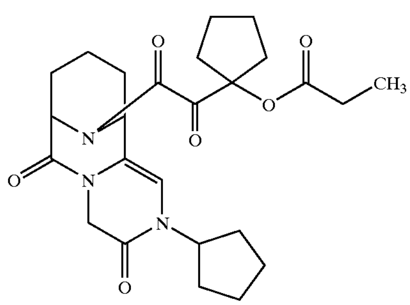 | 5 | 2 | 1.2 |

TABLE 1-continued

| Compound Number | Molecular Structure | Prepn by Scheme No. | Number of Isomers | Rotamase $K_{i(app)}$ ($\mu M$) |
|---|---|---|---|---|
| 145 | 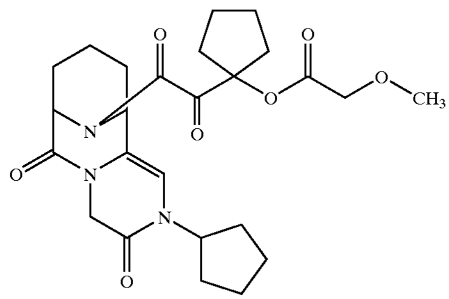 | 5 | 2 | 1.7 |
| 146 | 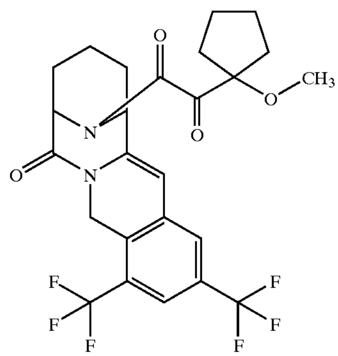 | 4 | 2 | >50 |
| 147 | 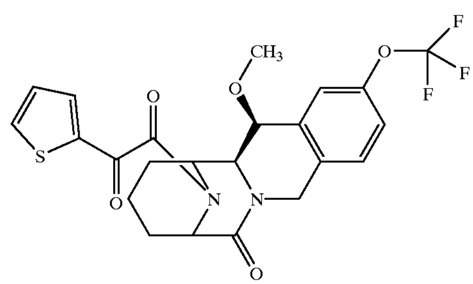 | 4 | 2 | 1.4 |
| 148 | 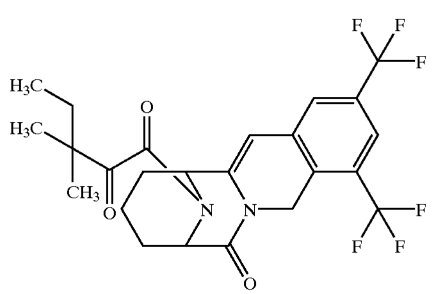 | 4 | 2 | NI |
| 149 | 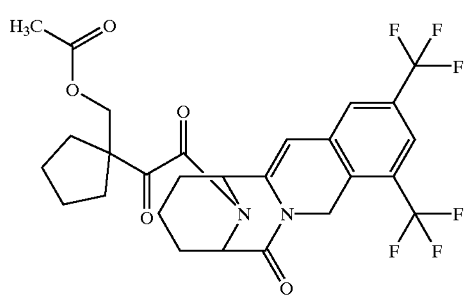 | 4 | 2 | >50 |

TABLE 1-continued

| Compound Number | Molecular Structure | Prepn by Scheme No. | Number of Rotamase Isomers | K$_{i(app)}$ (μM) |
|---|---|---|---|---|
| 150 | 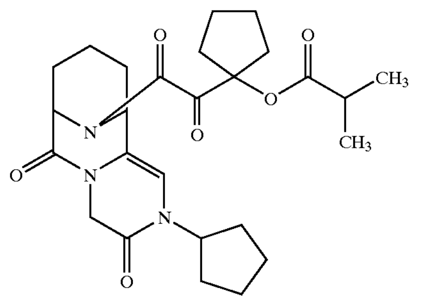 | 5 | 2 | 1.5 |
| 151 | 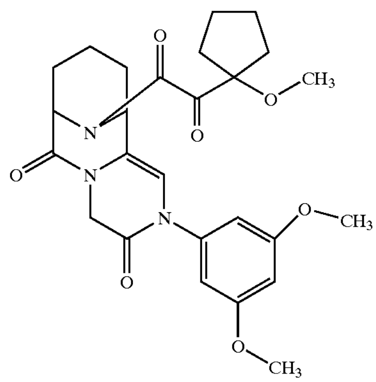 | 5 | 2 | 0.53 |
| 152 | 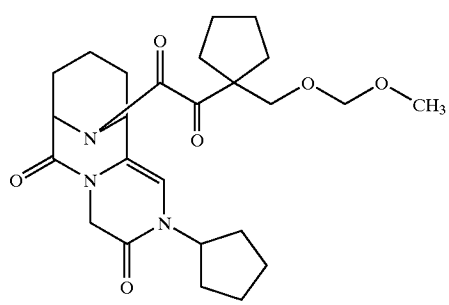 | 5 | 2 | 2.8 |
| 153 | 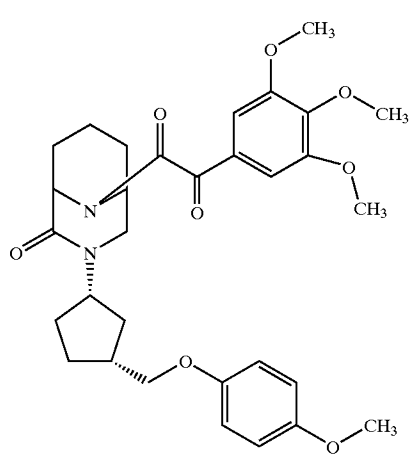 | 1 | 2 | 0.52 |

TABLE 1-continued

| Compound Number | Molecular Structure | Prepn by Scheme No. | Number of Isomers | Rotamase $K_{i(app)}$ ($\mu M$) |
|---|---|---|---|---|
| 154 | 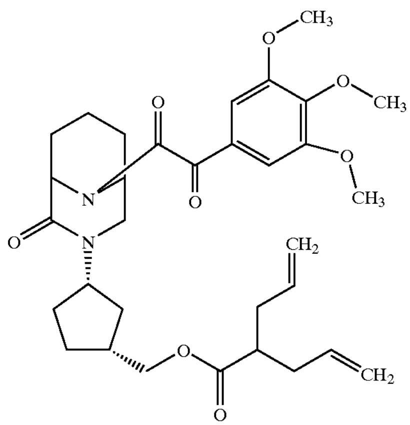 | 1 | 2 | 0.244 |
| 155 | 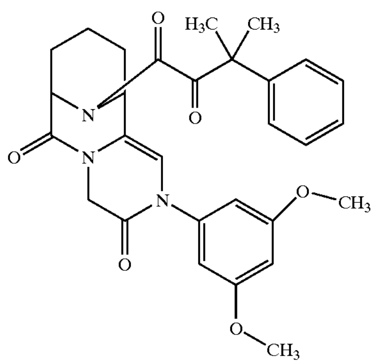 | 5 | 2 | 1.2 |
| 156 | 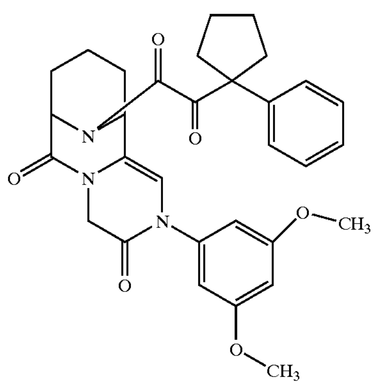 | 5 | 2 | 1.5 |
| 157 | 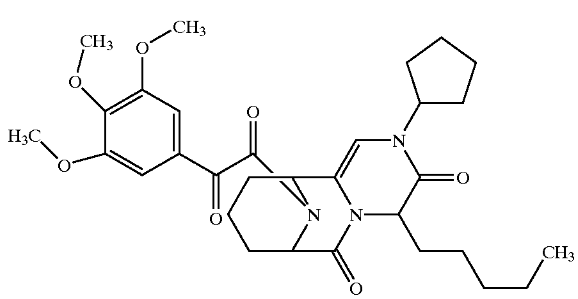 | 5 | 2 | 1.6 |

TABLE 1-continued

| Compound Number | Molecular Structure | Prepn by Scheme No. | Number of Rotamase Isomers | $K_{i(app)}$ ($\mu$M) |
|---|---|---|---|---|
| 158 | 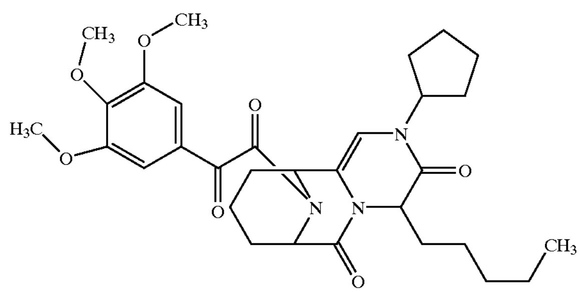 | 5 | 2 | 0.776 |
| 159 | 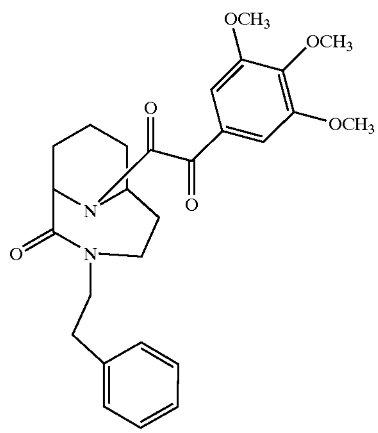 | 6 | 1 | 0.76 |
| 160 | 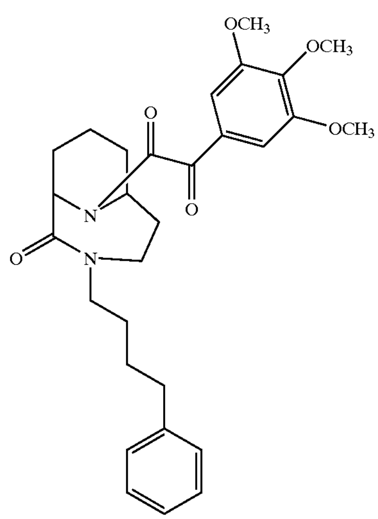 | 6 | 1 | 0.239 |

TABLE 1-continued
| Compound Number | Molecular Structure | Prepn by Scheme No. | Number of Rotamase Isomers | $K_{i(app)}$ ($\mu$M) |
|---|---|---|---|---|
| 161 | 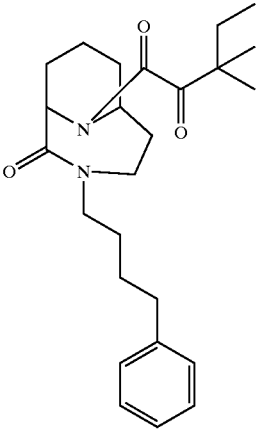 | 6 | 1 | 5 |
| 162 | 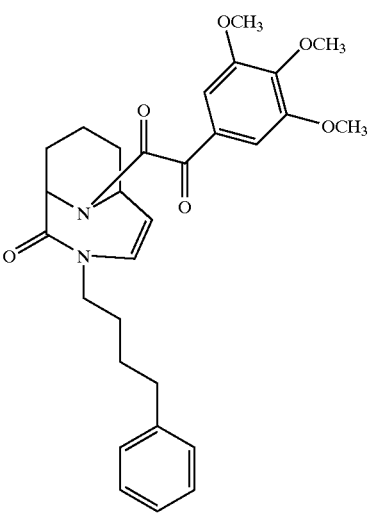 | 7 | 1 | 0.347 |
| 163 | 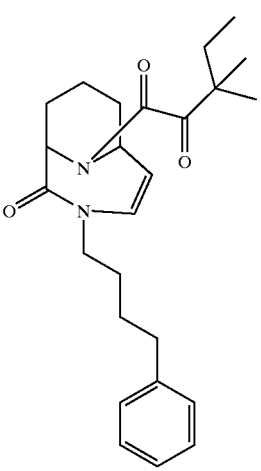 | 6 | 1 | 0.381 |

TABLE 1-continued

| Compound Number | Molecular Structure | Prepn by Scheme No. | Number of Isomers | Rotamase $K_{i(app)}$ ($\mu$M) |
| --- | --- | --- | --- | --- |
| 164 | 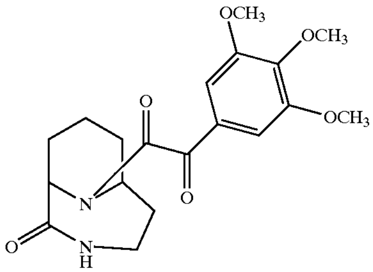 | 6 | 1 | 3.3 |
| 165 | 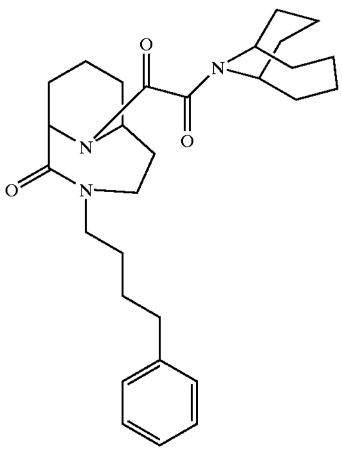 | 6 | | 8.6 |

Notes: NI = no inhibition at the concentrations tested; ND = not determined.

Pharmaceutical Compositions and Treatments

FKBP-inhibiting agents of the invention, such as the compounds exemplified above, may be used to prepare pharmaceutical compositions, such as those described below.

The pharmaceutical compositions of this invention comprise an effective neurite-outgrowth-stimulating compound of formula (I-a) or (I-b) and an inert, pharmaceutically acceptable carrier or diluent. The pharmaceutical compositions may additionally comprise a neurotrophic factor. These compositions are prepared in unit-dosage forms appropriate for various routes of administration.

In one embodiment, efficacious levels of non-peptide rotamase-inhibiting compounds are provided so as to provide therapeutic benefits involving regulation of FKBP. By "efficacious levels" of compounds is meant levels in which the FKBP binding of FKBP12 is, at a minimum, regulated. The compounds may be administered in the form of a prodrug which, in general, is designed to enhance absorption and is cleaved in vivo to form the active component. Efficacious levels may also be achieved by administration of pharmaceutically active metabolites (products of metabolic conversions) of the compound.

A compound of formula (I-a) or (I-b) is administered in a suitable dosage form prepared by combining a therapeutically effective amount (i.e., an efficacious level sufficient to achieve the desired therapeutic effect through FKBP regulation) of a compound of formula (I-a) or (I-b) (as an active ingredient) with standard pharmaceutical carriers or diluents according to conventional procedures. These procedures may involve mixing, granulating, and compressing or dissolving the ingredients as appropriate to attain the desired preparation.

The pharmaceutical carrier employed may be in a suitable form, for example, either a solid or liquid. Exemplary solid carriers include lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like.

A variety of pharmaceutical forms can be employed. For example, if a solid carrier is used, the preparation can be tableted, placed in a hard gelatin capsule in powder or pellet form, or formed into a troche or lozenge. The amount of solid carrier may vary, but preferably will be from about 25 mg to about 1 g. If a liquid carrier is used, the preparation will preferably be in the form of syrup, emulsion, soft gelatin capsule, sterile injectable solution or suspension in an ampoule or vial, or nonaqueous liquid suspension.

To obtain a stable water-soluble dose form, a pharmaceutically acceptable salt of a compound of formula (I-a) or (I-b) may be dissolved in an aqueous solution of an organic or inorganic acid, such as 0.3M solution of succinic acid, or more preferably, citric acid. If a soluble salt form is not available, the compound of formula (I-a) or (I-b) may be dissolved in a suitable cosolvent or combination of cosolvents. Examples of suitable cosolvents include alcohol, propylene glycol, polyethylene glycol 300, polysorbate 80, glycerin and the like in concentrations ranging from 0 to 60% of the total volume. In a preferred embodiment, the active compound of formula (I-a) or (I-b) is dissolved in DMSO and diluted with water. The composition may also be in the form of a solution of a salt form of the active ingredient in an appropriate aqueous vehicle, such as water or isotonic saline or dextrose solution.

It will be appreciated that the actual preferred dosages of the formula (I-a) and (I-b) compounds used in the compositions of this invention may vary according to the particular complex being used, the particular composition formulated, the mode of administration and the particular site, and the host and disease being treated. Optimal dosages for a given set of conditions can be ascertained by those skilled in the art using conventional dosage-determination tests, e.g., in view of the experimental data provided herein. For oral administration, the usual daily dose generally employed is from about 0.001 to about 1000 mg/kg of body weight, with courses of treatment repeated at appropriate intervals. Initial pharmacokinetics for humans may be determined from the rat model as described by Gold et al., *Experimental Neurology*, 147:269–278 (1997).

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers comprising excipients and/or auxiliaries which facilitate processing of the active compounds into preparations that can be used pharmaceutically. Of course, the appropriate formulation is dependent upon the route of administration chosen.

For oral administration, the compounds can be formulated readily by combining the active compounds with pharmaceutically acceptable carriers known in the art. Such carriers allow the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining an active compound with a solid excipient, optionally grinding the resulting mixture, and processing the mixture of granules, after adding suitable auxiliaries, if desired, to obtain tablets or dragee cores. Suitable excipients include, e.g.: fillers such as sugars, including lactose, sucrose, mannitol, or sorbitol; and cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, polyvinylpyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparation forms that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate, and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in a conventional manner.

An example for preparing an oral pharmaceutical composition of this invention is as follows: 100 mg of a compound of formula (I-a) or (I-b) is mixed with 750 mg of lactose, and the mixture is incorporated into an oral unit-dosage form, such as a hard gelatin capsule, which is suitable for oral administration.

For administration by inhalation, the compounds according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

For injection, the agents of the invention may be formulated in aqueous solutions, preferably in physiologically compatible buffers such as Hanks's solution, Ringer's solution, or physiological saline buffer. For transmucosal administration, penetrants appropriate to the barier to be permeated are used in the formulation and may be selected form those known in the art.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles for preparing such formulations include fatty oils such as sesame oil, or synthetic fatty acid esters such as ethyl oleate or triglycerides, or liposomes. Aqueous injection suspensions may contain substances that increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

A parenteral pharmaceutical composition of this invention suitable for administration by injection may be prepared as follows: 100 mg of a compound of formula (I-a) or (I-b) is mixed with 10 ml of a lipophilic solvent such as a fatty oil, and the mixture is incorporated into a unit-dosage form suitable for administration by injection as an emulsion.

Alternatively, the active ingredient may be in powder form for constitution with a suitable vehicle, e.g., sterile pyrogen-free water, before use. The compounds may also be formulated in rectal compositions such as suppositories or retention enemas, e.g, containing conventional suppository bases such as cocoa butter or other glycerides.

In addition to the formulations described previously, the compounds may also be formulated as a depot preparation. Such long-acting formulations may be administered by implantation (for example, subcutaneously or intramuscularly) or by intramuscular injection. For example, the compounds may be formulated with suitable polymeric or hydrophobic materials (for example, as an emulsion in an acceptable oil) or ion-exchange resins, or as sparingly soluble derivatives, for example, as a sparingly soluble salt.

A suitable pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system (VPD is a solution of 3% w/v benzyl alcohol, 8% w/v of the nonpolar surfactant polysorbate 80, and 65% w/v polyethylene glycol 300, made up to volume in absolute ethanol). The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinylpyrrolidone; and other sugars or polysaccharides may be substituted for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agents. Various sustained-release materials have been established and are known by those skilled in the art. Sustained-release capsules may, depending on their chemical nature, release the compounds for a period of a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, various sugars, starches, cellulose derivatives, gelatin, and polymers such as polyethylene glycols.

Numerous neurotrophic factors have been identified in the art and any of those factors may be utilized in the compositions of this invention. As used herein, the term "neurotrophic factor" refers to substances that are capable of stimulating growth or proliferation of nervous tissue (but excluding the FKBP-rotamase inhibiting compounds of the invention), e.g., nerve growth factor (NGF), insulin growth factor (IGF-1) and its active truncated derivatives (gIGF-1), acidic and basic fibroblast growth factor (aFGF and bFGF, respectively), platelet-derived growth factors (PDGF), brain-derived growth factors (BDNF), ciliary neurotrophic factors (CNTF), glial cell line derived neurotrophic factor (GDNF), neurotrophin-3 (NT-3), and neurotrophin 4/5 (NT-4/5. Pharmaceutical compositions may include as active ingredients, in addition to one or more agents of the invention, one or more of such neurotrophic factors. The most preferred neurotrophic factor for use in the compositions of this invention is NGF.

Other components of the pharmaceutically acceptable compositions of this invention may include benzyl alcohol or other suitable preservatives, absorption promoters to enhance bioavailability, fluorocarbons, and/or other conventional solubilizing or dispersing agents.

A pharmaceutical composition contains a total amount of the active ingredient(s) sufficient to achieve the intended therapeutic effect. More specifically, the pharmaceutical composition contains a therapeutically effective amount (i.e., an amount effective to prevent development of or to alleviate the existing symptoms of a disease or condition mediated by FKBP) of an FKBP-inhibiting agent of the invention. The total amounts of the FKPB-inhibitory agent of the invention and any optional neurotrophic factor that may be combined with the carrier materials to produce a single-dosage form will vary depending upon the host treated and the particular mode of administration. Preferably, the compositions of the invention each contains both an FKBP-inhibiting agent and a neurotrophic factor, with the FKBP-inhibiting agent acting to potentiate the activity of the neurotrophic factor to enhance stimulation of neurite outgrowth. The amount of neurotrophic factor in such compositions is advantageously less than the amount required in a monotherapy utilizing only the factor. Preferably, the compositions are formulated so that a dosage of between 0.01 to 100 mg/kg body weight/day of a FKBP12-inhibiting agent is administered and a dosage of between 0.01 to 100 μg/kg body weight/day of a neurotrophic factor is administered to a patient receiving the compositions.

A pharmaceutical composition of the invention may be used in a method of inhibiting the rotamase enzyme activity of an FK-506 binding protein, comprising administering the composition to a patient. The inventive compositions may also be used to stimulate the growth of neurites in nerve cells, to stimulate nerve regeneration, or to promote neuronal regeneration. Preferably, the composition further comprises a neurotrophic factor.

While the invention has been illustrated by reference to specific and preferred embodiments, those skilled in the art will recognize, e.g., through routine experimentation and practice of the invention, that variations and modifications may be made. For example, those of ordinary skill in the art may recognize that apparent variations or substitutions to the compounds of formula (I-a) and formula (I-b) may be made without adversely affecting in a significant manner their efficacy in the pharmaceutical compositions. Thus, the invention is intended not to be limited by the foregoing description, but to be defined by the appended claims and their equivalents.

What is claimed is:
1. A compound of formula:

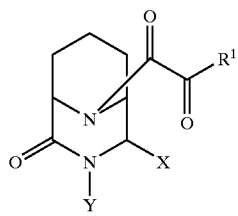

wherein:
  $R^1$ is: hydrogen; an aryl group unsubstituted or substituted with one or more substituents independently selected from the group consisting of halogen, hydroxyl, $NO_2$, $CF_3$, $C_1$–$C_6$ alkyl, $C_2$–$C_6$ alkenyl, $C_1$–$C_4$ alkyloxy, $C_2$–$C_4$ alkenyloxy, benzyloxy, phenoxy, amino, and phenyl; an alkyl or alkenyl group unsubstituted or substituted with one or more substituents independently selected from the group consisting of $C_1$–$C_4$ alkyl, $C_2$–$C_4$ alkenyl, $C_4$–$C_6$ cycloalkenyl, and hydroxy; adamantyl, $C_3$–$C_8$ cycloalkyl or $C_5$–$C_7$ cycloalkenyl group unsubstituted or substituted with one or more substituents independently selected from the group consisting of $C_1$–$C_4$ alkyl, $C_2$–$C_4$ alkenyl, $C_1$–$C_4$ alkyloxy, and hydroxy; or $C(R^{11})(R^{12})(R^{13})$, where $R^{11}$ and $R^{12}$ are each independently lower alkyl, or $R^{11}$ and $R^{12}$ together with the atom to which they are bound form cycloalkyl, and $R^{13}$ is H, OH, lower alkyl, aryl, or $(CH_2)_n$—O—$W^1$, where n is 0, 1, 2, or 3, and $W^1$ is $R^2$ or $C(O)R^2$, with $R^2$ being $C_1$–$C_3$ alkyl unsubstituted or substituted with one or two methoxy groups;
  X is hydrogen, cyano, $C_1$–$C_2$ alkyloxy, dimethoxymethyl, or =O; and
  Y is hydrogen or an alkyl, alkenyl, benzyl, or cycloalkyl group unsubstituted or substituted with one or more substituents independently selected from the group consisting of: alkyl; aryl; alkoxy; hydroxyalkyl; aryloxy; alkenyloxy; hydroxy; benzyloxy; phenoxy; $(CH_2)_p$—O—$W^2$ and $(CH_2)_p$—N—$W^2$ where p is 0, 1 or 2 and $W^2$ is $R^3$ or $C(O)R^3$, where $R^3$ is an aryl, alkyl, or alkenyl group unsubstituted or substituted with one or more substituents independently selected from the group consisting of aryl, alkyl, and alkoxy; and $(CH_2)_{p'}$—C(O)—O—$W^{2'}$ and $(CH_2)_{p'}$—C(O)—N—$W^{2'}$, where p' is 0, 1, or 2, and $W^2$ is an alkyl;
  or X and Y, together with the carbon ring atom and nitrogen heteroatom to which they are respectively bonded, form a 5- to 7-membered saturated or unsaturated heterocyclic ring unsubstituted or substituted with one or more substituents J, K, and L; where J, K, and L represent substituents independently selected from the group consisting of oxo, and $C_3$–$C_5$ cycloalkyl and $C_1$–$C_5$ alkyl groups unsubstituted or substituted with one or more substituents independently selected from the group consisting of $C_3$–$C_5$ cycloalkyl, methoxy, methoxyphenyl, and dimethoxyphenyl; or where J and K together form a phenyl ring unsubstituted or substituted with one or more substituents independently selected from the group consisting of methoxy, trifluoromethyl, trifluoromethoxy, and substituents linked to the phenyl ring through oxygen, nitrogen, carbon or sulfur and independently selected from the group consisting of halogen, hydroxyl, $NO_2$, $CF_3$, $C_1$–$C_6$ alkyl, $C_2$–$C_6$ alkenyl, $C_1$–$C_4$ alkyloxy, $C_2$–$C_4$ alkenyloxy, benzyloxy, phenoxy, amino, and phenyl;
or a pharmaceutically acceptable salt of said compound.

2. A compound according to claim 1, wherein $R^1$ is aryl unsubstituted or substituted with one or more substituents independently selected from the group consisting of halogen, hydroxyl, $NO_2$, $CF_3$, $C_1$–$C_6$ alkyl, $C_2$–$C_6$ alkenyl, $C_1$–$C_4$ alkyloxy, $C_2$–$C_4$ alkenyloxy, benzyloxy, phenoxy, amino, and phenyl.

3. A compound according to claim 1, wherein $R^1$ is selected from the group consisting of adamantyl, naphthyl, indolyl, furyl, thienyl, pyridyl, and phenyl, the phenyl having from one to three substituents independently selected from the group consisting of halogen, hydroxyl, $NO_2$, $CF_3$, $C_1$–$C_6$ alkyl, $C_2$–$C_6$ alkenyl, $C_1$–$C_4$ alkyloxy, $C_2$–$C_4$ alkenyloxy, benzyloxy, phenoxy, amino, and phenyl.

4. A compound according to claim 3, wherein $R^1$ is 3,4,5-trimethoxyphenyl.

5. A compound according to claim 1, wherein $R^1$ is

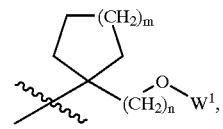

where m is 1 or 2, n is 0, 1, or 2, and $W^1$ is as defined in claim 1.

6. A compound according to claim 1, wherein $R^1$ is $C(R^{11})(R^{12})(R^{13})$, where: $R^{11}$ and $R^{12}$ together with the atom to which they are bound form cyclopentyl or cyclohexyl; and $R^{13}$ is selected from H, OH, lower alkyl, aryl, and $(CH_2)_n$—O—$W^1$, where n is 0, 1, 2, or 3, and $W^1$ is $R^2$ or $C(O)R^2$, where $R^2$ is $C_1$–$C_3$ alkyl unsubstituted or substituted with one or two methoxy groups.

7. A compound according to claim 6, wherein $R^1$ is selected from the group consisting of:

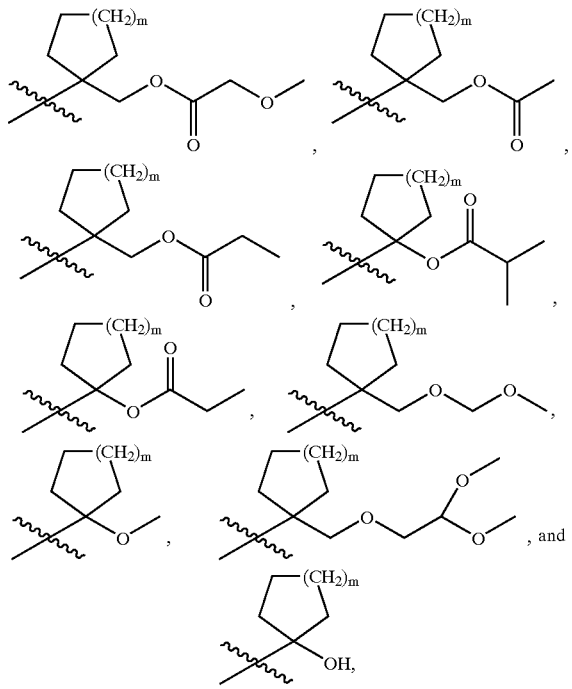

where m is 1 or 2.

8. A compound according to claim 1, wherein $R^1$ is $C(R^{11})(R^{12})(R^{13})$, where: $R^{11}$ and $R^{12}$ are each independently methyl or ethyl; and $R^{13}$ is H, OH, lower alkyl, aryl, or $(CH_2)_n$—O—$W^1$, where n is 0, 1, 2, or 3, and $W^1$ is $R^2$ or $C(O)R^2$, where $R^2$ is $C_1$–$C_3$ alkyl unsubstituted or substituted with one or two methoxy groups.

9. A compound according to claim 8, wherein $R^1$ is selected from the group consisting of:

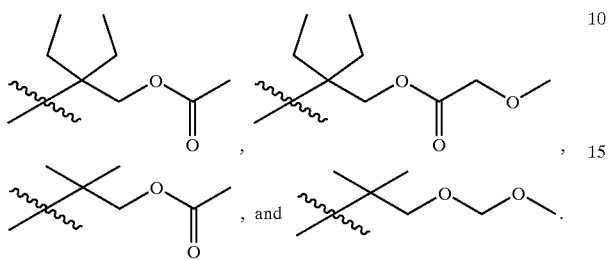

10. A compound according to claim 1, wherein Y is alkyl substituted with one or more substituents independently selected from the group consisting of alkyl, aryl, alkoxy, hydroxyalkyl, aryloxy, alkenyloxy, hydroxy, $(CH_2)_p$—O—$W^2$, and $(CH_2)_p$—N—$W^2$, where: p is 0, 1, or 2; and $W^2$ is $R^3$ or $C(O)R^3$, with $R^3$ being alkyl, alkenyl, aryl-alkyl, or aryl unsubstituted or substituted with one or more substituents selected from the group consisting of alkyl, aryl, and alkoxy.

11. A compound according to claim 10, wherein Y is selected from the group consisting of:

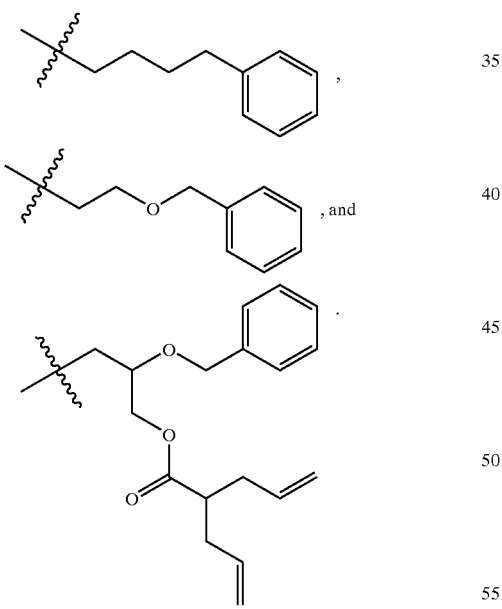

12. A compound according to claim 1, wherein X and Y, together with the carbon ring atom and nitrogen heteroatom to which they are respectively bonded, form the unsubstituted or substituted 5- to 7-membered saturated or unsaturated heterocyclic ring optionally having, in addition to said nitrogen heteroatom, one additional heteroatom selected from the group consisting of O and N.

13. A compound according to claim 12, wherein said 5–7 membered saturated or unsaturated heterocyclic ring is selected from piperidine and piperazine.

14. A compound selected from the group consisting of:

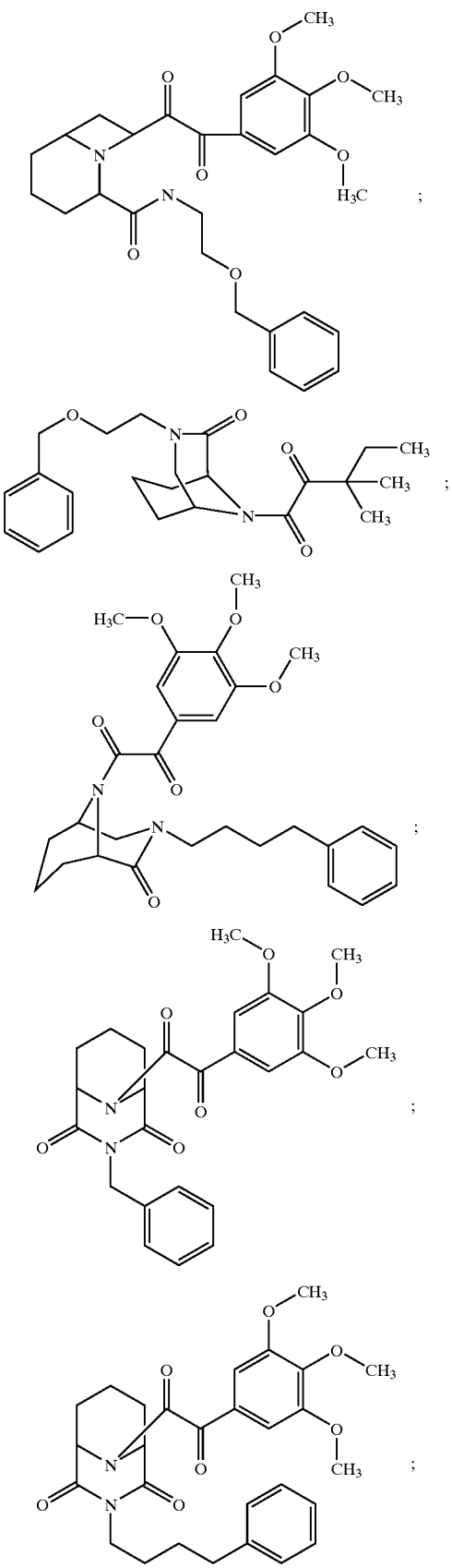

117
-continued
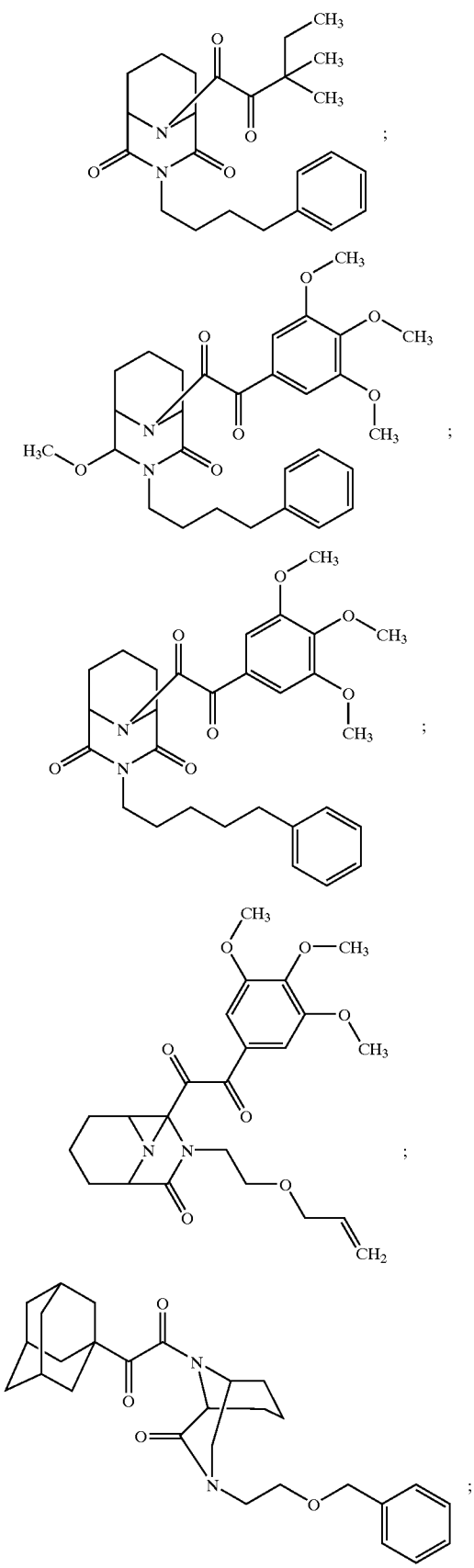
118
-continued
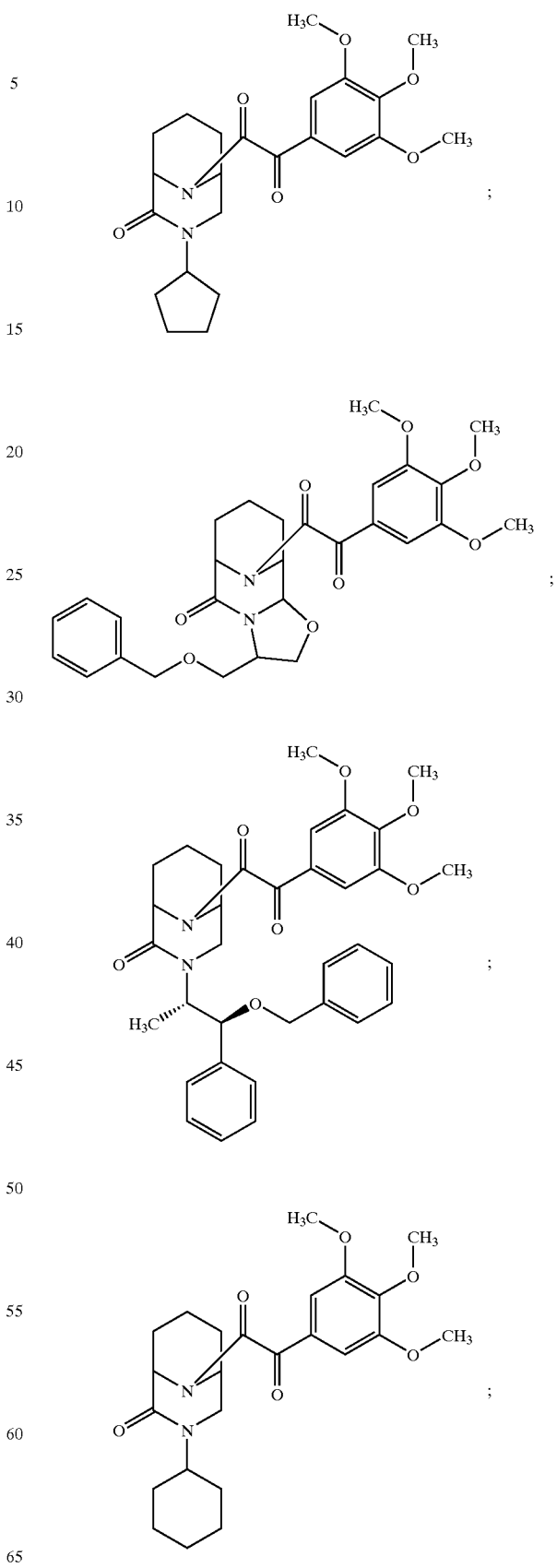

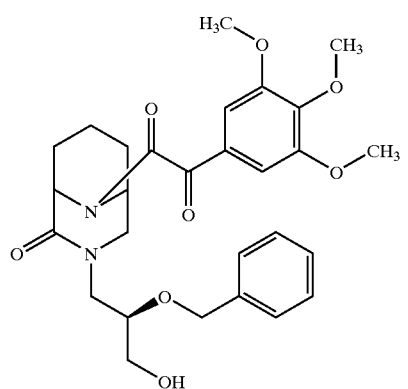
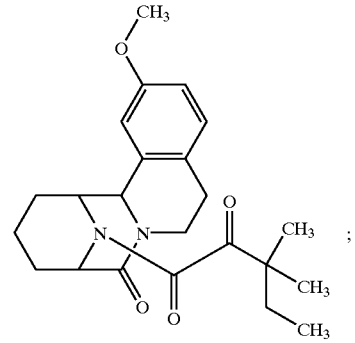
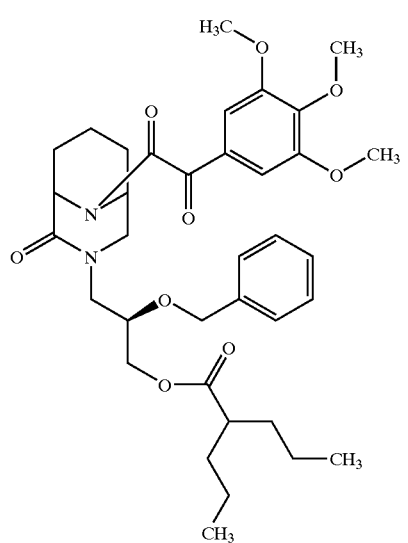
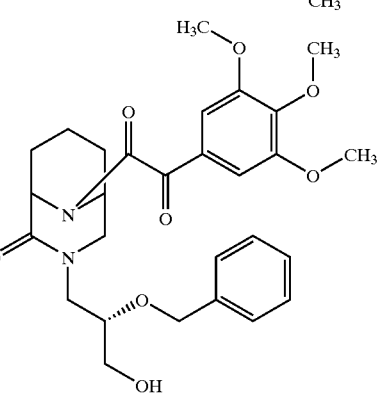
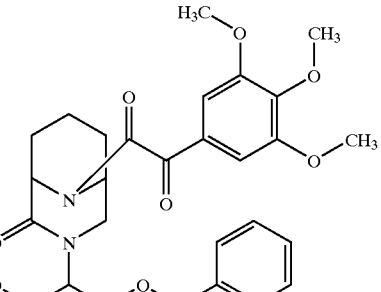
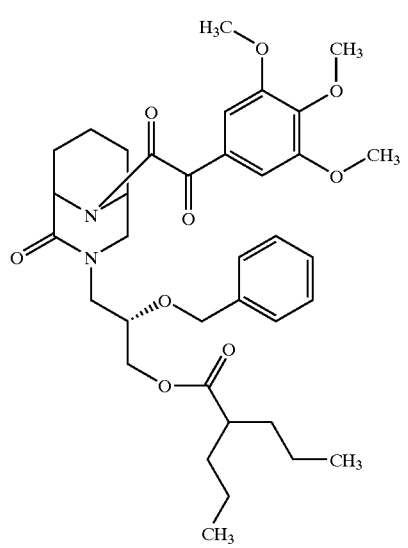
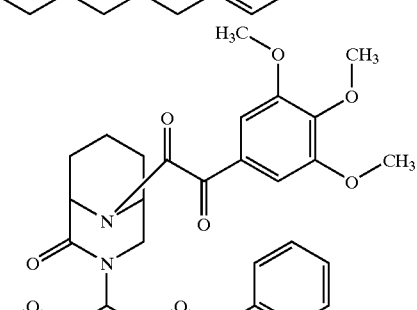
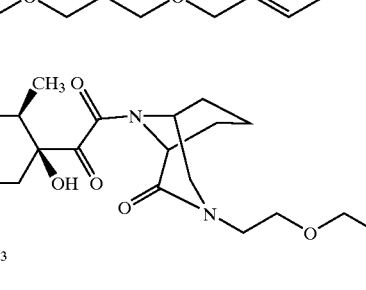

121
-continued
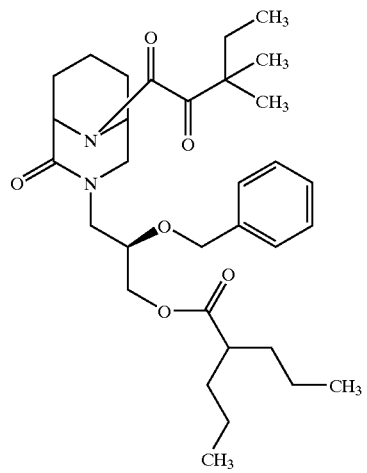
;
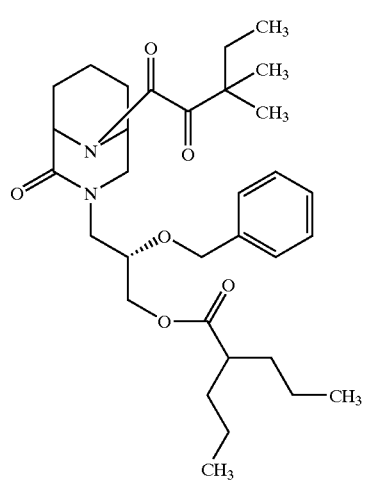
;
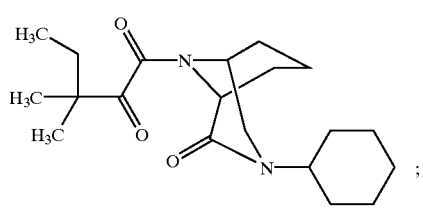
;
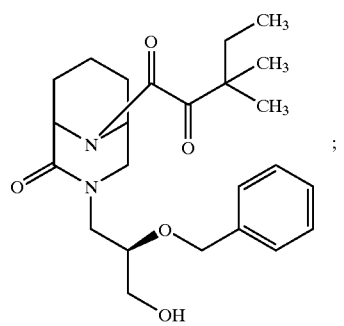
;
122
-continued
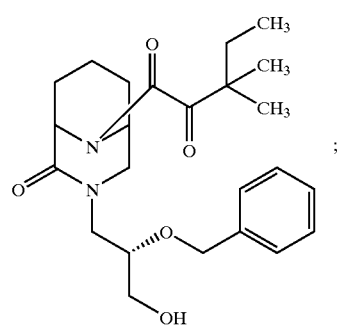
;
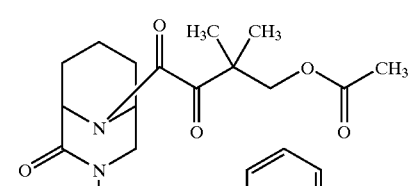
;
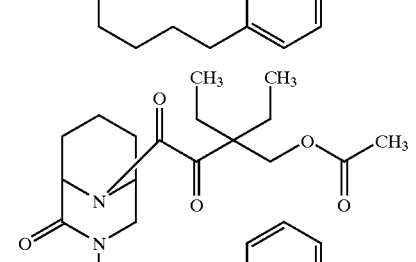
;
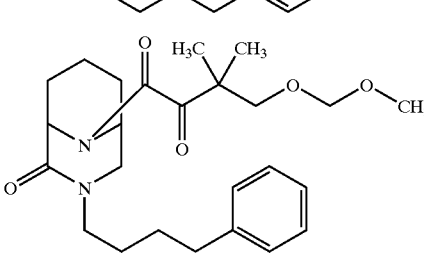
;
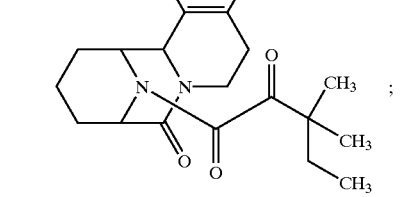
;

123
-continued
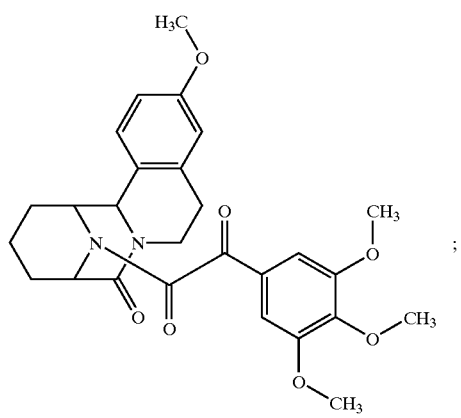
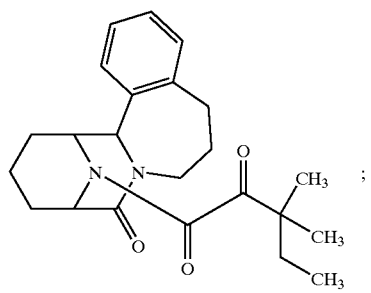
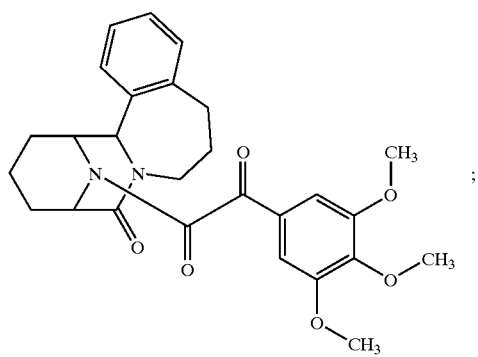
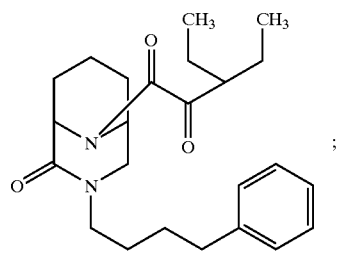
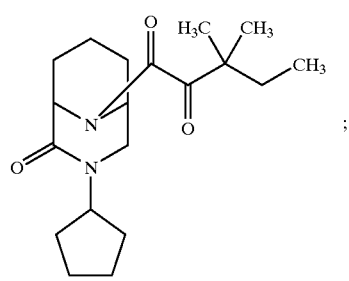
124
-continued
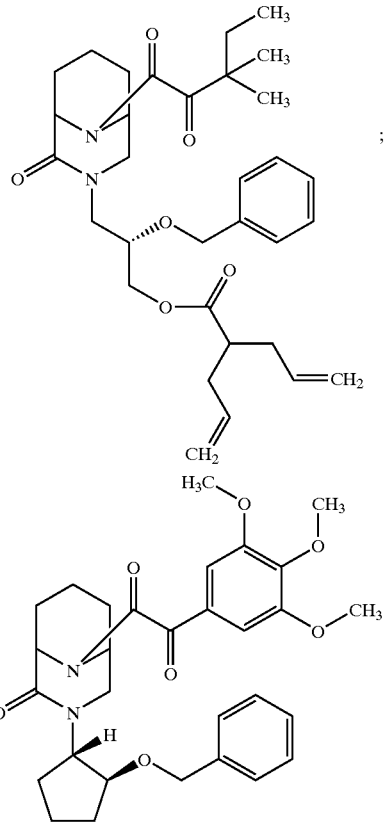
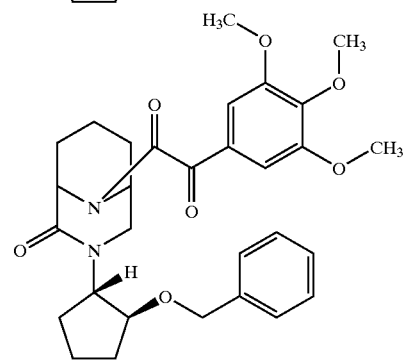
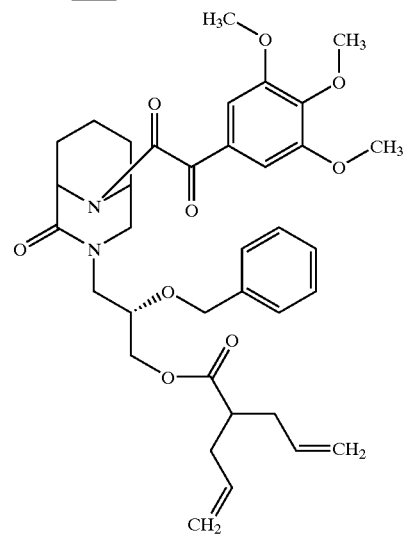

125
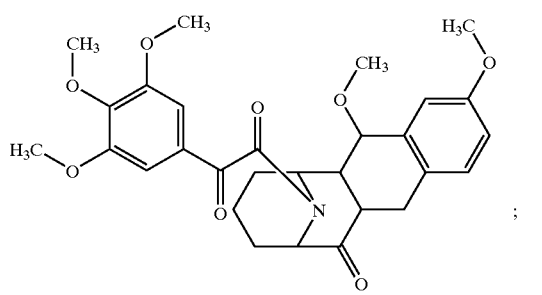
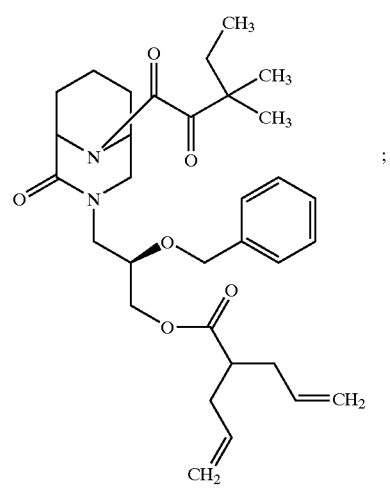
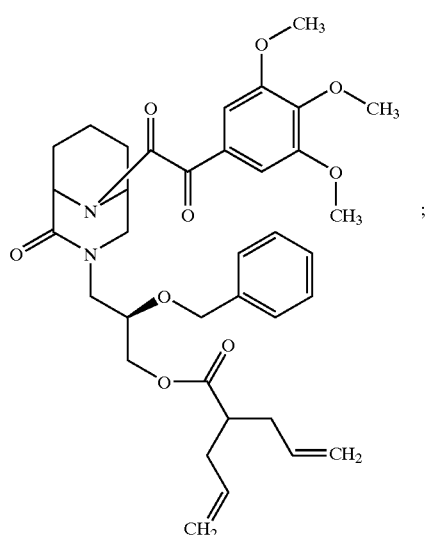
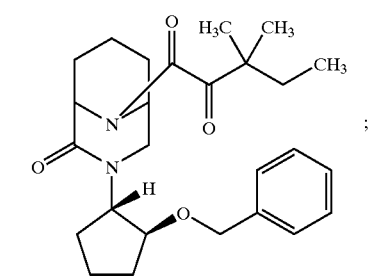
126
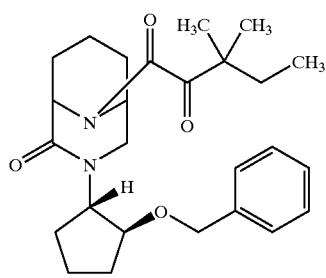
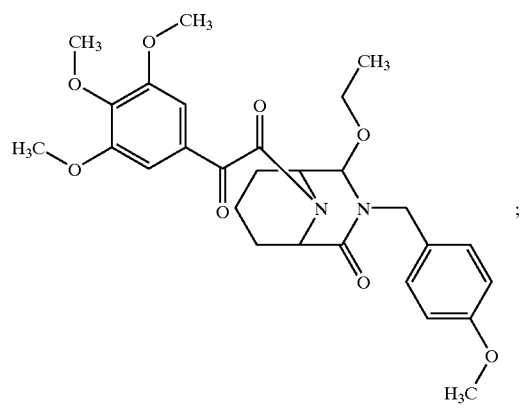
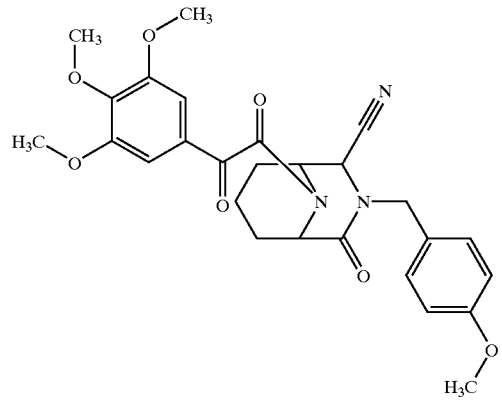
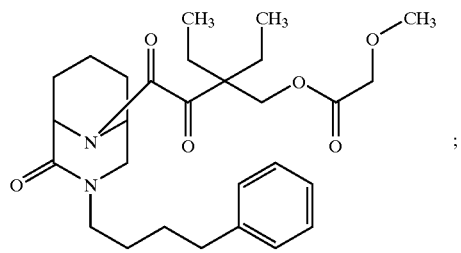
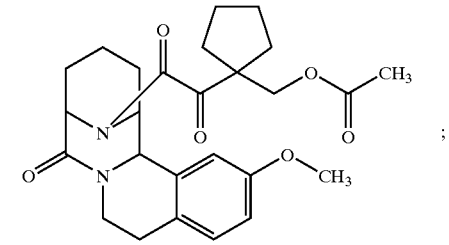

127
-continued
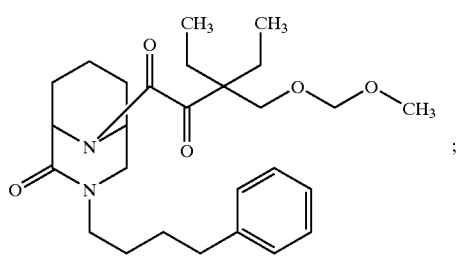
;
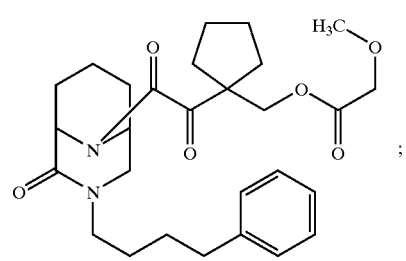
;
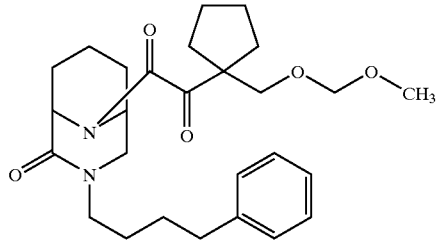
;
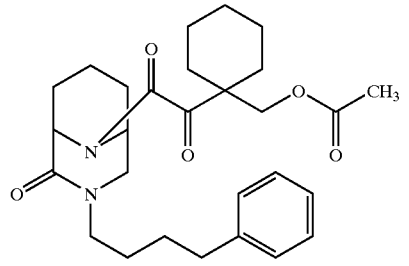
;
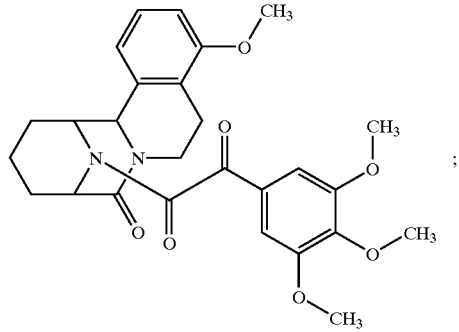
;
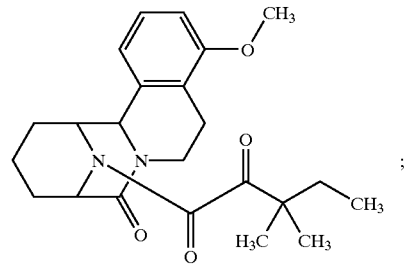
;
128
-continued
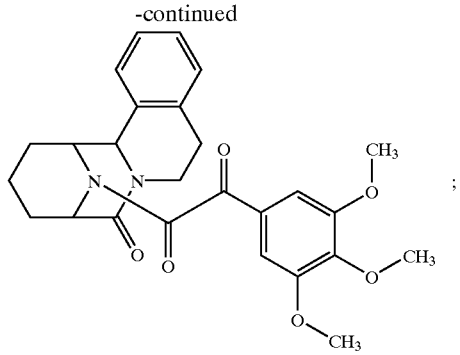
;
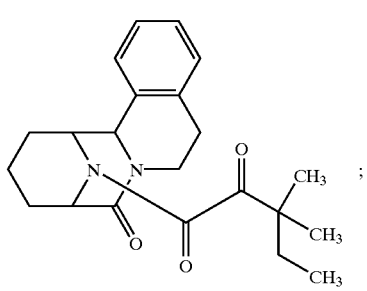
;
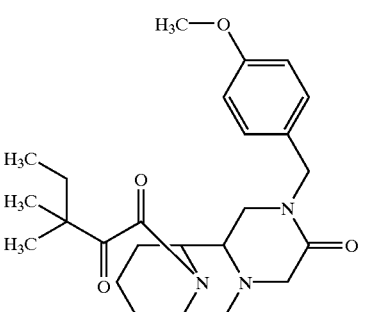
;
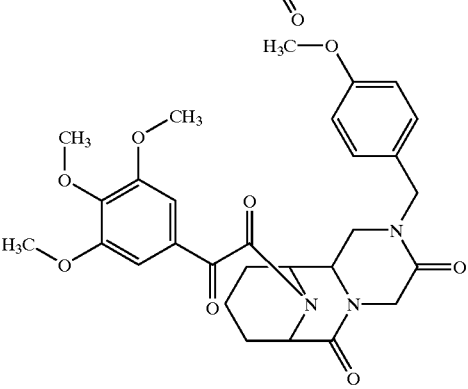
;
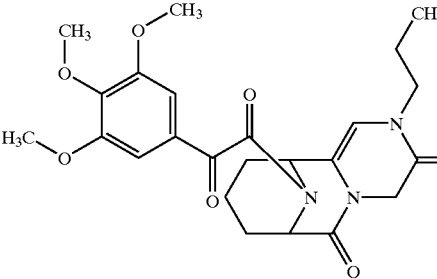
;

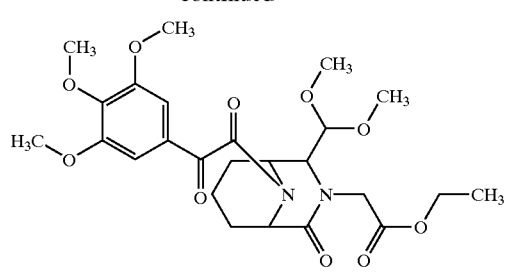
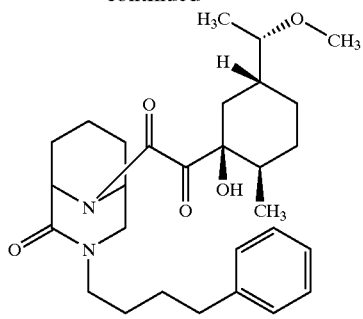
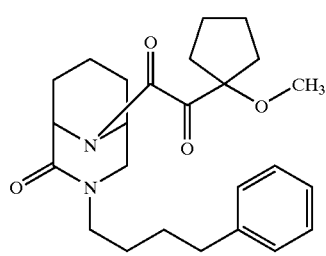
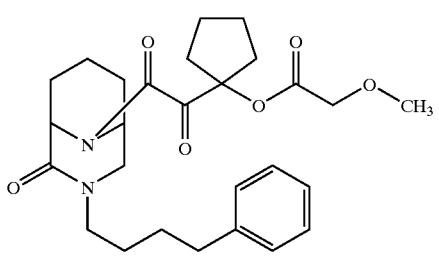
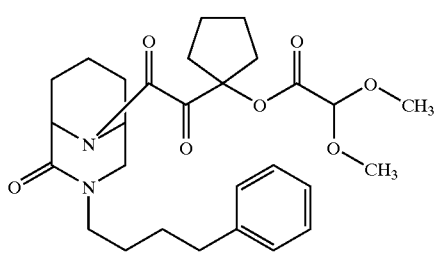
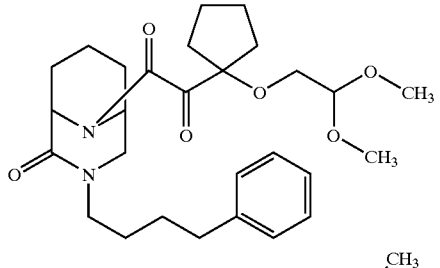
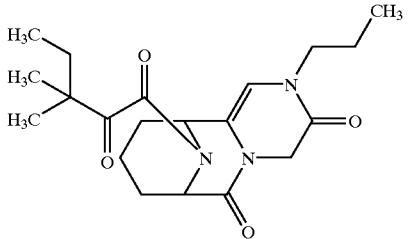

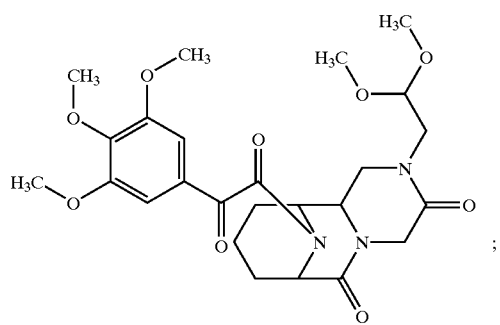
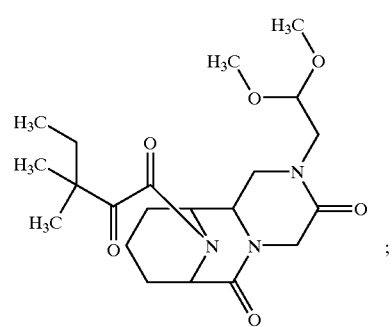
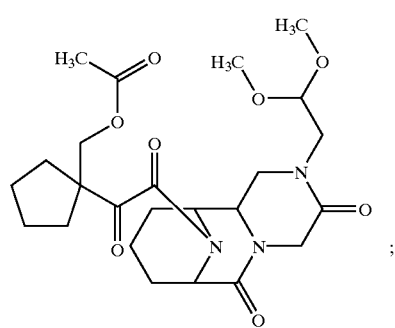
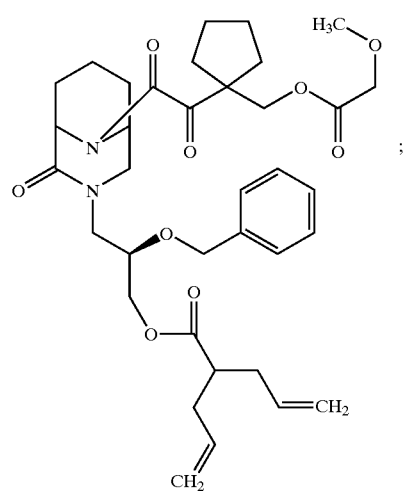
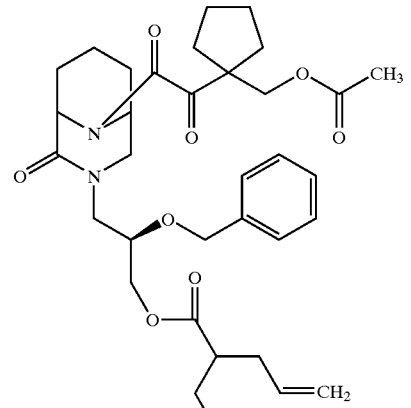
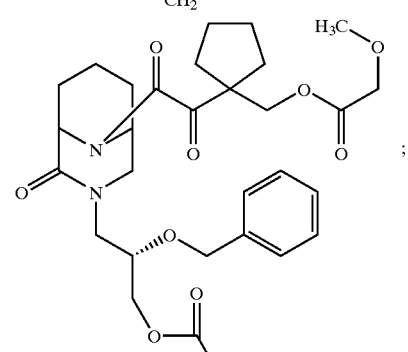
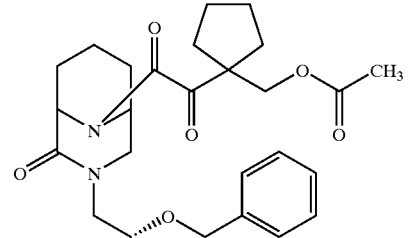
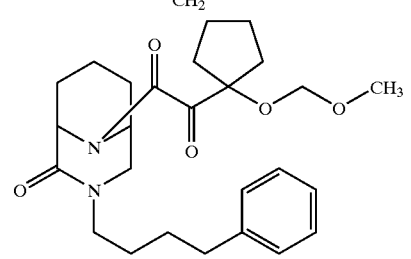

133
-continued
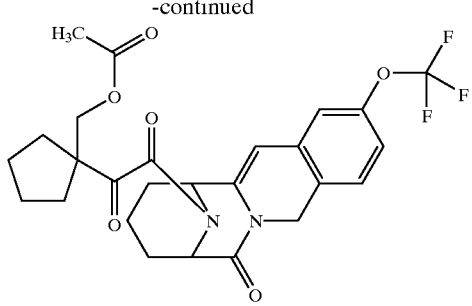
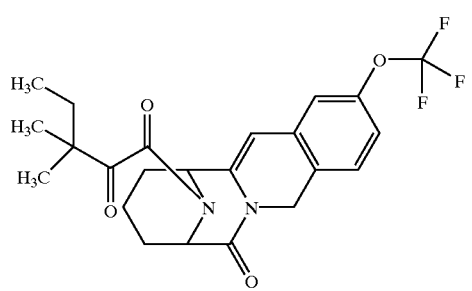
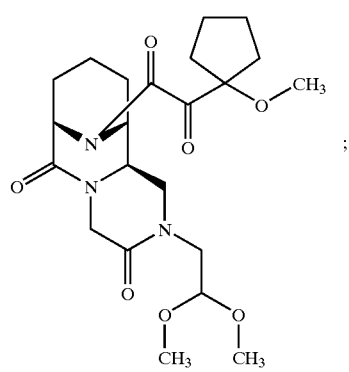
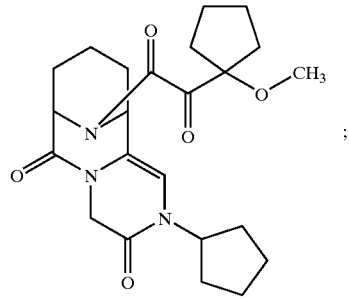
134
-continued
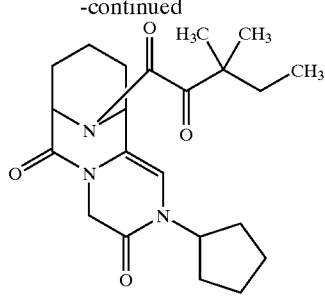
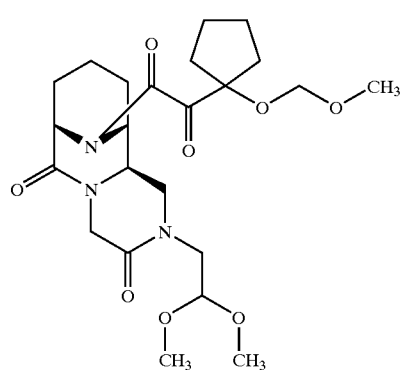
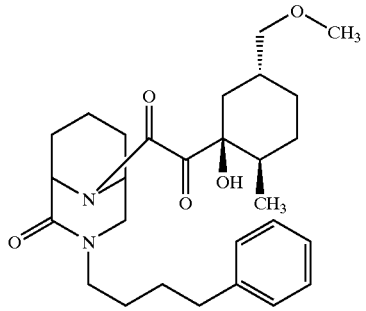
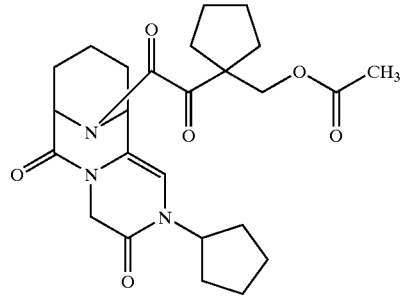
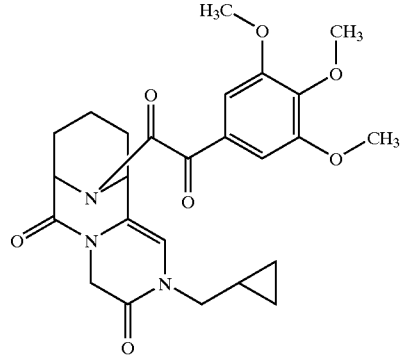

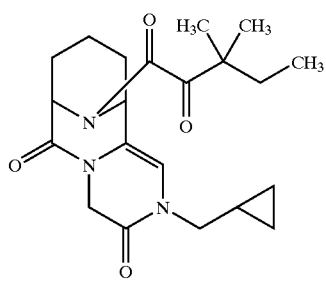;
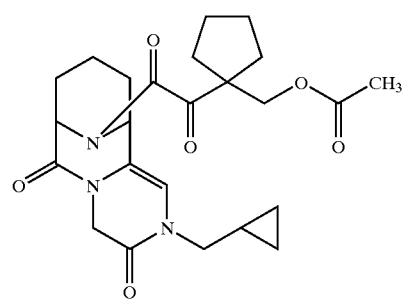;
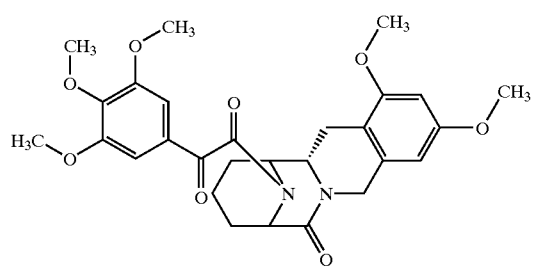;
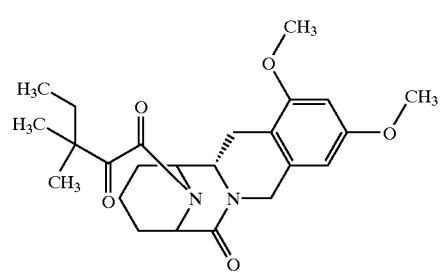;
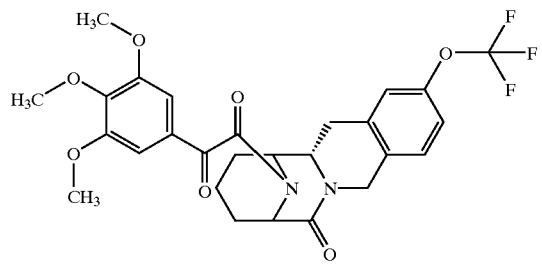;
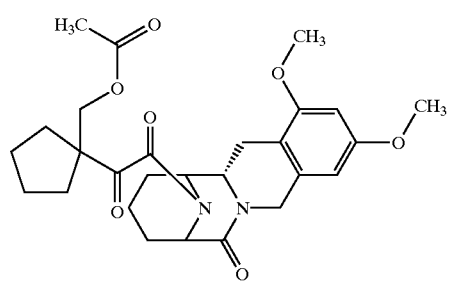;
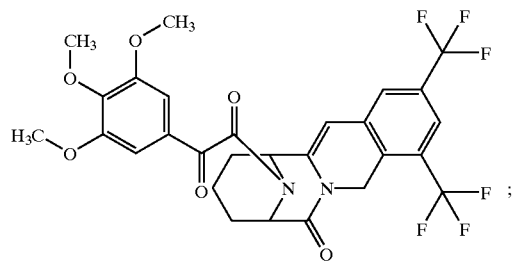;
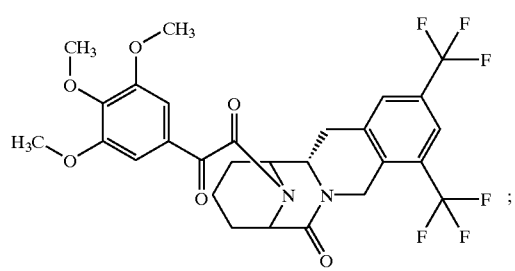;
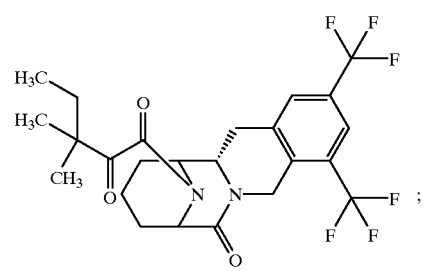;
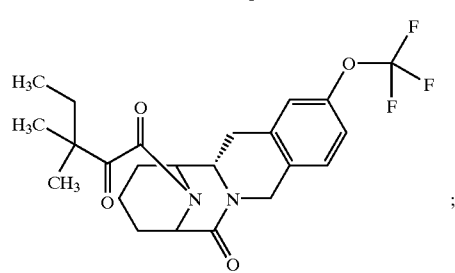;
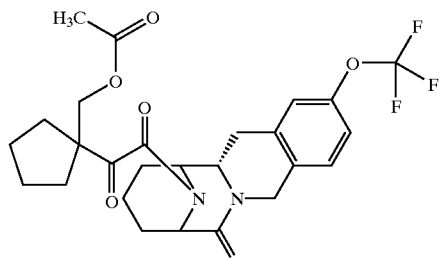;
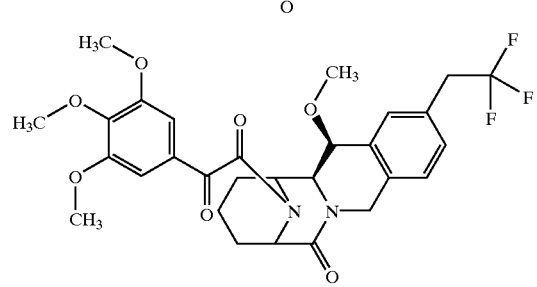;

137
-continued
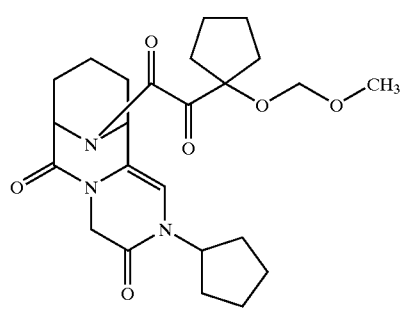
;
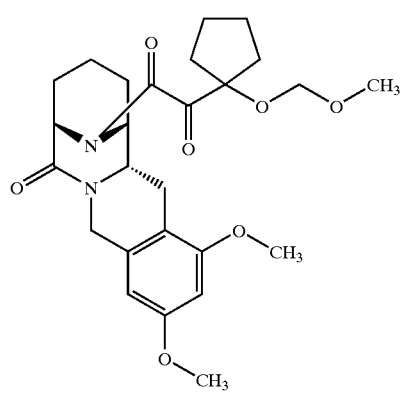
;
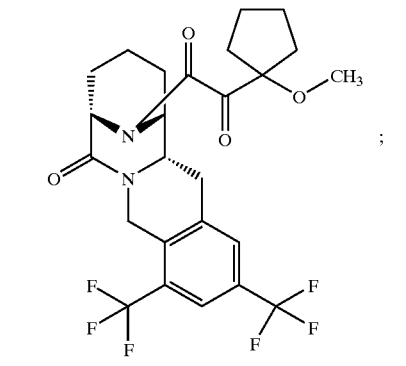
;
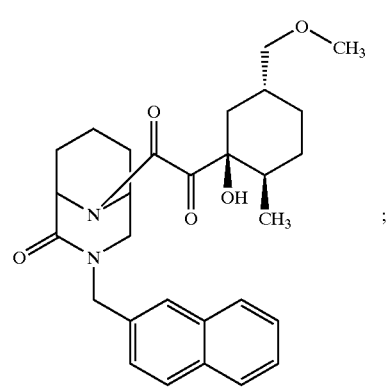
;
138
-continued
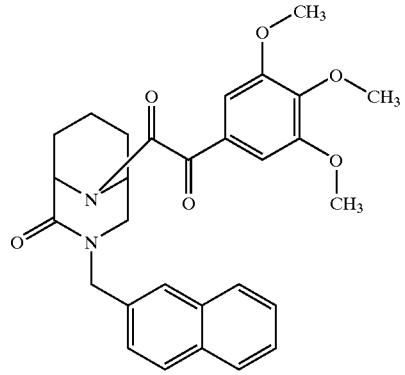
;
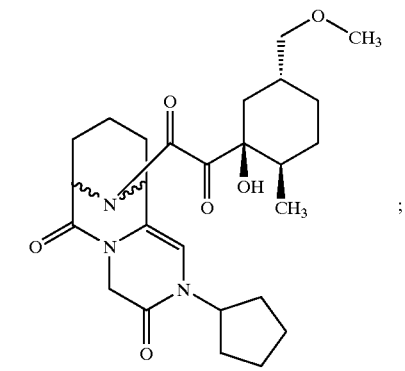
;
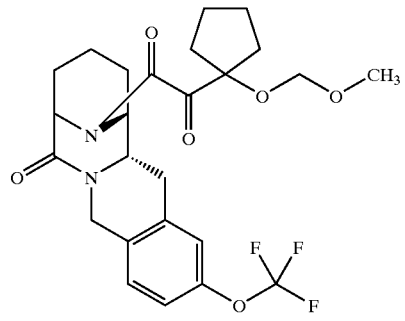
;
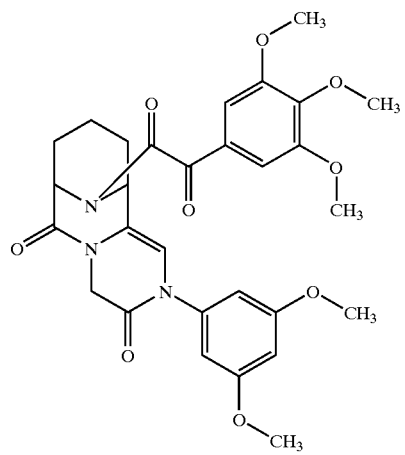
;

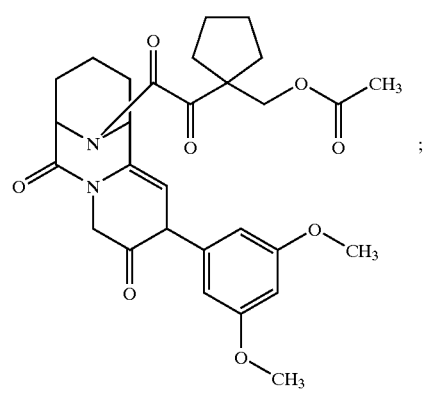
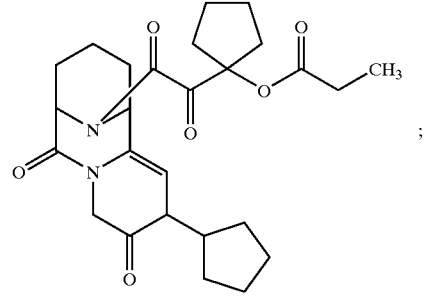
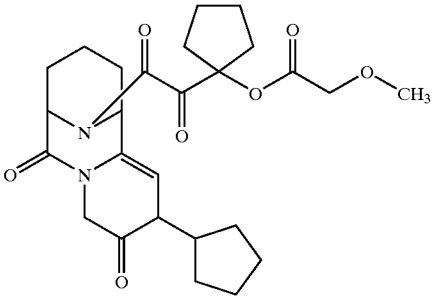
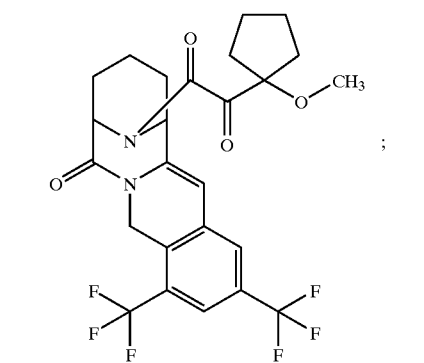
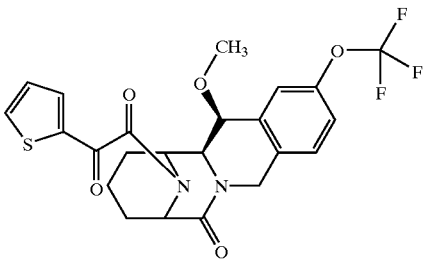
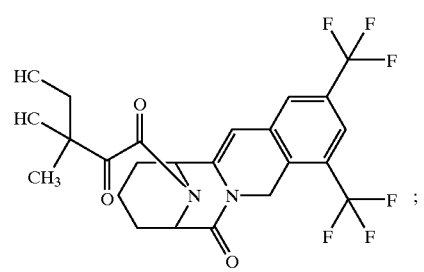
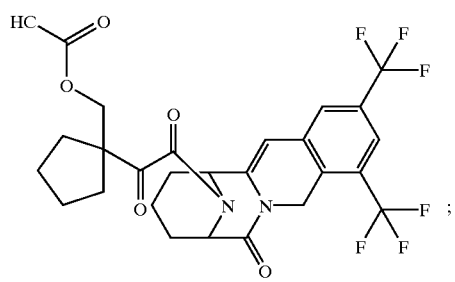
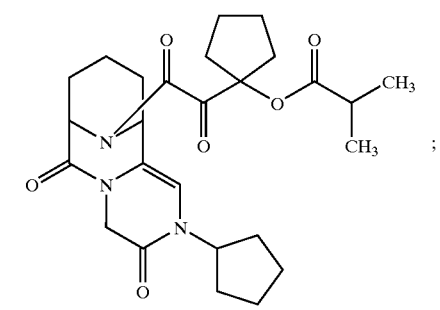
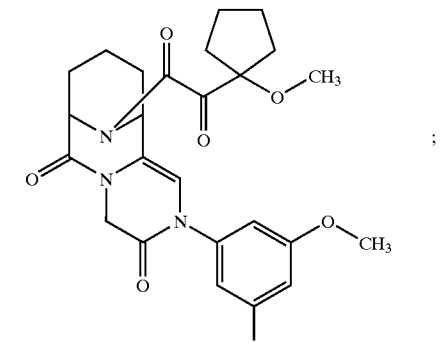
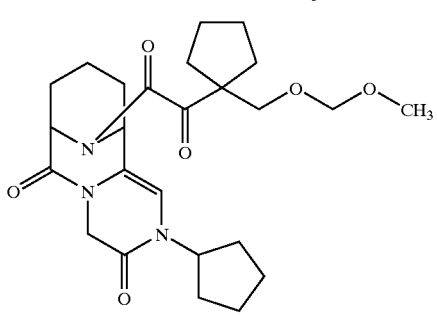

-continued
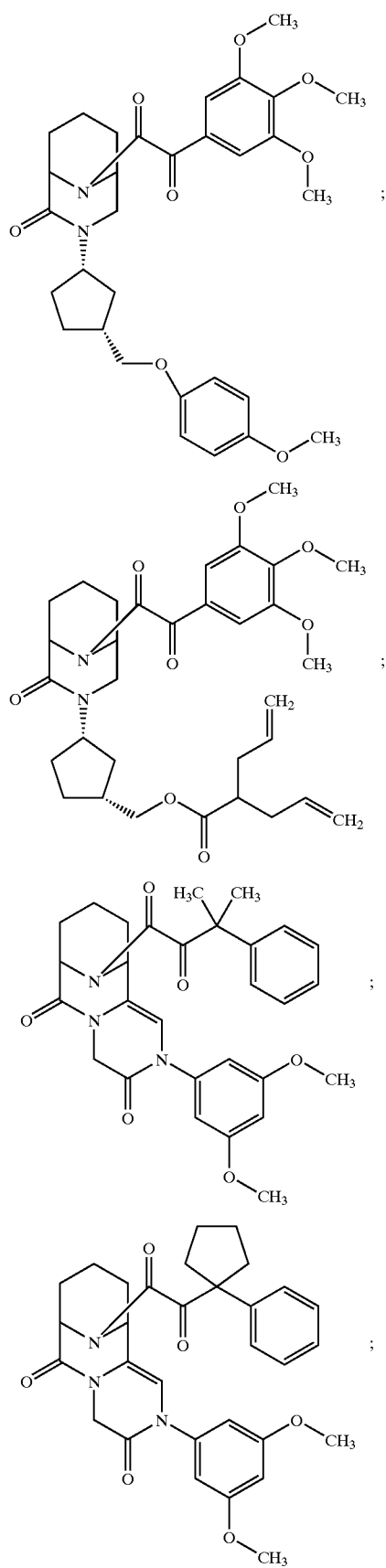
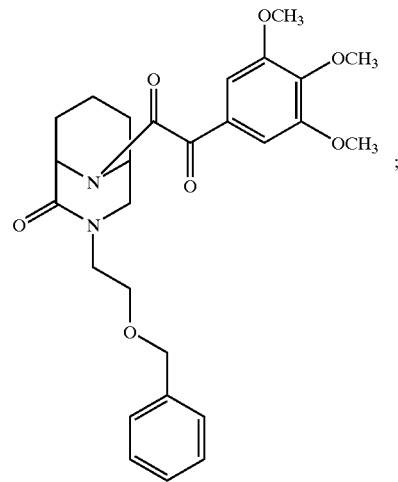
and
or a pharmaceutically acceptable salt of said compound.
15. A compound selected from the group consisting of:

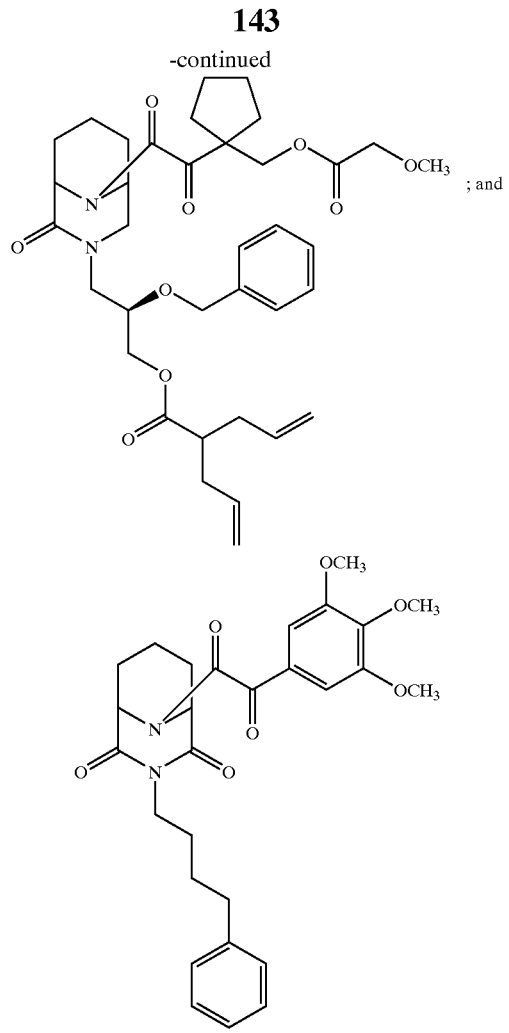

; and or a pharmaceutically acceptable salt of said compound.

16. A pharmaceutical composition comprising a therapeutically effective amount of at least one compound of claim 1 and a pharmaceutically acceptable carrier.

17. A process of making a compound of claim 1, comprising:

(a) converting a compound of formula (III-a):

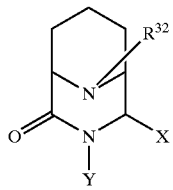

(III-a)

wherein:

R$^{32}$ is selected from the group consisting of optionally substituted alkyl, alkenyl, aryl, cycloalkyl, cycloalkenyl,

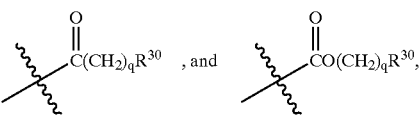

where q is 0 or 1, and R$^{30}$ is an alkyl or aryl group unsubstituted or substituted with one or more substituents independently selected from the group consisting of hydroxyl, C$_1$–C$_6$ alkyl, C$_2$–C$_6$ alkenyl, C$_1$–C$_4$ alkyloxy, C$_2$–C$_4$ alkenyloxy, benzyloxy, phenoxy, and phenyl;

X is: hydrogen; cyano; C$_1$–C$_2$ alkyloxy; dimethoxymethyl; or oxygen, where when X is oxygen, the bond connecting X to the ring carbon atom is a double bond; and Y is hydrogen or an alkyl, alkenyl, benzyl, or cycloalkyl group unsubstituted or substituted with one or more substituents independently selected from the group consisting of: alkyl; aryl; alkoxy; hydroxyalkyl; aryloxy; alkenyloxy; hydroxy; benzyloxy; phenoxy; (CH$_2$)$_p$—O—W$^2$ or (CH$_2$)$_p$—N—W$^2$ where p is 0, 1, or 2, and W$^2$ is R$^3$ or C(O)R$^3$, where R$^3$ is an aryl, alkyl, or alkenyl group unsubstituted or substituted with one or more substituents independently selected from the group consisting of aryl, alkyl, and alkoxy; and (CH$_2$)$_{p'}$—C(O)—O—W$^{2'}$ and (CH$_2$)$_{p'}$—C(O)—N—W$^{2'}$, where p' is 0, 1, or 2, and W$^{2'}$ is an alkyl;

or X and Y, together with the carbon ring atom and nitrogen heteroatom to which they are respectively bonded, form a 5- to 7-membered saturated or unsaturated heterocyclic ring unsubstituted or substituted with one or more substituents J, K, and L; where J, K, and L represent substituents independently selected from the group consisting of oxygen, and C$_3$–C$_5$ cycloalkyl and C$_1$–C$_5$ alkyl groups unsubstituted or substituted with one or more substituents independently selected from the group consisting of C$_3$–C$_5$ cycloalkyl, methoxy, methoxyphenyl, and dimethoxyphenyl; or where J and K together form a phenyl ring unsubstituted or substituted with one or more substituents independently selected from the group consisting of methoxy, trifluoromethyl, trifluoromethoxy, and substituents linked to the phenyl ring through oxygen, nitrogen, carbon or sulfur and independently selected from the group consisting of halogen, hydroxyl, NO$_2$, CF$_3$, C$_1$–C$_6$ alkyl C$_2$–C$_6$ alkenyl, C$_1$–C$_4$ alkyloxy, C$_2$–C$_4$ alkenyloxy, benzyloxy, phenoxy, amino, and phenyl;

under reducing conditions to a compound of formula (III-b):

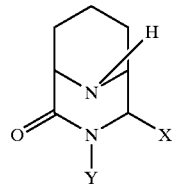

(III-b)

wherein X and Y are as defined above; and (b) coupling said compound of formula (III-b) with a compound of formula (IV):

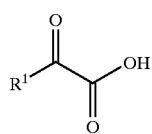
(IV)

wherein R¹ is: hydrogen; an aryl group unsubstituted or substituted with one or more substituents independently selected from the group consisting of halogen, hydroxyl, $NO_2$, $CF_3$, $C_1$–$C_6$ alkyl, $C_2$–$C_6$ alkenyl, $C_1$–$C_4$ alkyloxy, $C_2$–$C_4$ alkenyloxy, benzyloxy, phenoxy, amino, and phenyl; an alkyl or alkenyl group unsubstituted or substituted with one or more substituents independently selected from the group consisting of $C_1$–$C_4$ alkyl, $C_2$–$C_4$ alkenyl, $C_4$–$C_6$ cycloalkenyl, and hydroxy; adamantyl, a $C_3$–$C_8$ cycloalkyl or $C_5$–$C_7$ cycloalkenyl group unsubstituted or substituted with one or more substituents independently selected from the group consisting of $C_1$–$C_4$ alkyl, $C_2$–$C_4$ alkenyl, $C_1$–$C_4$ alkyloxy, and hydroxy; or $C(R^{11})(R^{12})(R^{13})$, where $R^{11}$ and $R^{12}$ are each independently lower alkyl, or $R^{11}$ and $R^{12}$ together with the atom to which they are bound form cycloalkyl, and $R^{13}$ is H, OH, lower alkyl, aryl, or $(CH_2)_n$—O—$W^1$, where n is 0, 1, 2, or 3, and $W^1$ is $R^2$ or $C(O)R^2$, with $R^2$ being $C_1$–$C_3$ alkyl unsubstituted or substituted with one or two methoxy groups.

18. A process according to claim 17, wherein the compound of formula (III-a) is selected from the group consisting of:

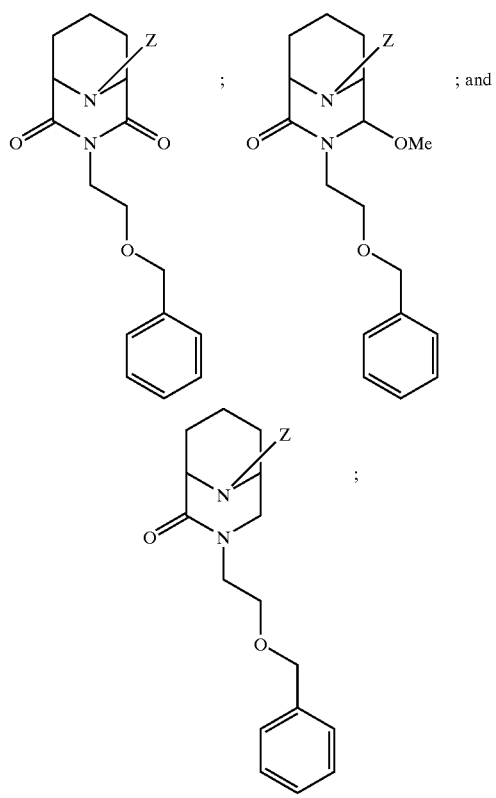

where Z is benzyloxycarbonyl.

19. A process according to claim 17, wherein the compound of formula (III-a) is selected from the group consisting of:

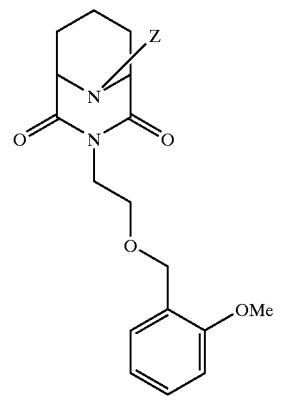

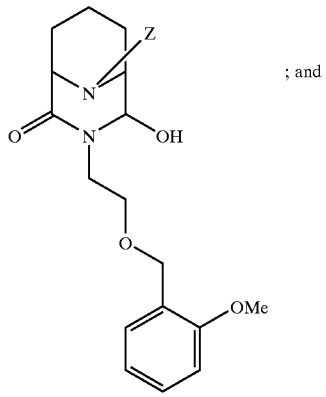

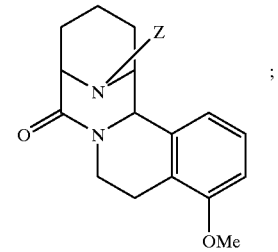

where Z is benzyloxycarbonyl.

20. A process according to claim 17, wherein the compound of formula (III-a) is

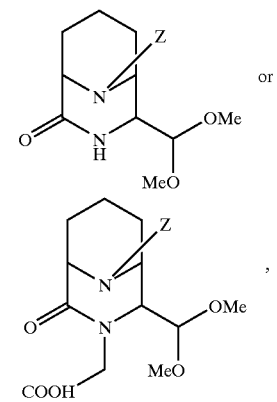

where Z is benzyloxycarbonyl.

21. A process according to claim 17, wherein the compound of formula (III-a) is selected from the group consisting of:

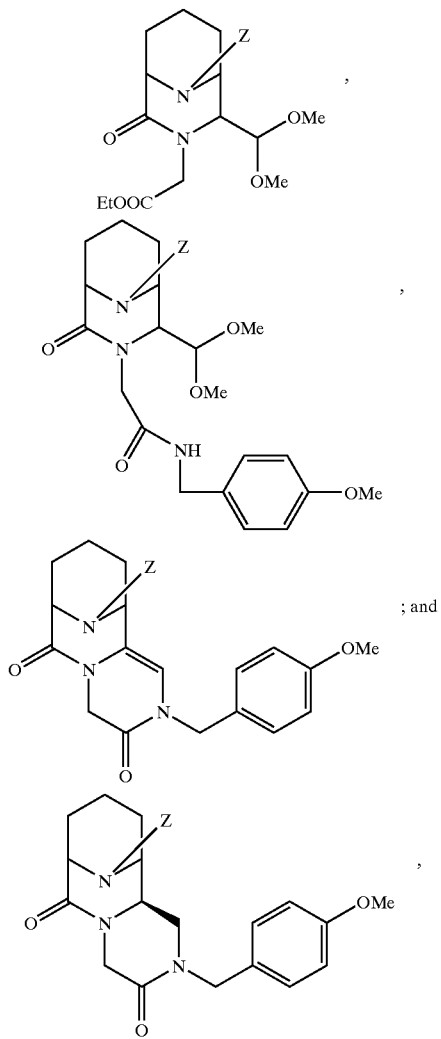

where Z is benzyloxycarbonyl.

22. A process according to claim 17, further comprising: converting a compound of formula (I):

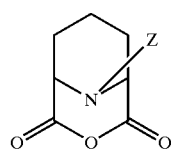
(II)

wherein Z is

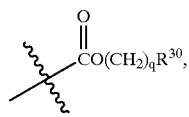

where q is 0 or 1, and $R^{30}$ is an alkyl or aryl group unsubstituted or substituted with one or more substituents independently selected from the group consisting of hydroxyl, $C_1$–$C_6$ alkyl, $C_2$–$C_6$ alkenyl, $C_1$–$C_4$ alkyloxy, $C_2$–$C_4$ alkenyloxy, benzyloxy, phenoxy, and phenyl, to said compound of formula (III-a).

23. A compound of formula:

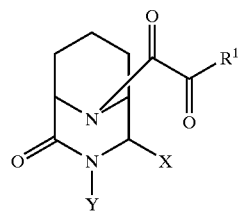

wherein:

$R^1$ is: hydrogen; an aryl group unsubstituted or substituted with one or more substituents independently selected from the group consisting of halogen, hydroxyl, $NO_2$, $CF_3$, $C_1$–$C_6$ alkyl, $C_2$–$C_6$ alkenyl, $C_1$–$C_4$ alkyloxy, $C_2$–$C_4$ alkenyloxy, benzyloxy, phenoxy, amino, and phenyl; an alkyl or alkenyl group unsubstituted or substituted with one or more substituents independently selected from the group consisting of $C_1$–$C_4$ alkyl, $C_2$–$C_4$ alkenyl, $C_4$–$C_6$ cycloalkenyl, and hydroxy; adamantyl, $C_3$–$C_8$ cycloalkyl or $C_5$–$C_7$ cycloalkenyl group unsubstituted or substituted with one or more substituents independently selected from the group consisting of $C_1$–$C_4$ alkyl, $C_2$–$C_4$ alkenyl, $C_1$–$C_4$ alkyloxy, and hydroxy; or $C(R^{11})(R^{12})(R^{13})$, where $R^{11}$ and $R^{12}$ are each independently lower alkyl, or $R^{11}$ and $R^{12}$ together with the atom to which they are bound form cycloalkyl, and $R^{13}$ is H, OH, lower alkyl, aryl, or $(CH_2)_n$—O—$W^1$, where n is 0, 1, 2, or 3, and $W^1$ is $R^2$ or $C(O)R^2$, with $R^2$ being $C_1$–$C_3$ alkyl unsubstituted or substituted with one or two methoxy groups;

X is hydrogen, cyano, $C_1$–$C_2$ alkyloxy, dimethoxymethyl, or =O; and

Y is hydrogen or an alkyl, alkenyl, benzyl, or cycloalkyl group unsubstituted or substituted with one or more substituents independently selected from the group consisting of: alkyl; aryl; alkoxy; hydroxyalkyl; aryloxy; alkenyloxy; hydroxy; benzyloxy; phenoxy; $(CH_2)_p$—O—$W^2$ and $(CH_2)_p$—N—$W^2$ where p is 0, 1, or 2 and $W^2$ is $R^3$ or $C(O)R^3$, where $R^3$ is an aryl, alkyl, or alkenyl group unsubstituted or substituted with one or more substituents independently selected from the group consisting of aryl, alkyl, and alkoxy; and $(CH_2)_{p'}$—C(O)—O—$W^{2'}$ and $(CH_2)_{p'}$—C(O)—N—$W^{2'}$, where p' is 0, 1, or 2, and $W^{2'}$ is an alkyl;

or X and Y, together with the carbon ring atom and nitrogen heteroatom to which they are respectively bonded, form a 5- to 7-membered saturated or unsaturated heterocyclic ring unsubstituted or substituted with one or more substituents J, K, and L; where J, K, and L represent substituents independently selected from the group consisting of oxo, and $C_3$–$C_5$ cycloalkyl and $C_1$–$C_5$ alkyl groups unsubstituted or substituted with one or more substituents independently selected from the group consisting of $C_3$–$C_5$ cycloalkyl, methoxy, methoxyphenyl, and dimethoxyphenyl; or where J and K together form a phenyl ring unsubstituted or substituted with one or more substituents independently selected from the group consisting of methoxy, trifluoromethyl, trifluoromethoxy, and substituents linked to the phenyl ring through oxygen, nitrogen, carbon or sulfur and independently selected from the group consisting of halogen, hydroxyl, $NO_2$, $CF_3$, $C_1-C_6$ alkyl, $C_2-C_6$ alkenyl, $C_1-C_4$ alkyloxy, $C_2-C_4$ alkenyloxy, benzyloxy, phenoxy, amino, and phenyl;
or a pharmaceutically acceptable salt of said compound.
24. A compound selected from the group consisting of:
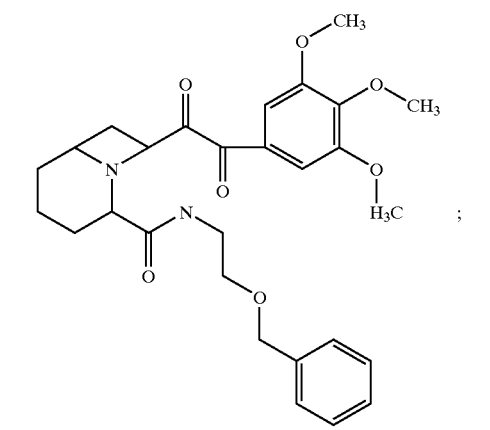
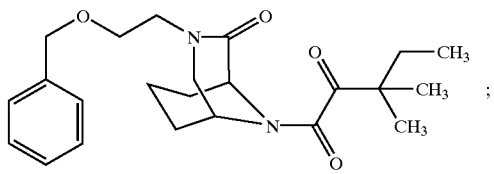
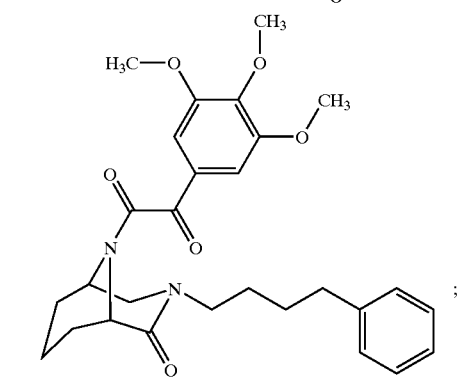
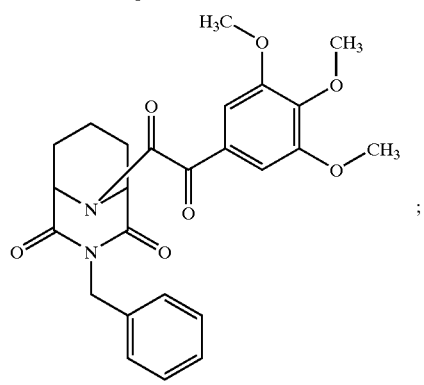
-continued
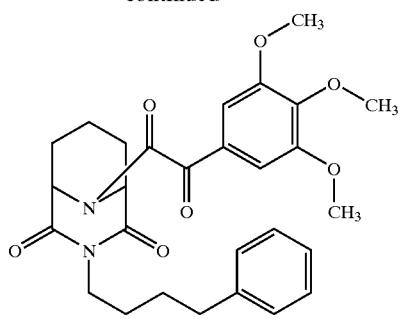
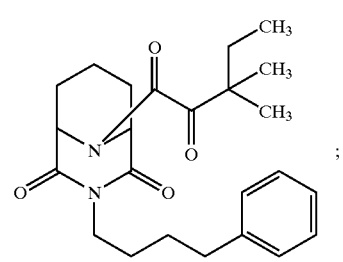
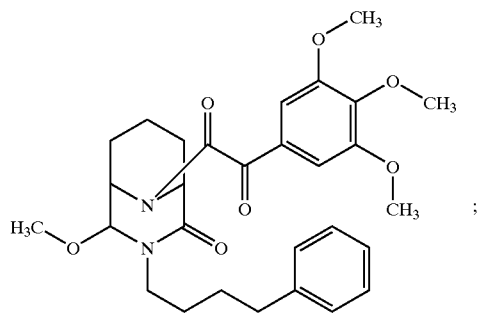
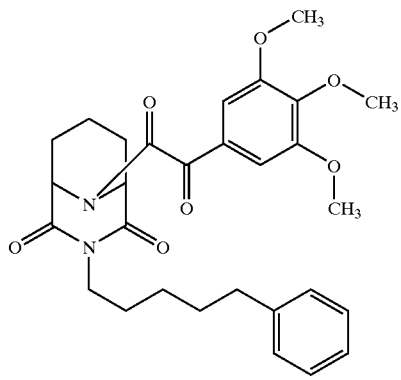
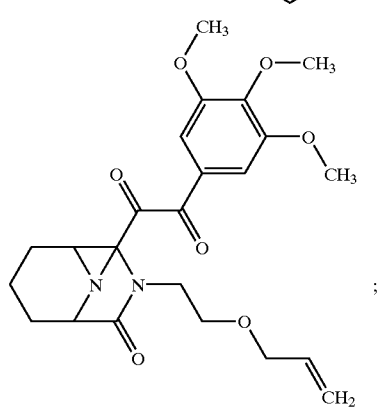

151
-continued
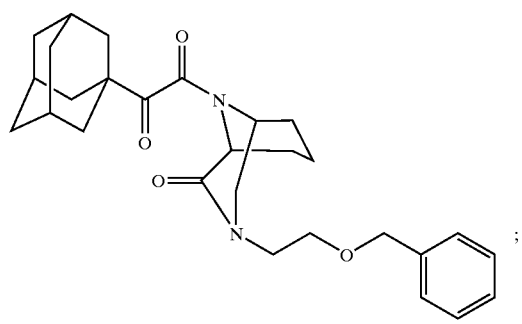
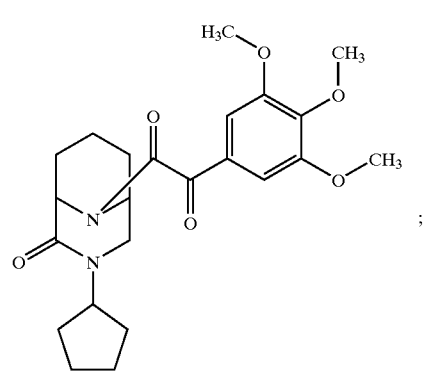
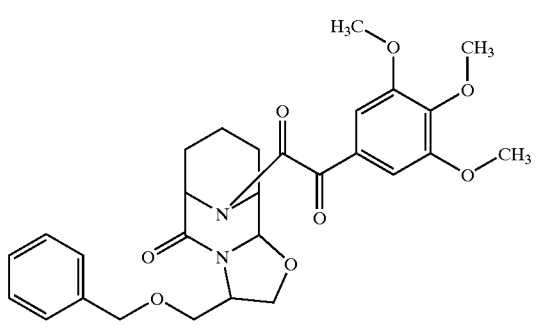
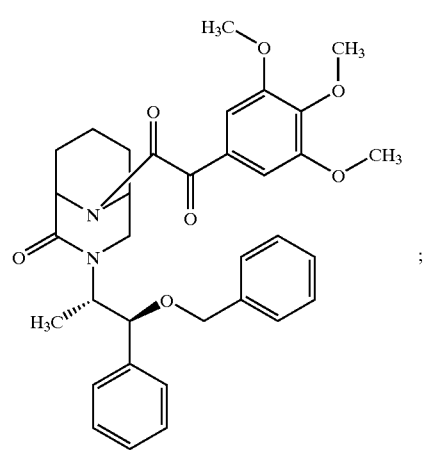
152
-continued
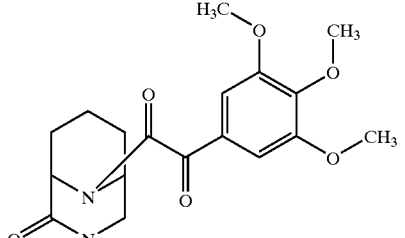
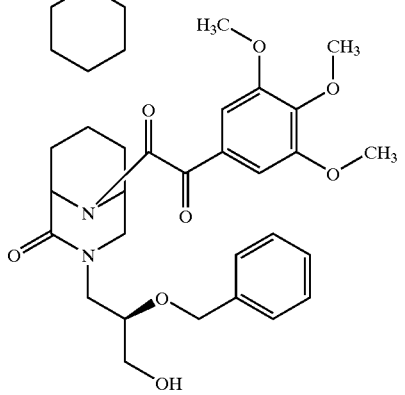
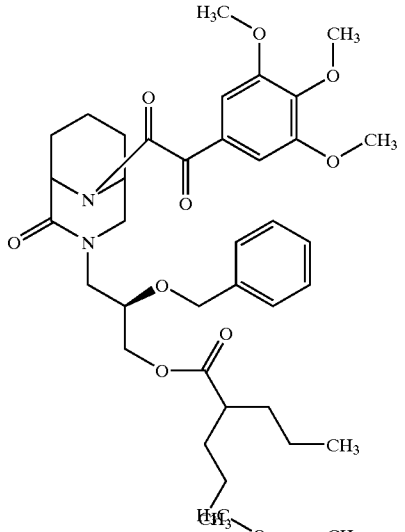
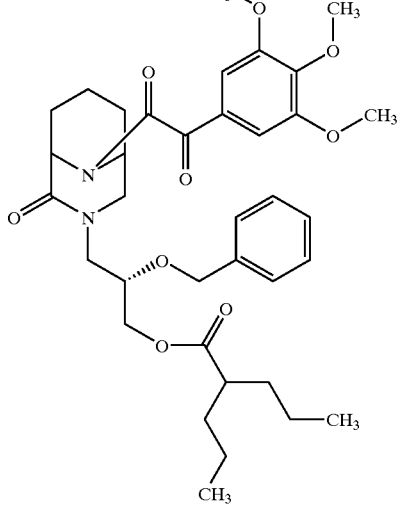

153
-continued
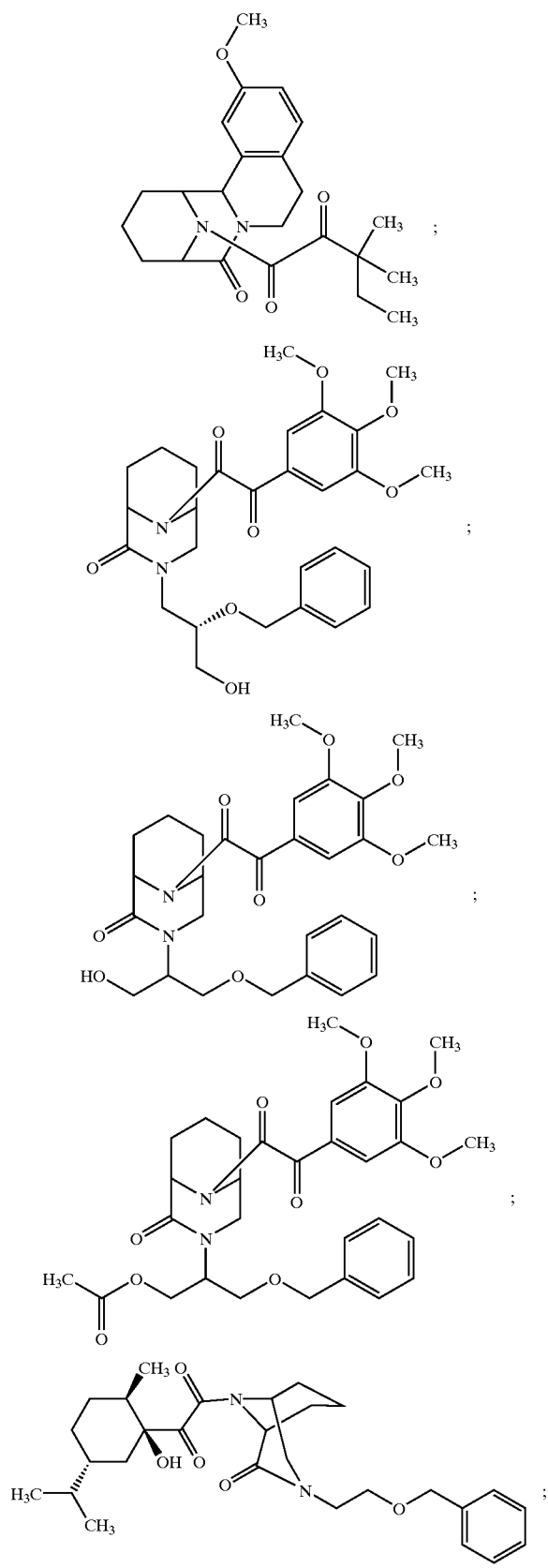
154
-continued
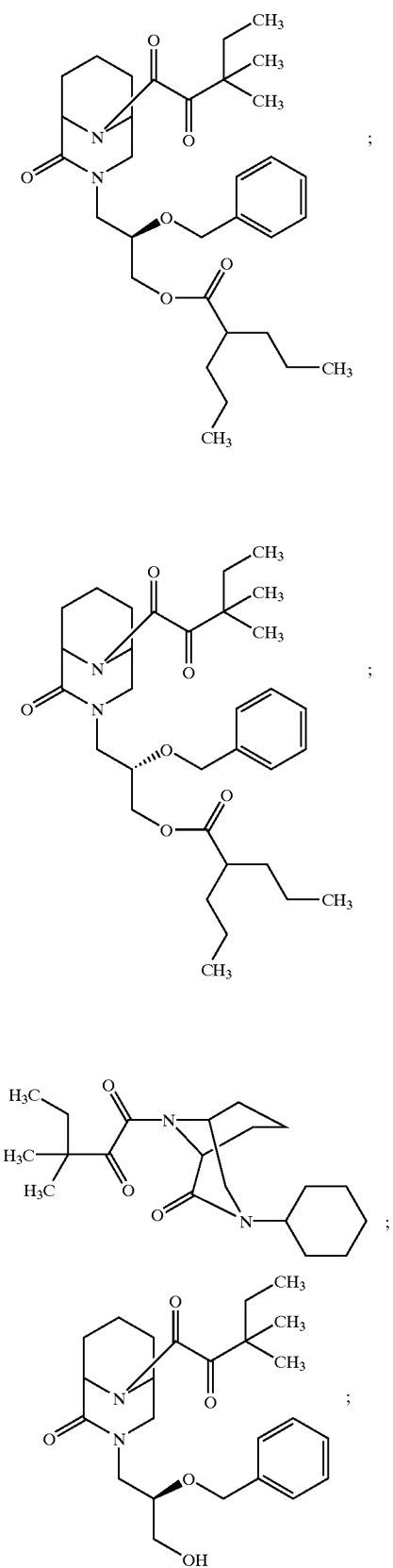

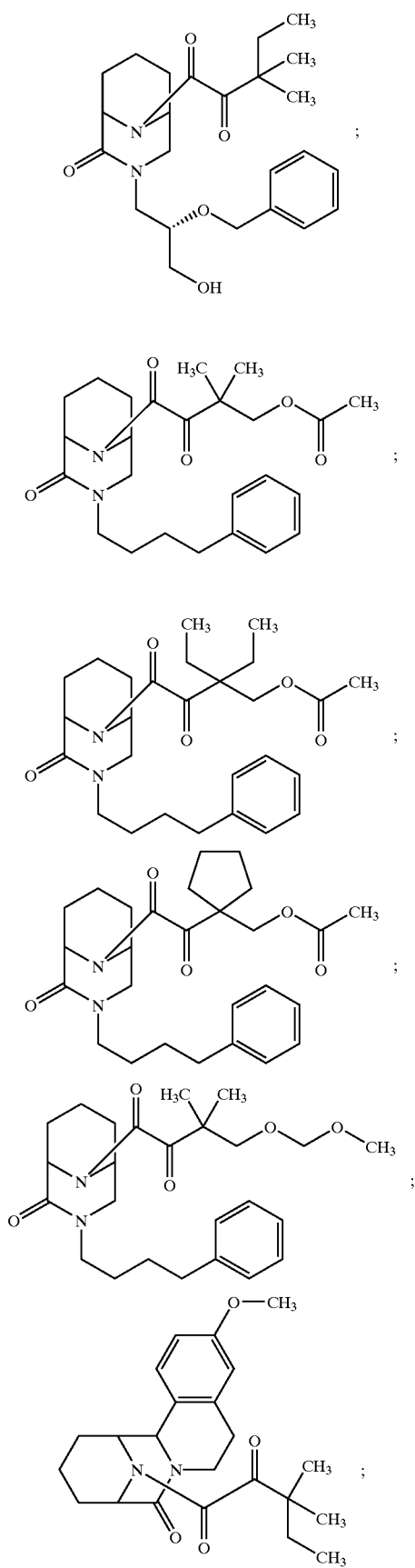

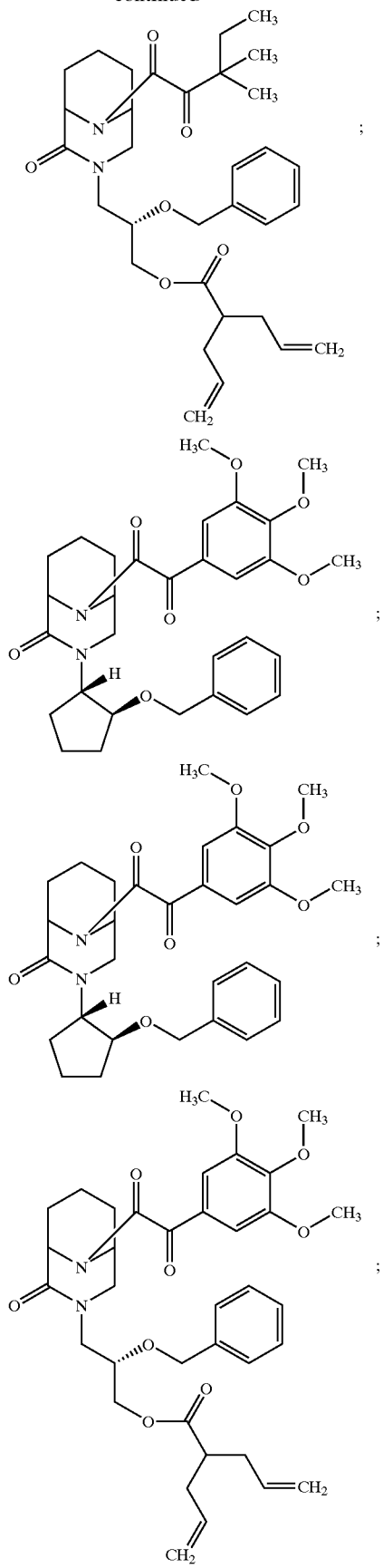
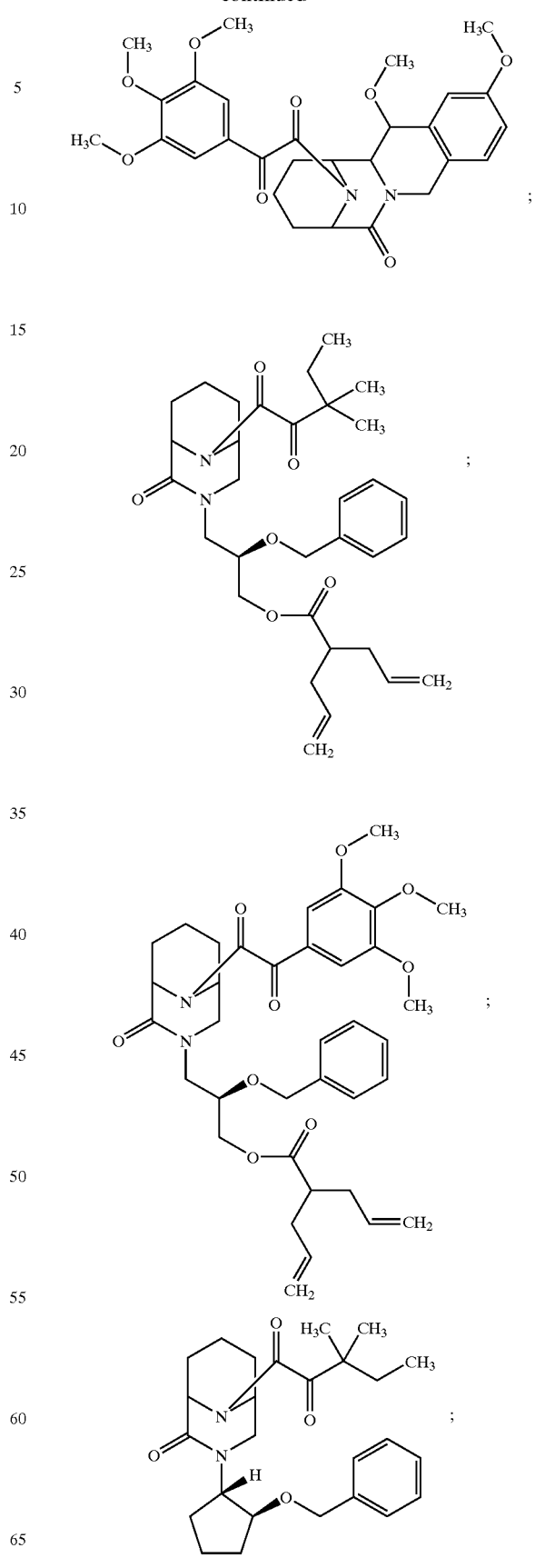

159
-continued
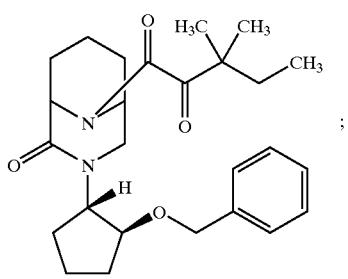
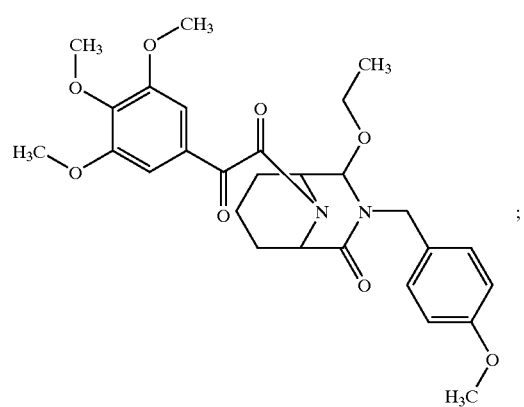
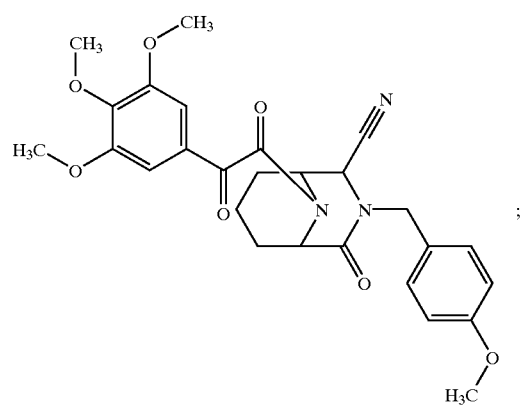
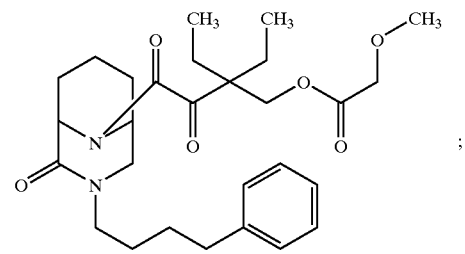
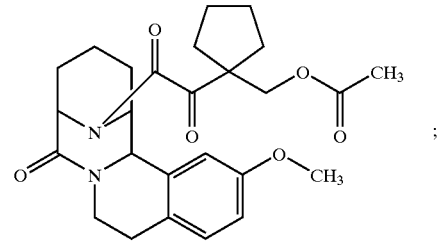
160
-continued
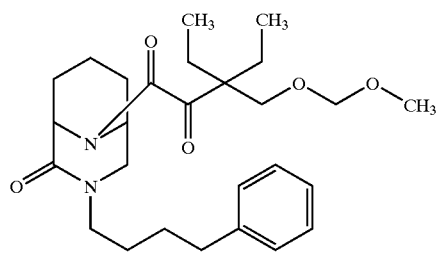
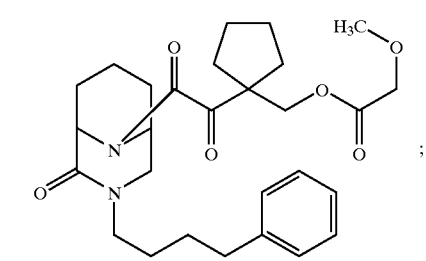
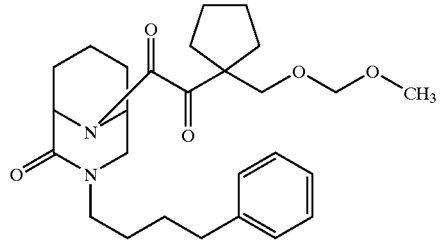
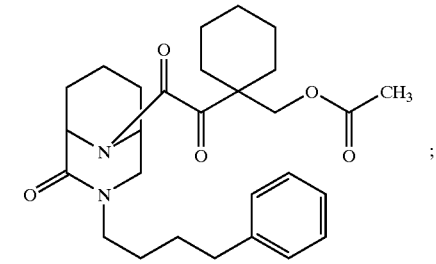
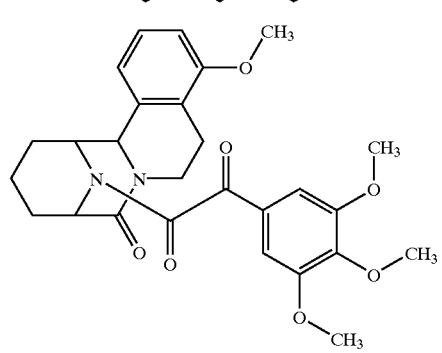
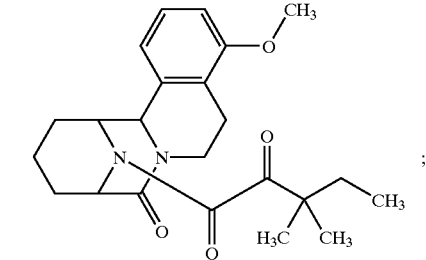

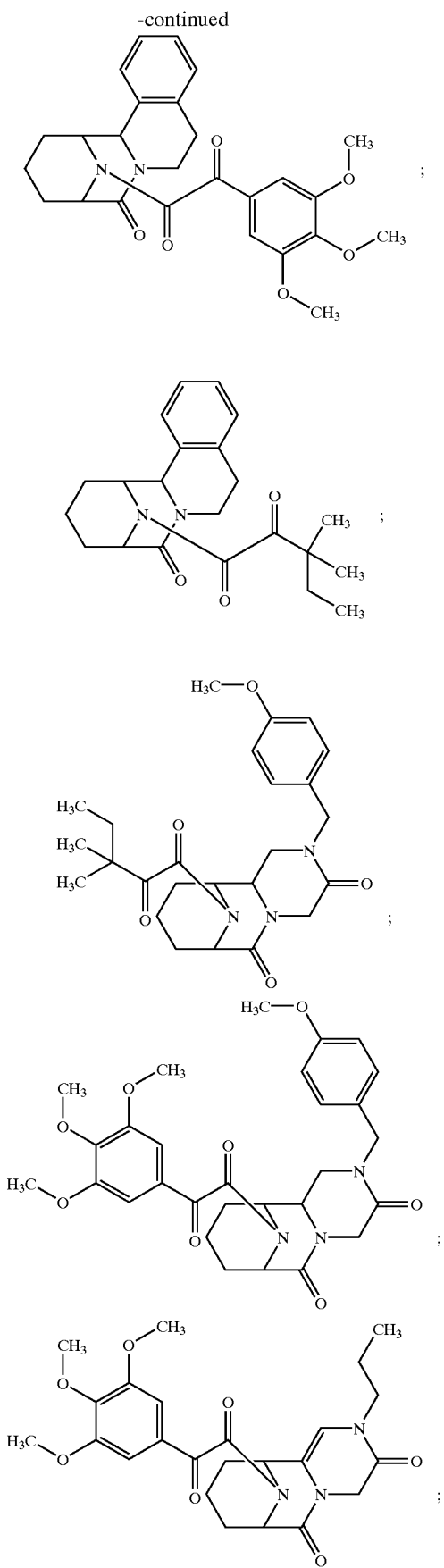
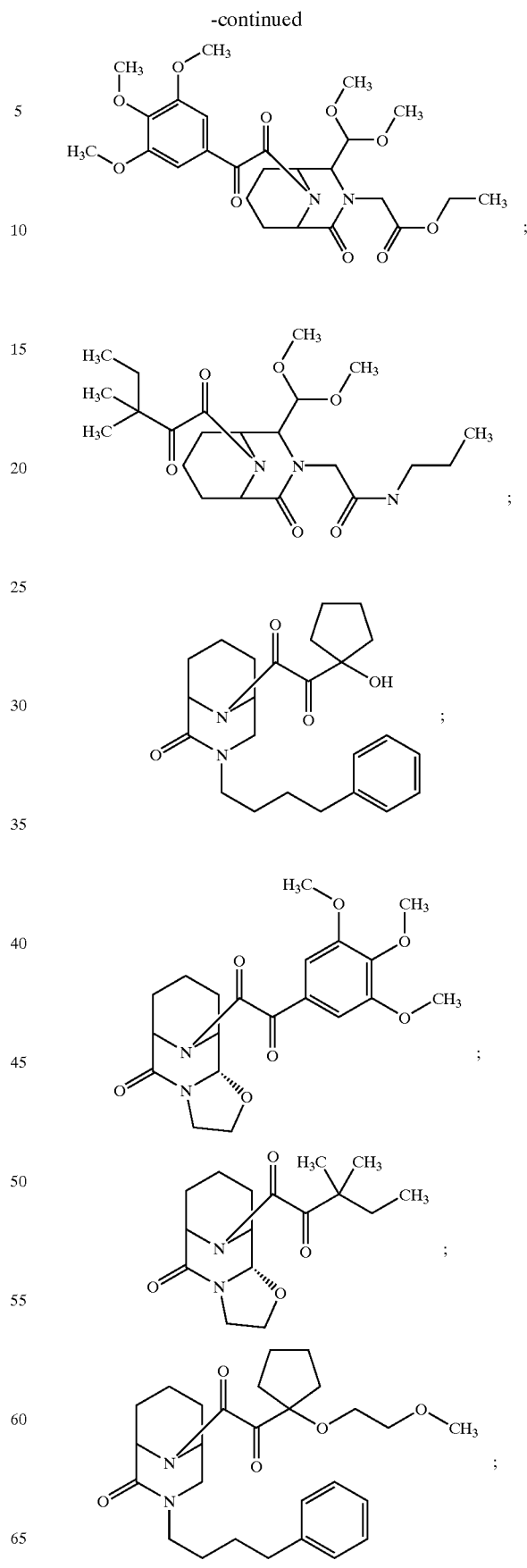

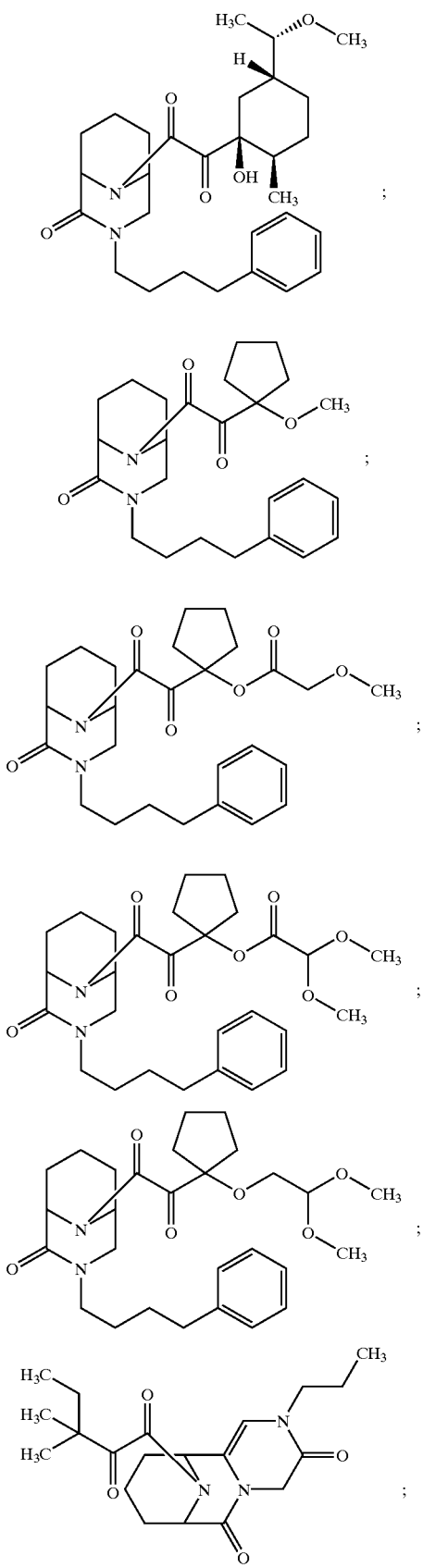

165
-continued
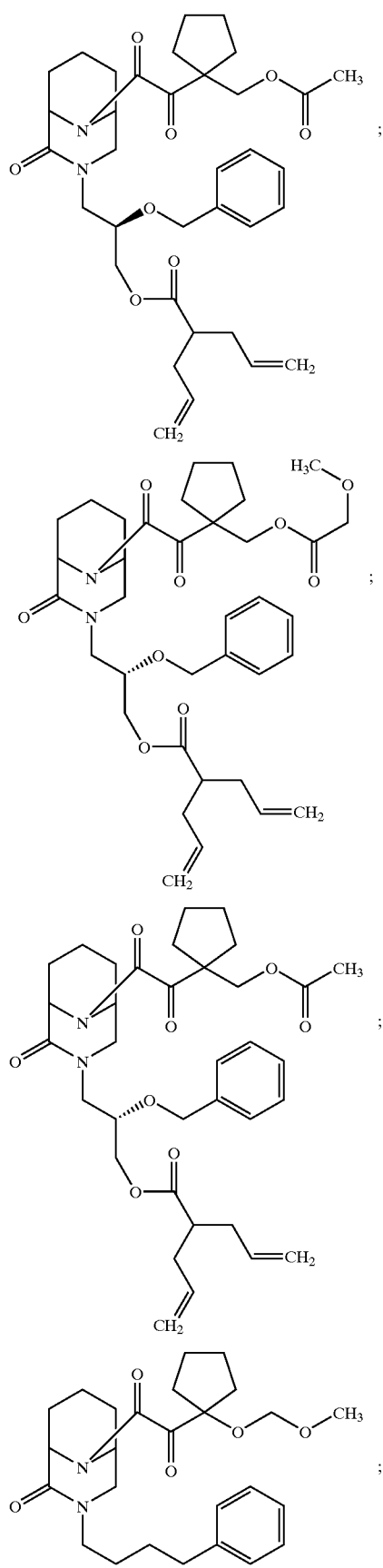
166
-continued
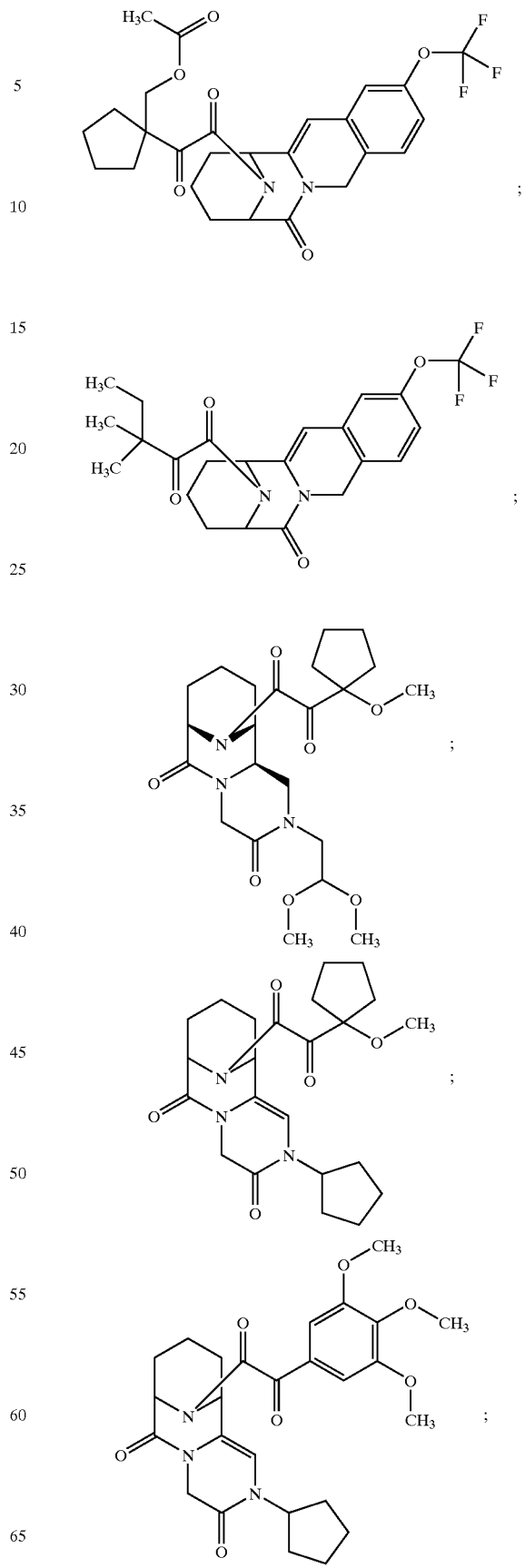

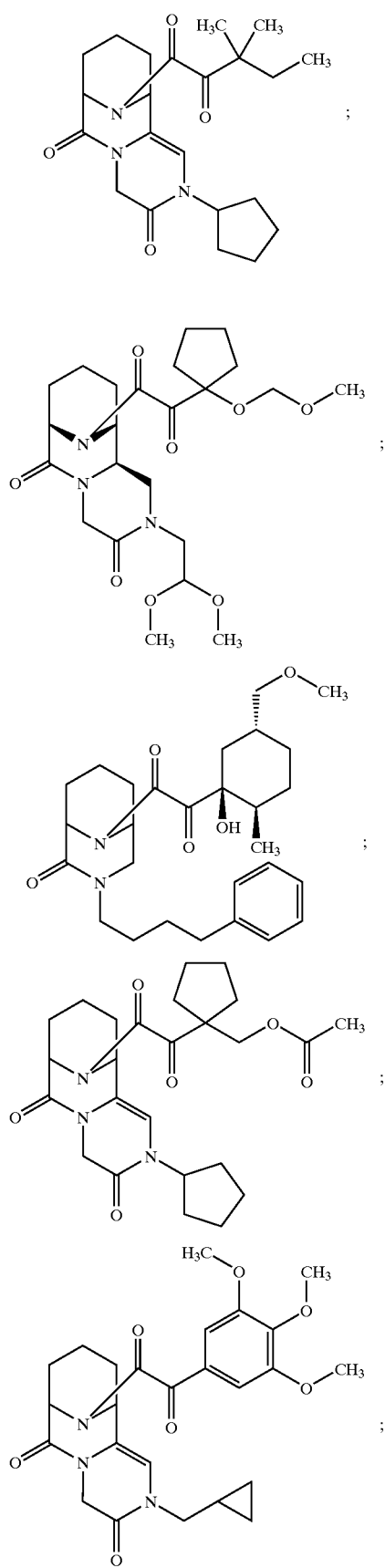
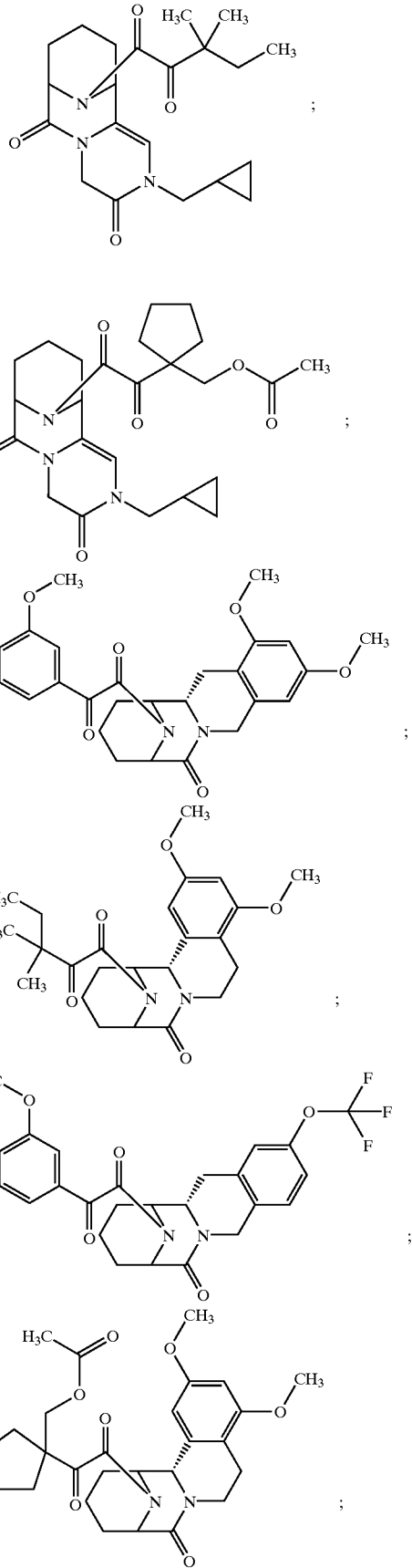

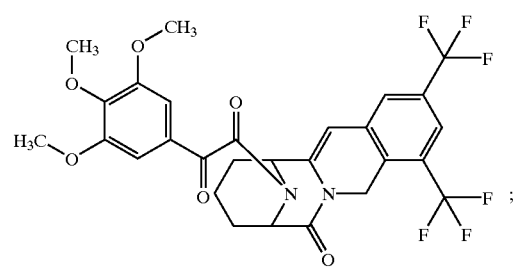
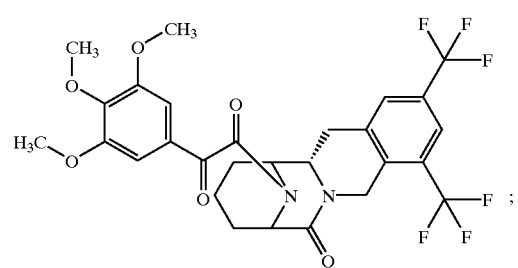
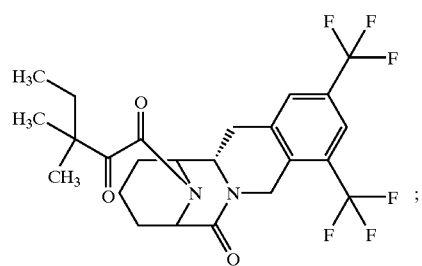
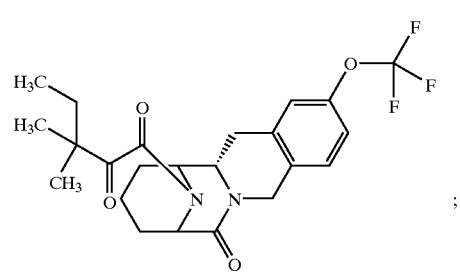
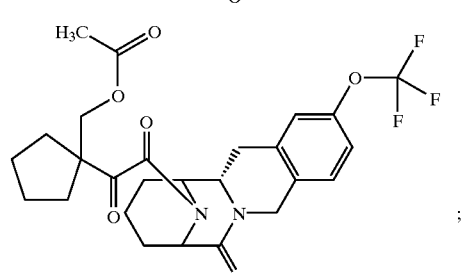
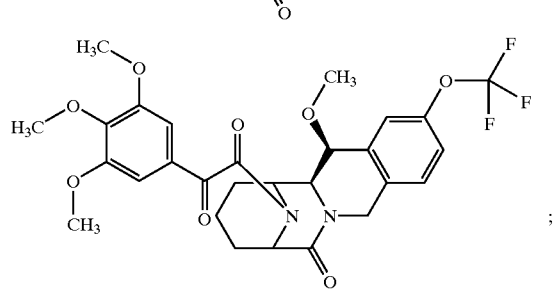
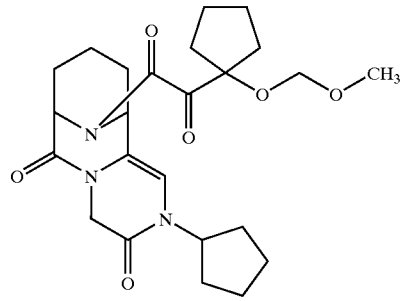
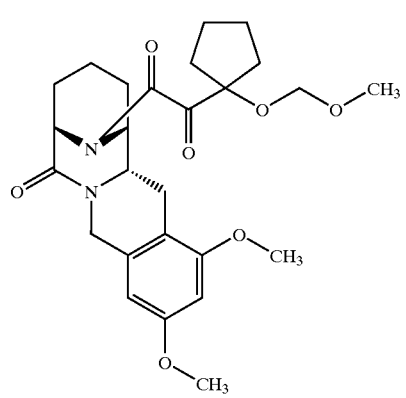
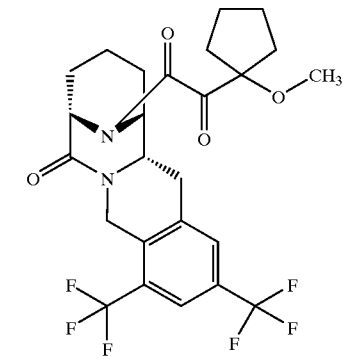
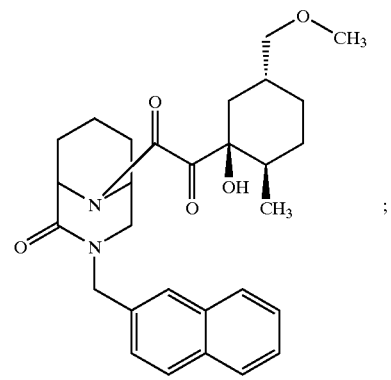

171
-continued
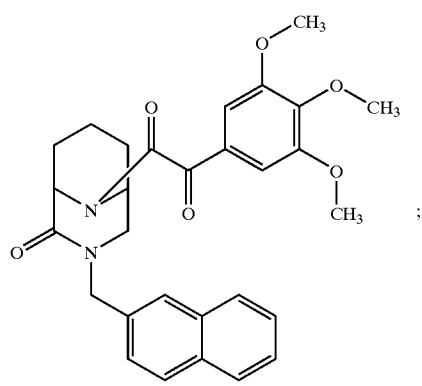
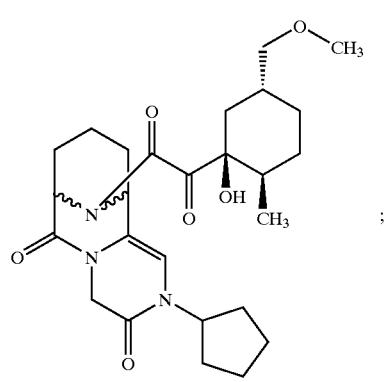
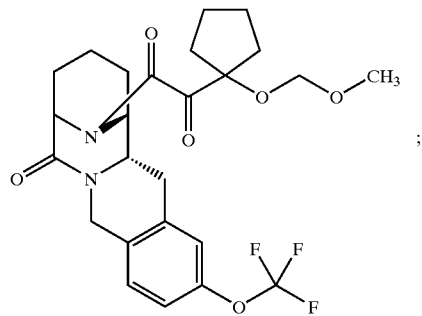
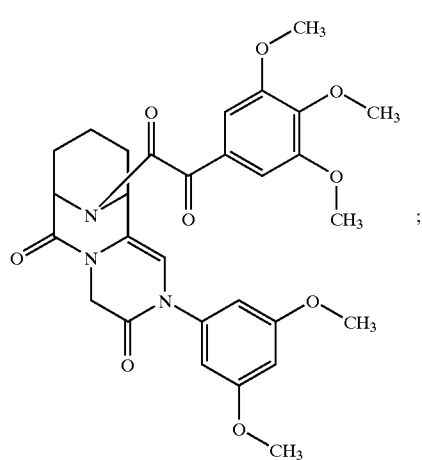
172
-continued
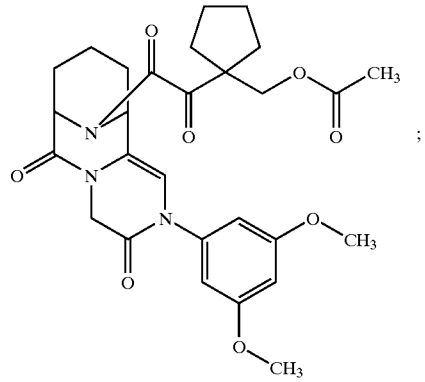
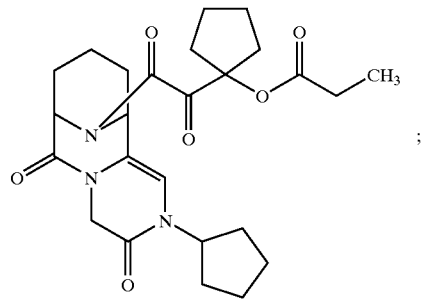
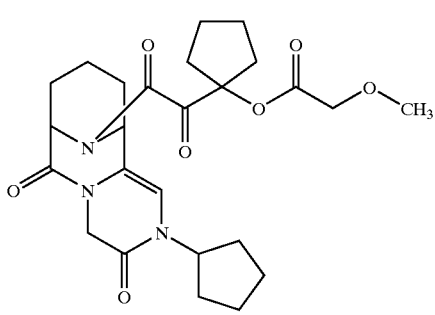
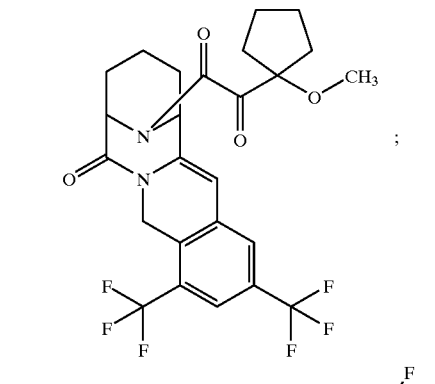
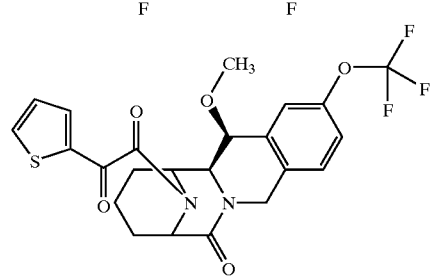

173
-continued
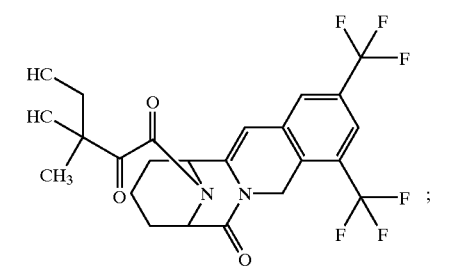
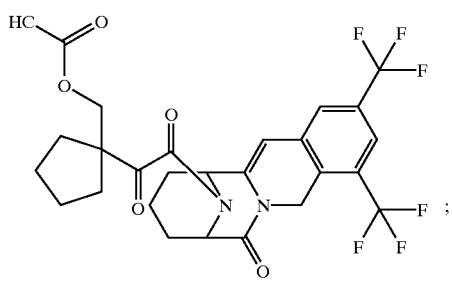
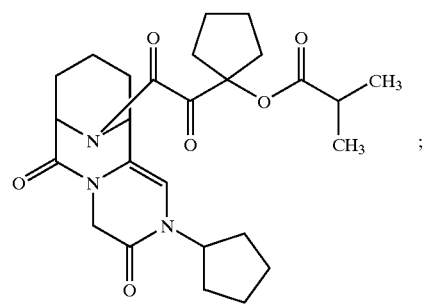
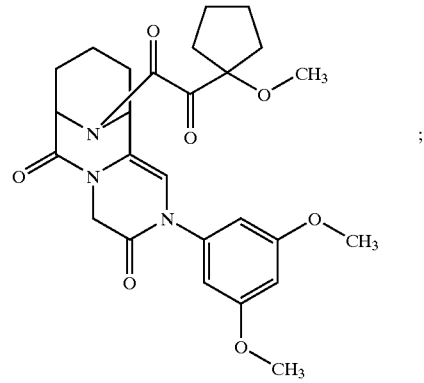
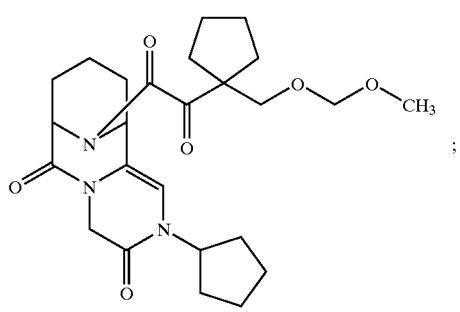
174
-continued
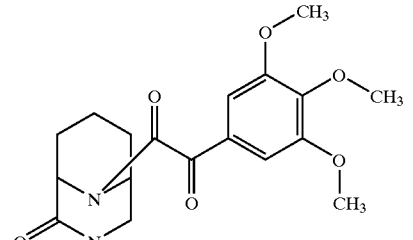
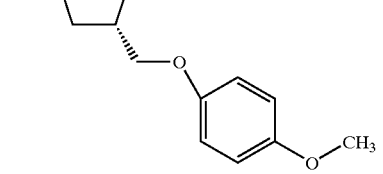
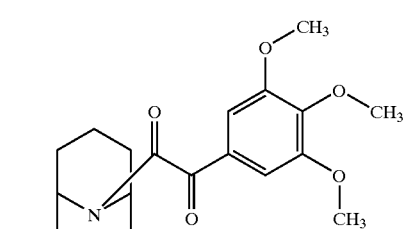
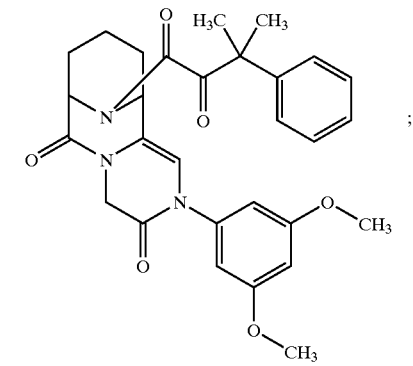
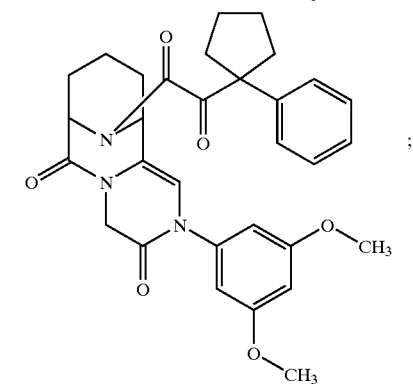

-continued

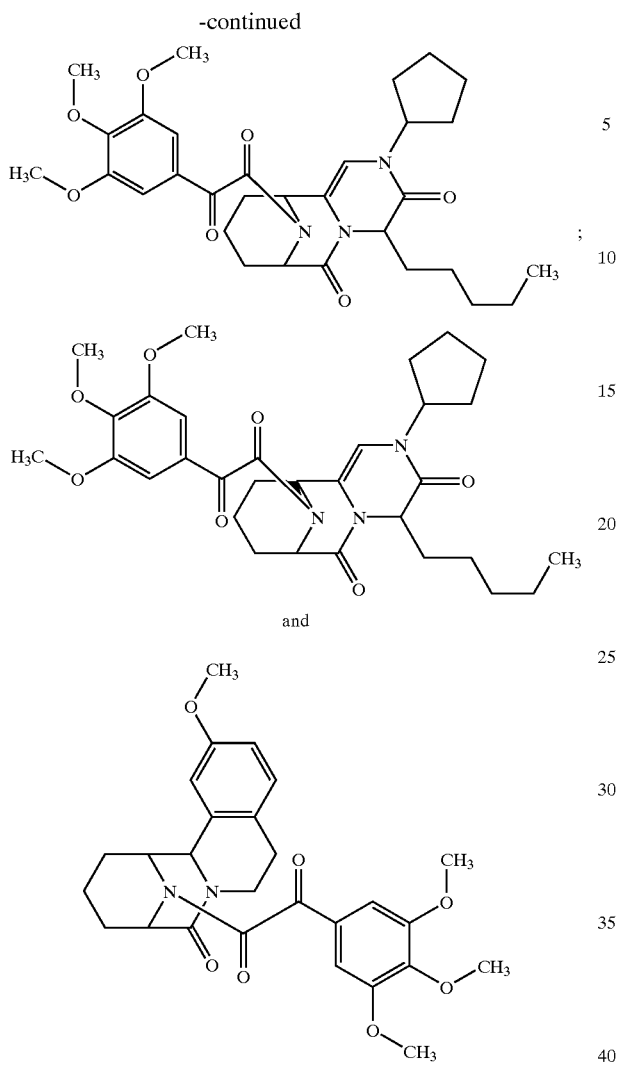

or pharmaceutically acceptable salt of said compound.

25. A compound selected from the group consisting of:

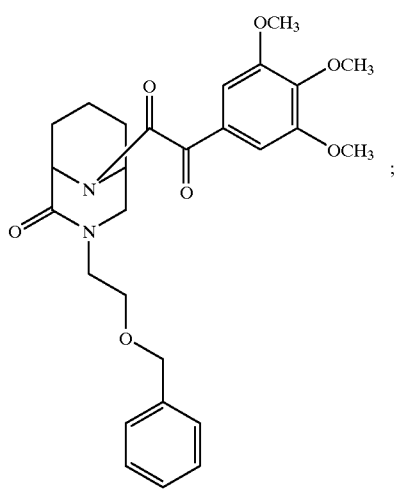

-continued

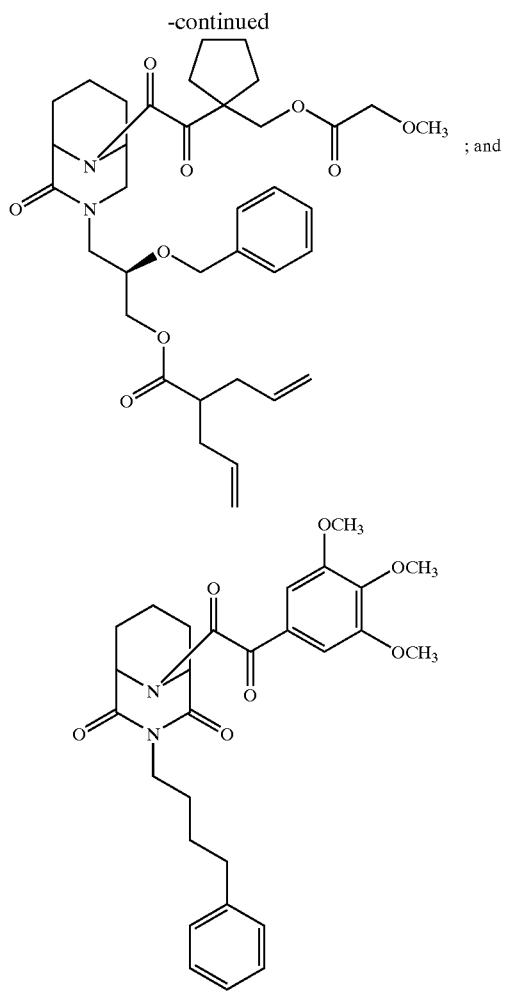

or pharmaceutically acceptable salt of said compound.

26. A process of making a compound according to claim 23, comprising:

(a) converting a compound of formula (III-a):

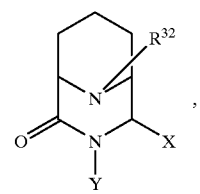

(III-a)

wherein:

R$^{32}$ is selected from the group consisting of optionally substituted alkyl, alkenyl, aryl, cycloalkyl, cycloalkenyl,

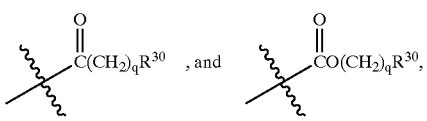

where q is 0 or 1, and R$^{30}$ is an alkyl or aryl group unsubstituted or substituted with one or more substituents independently selected from the group consisting of hydroxyl, $C_1$–$C_6$ alkyl, $C_2$–$C_6$ alkenyl, $C_1$–$C_4$ alkyloxy, $C_2$–$C_4$ alkenyloxy, benzyloxy, phenoxy, and phenyl;

X is: hydrogen; cyano; $C_1$–$C_2$ alkyloxy; dimethoxymethyl; or oxygen, where when X is oxygen, the bond connecting X to the ring carbon atom is a double bond; and Y is hydrogen or an alkyl, alkenyl, benzyl, or cycloalkyl group unsubstituted or substituted with one or more substituents independently selected from the group consisting of: alkyl; aryl; alkoxy; hydroxyalkyl; aryloxy; alkenyloxy; hydroxy; benzyloxy; phenoxy; $(CH_2)_p$—O—$W^2$ and $(CH_2)_p$—N—$W^2$ where p is 0, 1, or 2 and $W^2$ is $R^3$ or $C(O)R^3$, where $R^3$ is an aryl, alkyl, or alkenyl group unsubstituted or substituted with one or more substituents independently selected from the group consisting of aryl, alkyl, and alkoxy; and $(CH_2)_{p'}$—C(O)—O—$W^{2'}$ and $(CH_2)_{p'}$—C(O)—N—$W^{2'}$, where p' is 0, 1, or 2, and $W^{2'}$ is an alkyl;

or X and Y, together with the carbon ring atom and nitrogen heteroatom to which they are respectively bonded, form a 5- to 7-membered saturated or unsaturated heterocyclic ring unsubstituted or substituted with one or more substituents J, K, and L; where J, K, and L represent substituents independently selected from the group consisting of oxygen, and $C_3$–$C_5$ cycloalkyl and $C_1$–$C_5$ alkyl groups unsubstituted or substituted with one or more substituents independently selected from the group consisting of $C_3$–$C_5$ cycloalkyl, methoxy, methoxyphenyl, and dimethoxyphenyl; or where J and K together form a phenyl ring unsubstituted or substituted with one or more substituents independently selected from the group consisting of methoxy, trifluoromethyl, trifluoromethoxy, and substituents linked to the phenyl ring through oxygen, nitrogen, carbon or sulfur and independently selected from the group consisting of halogen, hydroxyl, $NO_2$, $CF_3$, $C_1$–$C_6$ alkyl, $C_2$–$C_6$ alkenyl, $C_1$–$C_4$ alkyloxy, $C_2$–$C_4$ alkenyloxy, benzyloxy, phenoxy, amino, and phenyl;

under reducing conditions to a compound of formula (III-b):

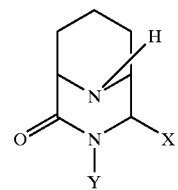

(III-b)

wherein X and Y are as defined above; and (b) coupling said compound of formula (III-b) with a compound of formula (IV):

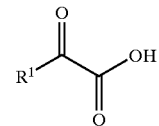

(IV)

wherein $R^1$ is: hydrogen; an aryl group unsubstituted or substituted with one or more substituents independently selected from the group consisting of halogen, hydroxyl, $NO_2$, $CF_3$, $C_1$–$C_6$ alkyl, $C_2$–$C_6$ alkenyl, $C_1$–$C_4$ alkyloxy, $C_2$–$C_4$ alkenyloxy, benzyloxy, phenoxy, amino, and phenyl; an alkyl or alkenyl group unsubstituted or substituted with one or more substituents independently selected from the group consisting of $C_1$–$C_4$ alkyl, $C_2$–$C_4$ alkenyl, $C_4$–$C_6$ cycloalkenyl, and hydroxy; a $C_3$–$C_8$ cycloalkyl or $C_5$–$C_7$ cycloalkenyl group unsubstituted or substituted with one or more substituents independently selected from the group consisting of $C_1$–$C_4$ alkyl, $C_2$–$C_4$ alkenyl, $C_1$–$C_4$ alkyloxy, and hydroxy; or $C(R^{11})(R^{12})(R^{13})$, where $R^{11}$ and $R^{12}$ are each independently lower alkyl, or $R^{11}$ and $R^{12}$ together with the atom to which they are bound form cycloalkyl, and $R^{13}$ is H, OH, lower alkyl, aryl, or $(CH_2)_n$—O—$W^1$, where n is 0, 1, 2, or 3, and $W^1$ is $R^2$ or $C(O)R^2$, with $R^2$ being $C_1$–$C_3$ alkyl unsubstituted or substituted with one or two methoxy groups.

* * * * *